United States Patent
Bennett et al.

(10) Patent No.: US 8,347,755 B2
(45) Date of Patent: Jan. 8, 2013

(54) TRANSMISSION WITH ADJUSTMENT MEMBER FOR VARYING TENSION FORCE

(75) Inventors: Richard P. Bennett, Cooper City, FL (US); Peter Ebbitt, Boca Raton, FL (US); Hyosig Kang, Weston, FL (US); James Polselli, Deerfield Beach, FL (US); Brian D. Schmitz, Fort Lauderdale, FL (US)

(73) Assignee: Mako Surgical Corp., Ft. Lauderdale, FL (US)

( * ) Notice: Subject to any disclaimer, the term of this patent is extended or adjusted under 35 U.S.C. 154(b) by 332 days.

(21) Appl. No.: 12/654,517

(22) Filed: Dec. 22, 2009

(65) Prior Publication Data
US 2010/0170361 A1   Jul. 8, 2010

Related U.S. Application Data

(60) Provisional application No. 61/203,475, filed on Dec. 23, 2008.

(51) Int. Cl.
*B25J 5/00* (2006.01)
(52) U.S. Cl. ............... 74/490.04; 74/490.05; 901/21; 474/84
(58) Field of Classification Search ........... 74/490.04, 74/490.05; 474/84; 901/21, 28
See application file for complete search history.

(56) References Cited

U.S. PATENT DOCUMENTS

| | | | |
|---|---|---|---|
| 1,694,652 A * | 12/1928 | Hager | 105/101 |
| 3,353,771 A | 11/1967 | Te Bow | |
| 4,290,574 A | 9/1981 | Archibald | |
| 4,294,548 A * | 10/1981 | Watson | 366/60 |
| 4,360,974 A | 11/1982 | De Cuissart | |
| 4,541,178 A | 9/1985 | White | |
| 4,610,020 A | 9/1986 | La Fiandra | |
| 4,770,497 A | 9/1988 | Brown | |
| 5,046,375 A | 9/1991 | Salisbury et al. | |
| 5,161,424 A | 11/1992 | Saberton et al. | |
| 5,167,464 A | 12/1992 | Voellmer | |
| 5,207,114 A * | 5/1993 | Salisbury et al. | 74/479.01 |
| 5,513,946 A | 5/1996 | Sawada et al. | |

(Continued)

FOREIGN PATENT DOCUMENTS
EP    1 815 949 A1    8/2007
(Continued)

OTHER PUBLICATIONS

U.S. Appl. No. 12/654,518, filed Dec. 22, 2009, Bennett et al.

(Continued)

*Primary Examiner* — Troy Chambers
*Assistant Examiner* — Terence Boes
(74) *Attorney, Agent, or Firm* — Foley & Lardner LLP

(57) ABSTRACT

A transmission apparatus includes a drive member, a driven member, and an at least partially flexible transmission coupled to the drive member and the driven member. The flexible transmission is configured to cause movement of the driven member in response to movement of the drive member. The flexible transmission includes a first tension element having a first portion coupled to the drive member, a second portion coupled to the driven member, and an intermediate portion between the first portion and the second portion. The transmission apparatus also includes an adjustment member that engages the intermediate portion of the first tension element. The adjustment member is configured to be adjusted to vary a tension force applied to the first tension element.

17 Claims, 51 Drawing Sheets

U.S. PATENT DOCUMENTS

| | | | |
|---|---|---|---|
| 5,778,730 | A | 7/1998 | Solomon et al. |
| 5,794,487 | A | 8/1998 | Solomon et al. |
| 5,816,770 | A | 10/1998 | Itagaki |
| 6,152,941 | A | 11/2000 | Himes et al. |
| 6,236,788 | B1 | 5/2001 | Moisel |
| 6,370,974 | B1 | 4/2002 | Jourtchenko et al. |
| 6,394,998 | B1 | 5/2002 | Wallace et al. |
| 6,668,466 | B1 | 12/2003 | Bieg et al. |
| 6,688,189 | B2 | 2/2004 | Hashimoto et al. |
| 6,729,589 | B2 | 5/2004 | Shelef |
| 6,826,324 | B2 | 11/2004 | Steinberg et al. |
| 7,021,167 | B2 | 4/2006 | Liesegang |
| 7,316,681 | B2 * | 1/2008 | Madhani et al. ............ 606/1 |
| 2002/0035372 | A1 | 3/2002 | Zisterer et al. |
| 2003/0075790 | A1 | 4/2003 | Steinberg et al. |
| 2003/0104886 | A1 | 6/2003 | Gajewski |
| 2003/0152661 | A1 | 8/2003 | Yu et al. |
| 2004/0049205 | A1 | 3/2004 | Lee et al. |
| 2006/0016061 | A1 | 1/2006 | Shelef |
| 2006/0047272 | A1 | 3/2006 | McPherson et al. |
| 2007/0089557 | A1 | 4/2007 | Solomon et al. |
| 2007/0142969 | A1 | 6/2007 | Devengenzo et al. |
| 2007/0299427 | A1 | 12/2007 | Yeung et al. |
| 2008/0010706 | A1 | 1/2008 | Moses et al. |
| 2008/0021440 | A1 | 1/2008 | Solomon |
| 2008/0058861 | A1 | 3/2008 | Cooper et al. |
| 2008/0087871 | A1 | 4/2008 | Schena |
| 2008/0248907 | A1 | 10/2008 | Cottrell |
| 2008/0278105 | A1 | 11/2008 | Somes |
| 2008/0287862 | A1 | 11/2008 | Weitzner et al. |
| 2010/0166496 | A1 | 7/2010 | Bennett et al. |
| 2010/0168723 | A1 | 7/2010 | Suarez et al. |
| 2010/0170362 | A1 | 7/2010 | Bennett et al. |
| 2011/0174097 | A1 | 7/2011 | Bergamasco et al. |

FOREIGN PATENT DOCUMENTS

| | | |
|---|---|---|
| EP | 1 815 950 A1 | 8/2007 |
| EP | 1 915 966 A1 | 4/2008 |
| WO | WO 2010-074739 | 7/2010 |
| WO | WO 2010-074742 | 7/2010 |
| WO | WO 2010-074744 | 7/2010 |
| WO | WO 2010-075404 | 7/2010 |

OTHER PUBLICATIONS

International Search Report mailed May 7, 2010 in PCT/US2009/006655, 4 pages.
International Search Report mailed May 7, 2010 in PCT/US2009/006659, 4 pages.
International Search Report mailed May 7, 2010 in PCT/US2009/006661, 4 pages.
PCT Written Opinion mailed May 7, 2010 in PCT/US2009/006655, 6 pages.
PCT Written Opinion mailed May 7, 2010 in PCT/US2009/006659, 6 pages.
PCT Written Opinion mailed May 7, 2010 in PCT/US2009/006661, 6 pages.
International Search Report corresponding to PCT/US2009/069231, dated Mar. 22, 2010, 4 pages.
PCT Written Opinion corresponding to PCT/US2009/069231, dated Mar. 22, 2010, 5 pages.

* cited by examiner

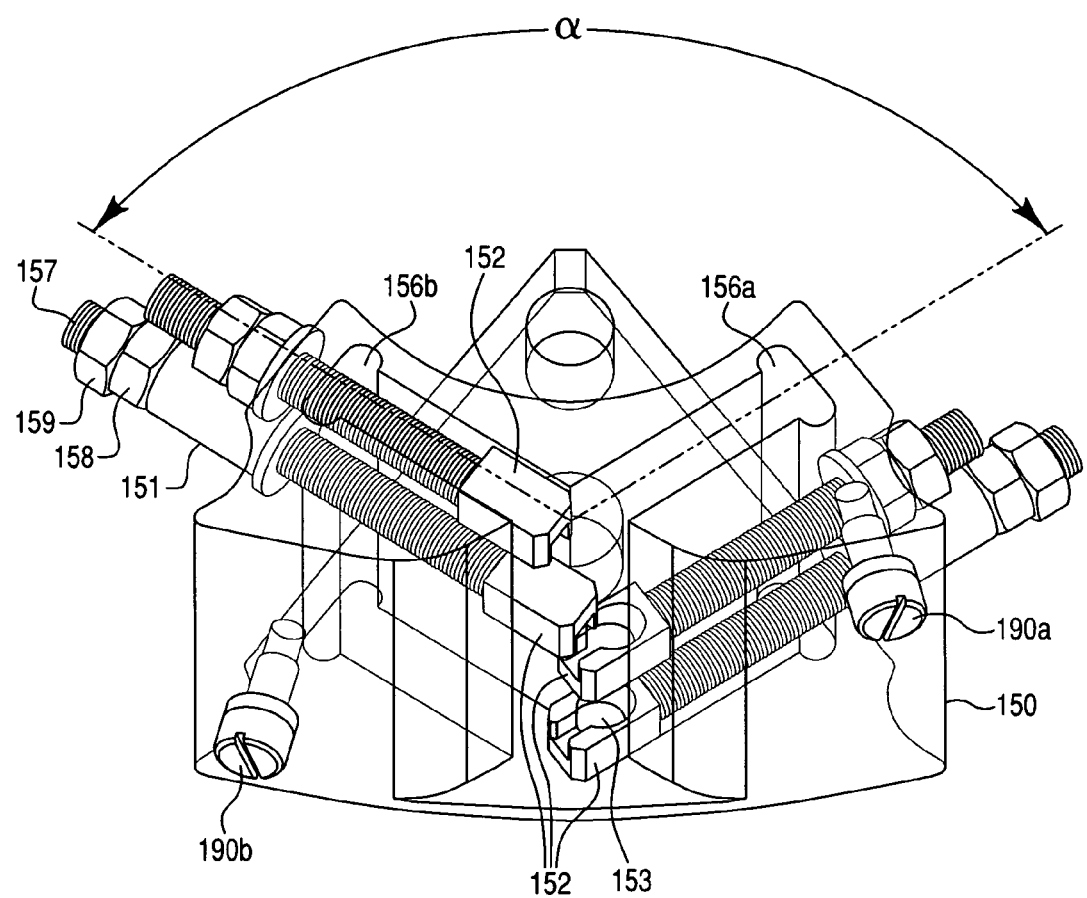

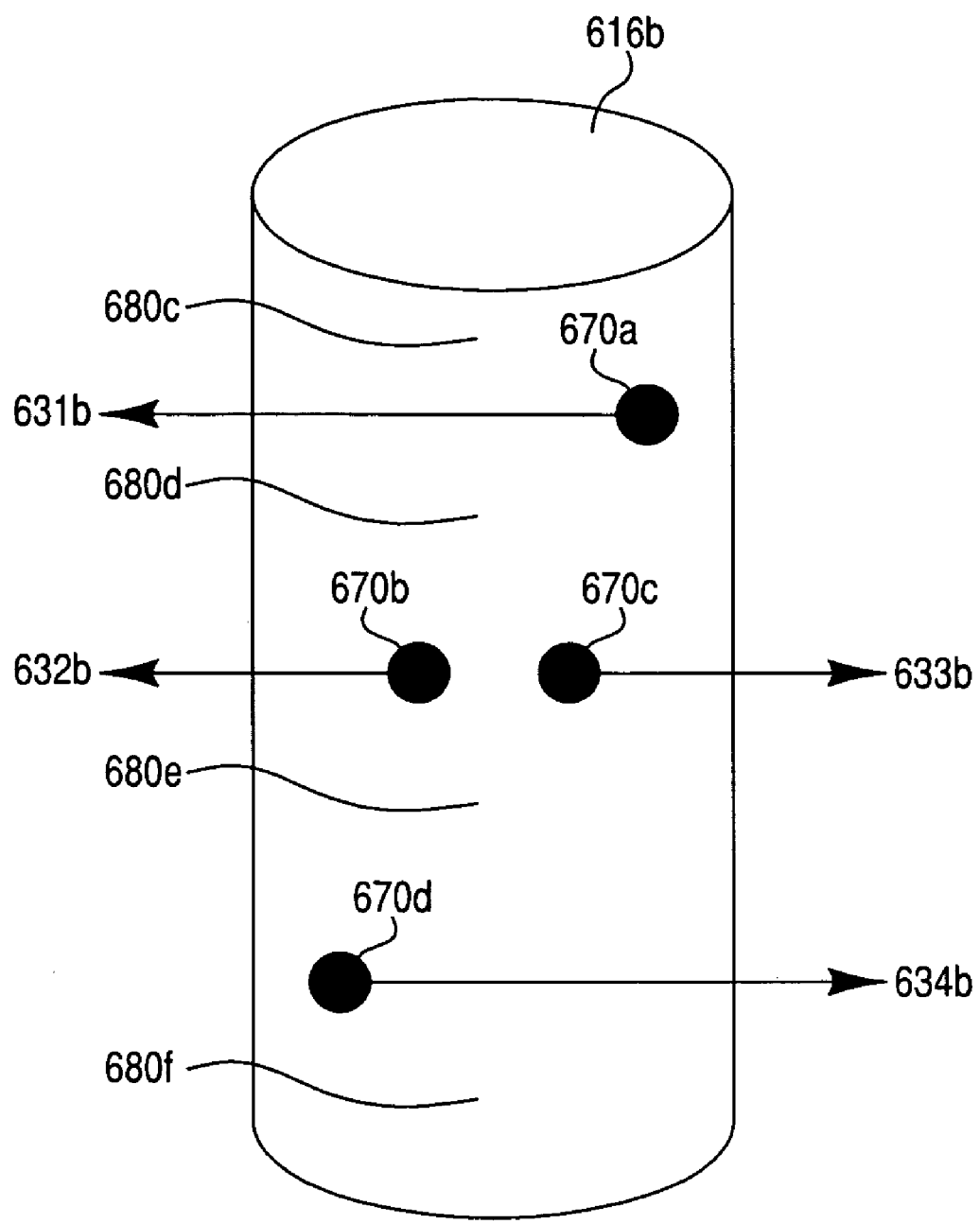

TRANSMISSION WITH ADJUSTMENT MEMBER FOR VARYING TENSION FORCE

CROSS-REFERENCE TO RELATED PATENT APPLICATIONS

This application claims priority to U.S. Provisional Patent Application Ser. No. 61/203,475, filed on Dec. 23, 2008, which is hereby incorporated by reference in its entirety.

BACKGROUND OF THE INVENTION

1. Field of Invention

The present invention relates to a transmission, particularly a tension element drive system for a robotic arm.

2. Description of Related Art

Robotic systems are often used in applications that require a high degree of accuracy and/or precision, such as surgical procedures or other complex tasks. Such systems may include various types of robots, such as autonomous, teleoperated, semi-active, passive, and interactive. For example, in joint replacement surgery, a surgeon can use an interactive, haptically guided robotic arm in a passive manner to sculpt bone to receive a joint implant, such as a knee implant. To sculpt bone, the surgeon manually grasps and manipulates the robotic arm to move a cutting tool (such as a burr) that is coupled to the robotic arm. As long as the surgeon maintains the cutting tool within a predefined virtual cutting boundary, the robotic arm moves freely with low friction and low inertia such that the surgeon perceives the robotic arm as weightless and can move the robotic arm as desired. If the surgeon attempts to cut outside the virtual cutting boundary, however, the robotic arm provides haptic (or force) feedback that prevents or inhibits the surgeon from moving the cutting tool beyond the virtual cutting boundary. In this manner, the robotic arm enables highly accurate, repeatable bone cuts.

The ability of a robotic arm to function in the above-described manner is dependent on the drive system (also called the drive train or drive transmission) of the robotic arm. Ideally, the drive system is characterized by low friction, low inertia, high stiffness, large bandwidth, near-zero backlash, force fidelity, and/or backdrivability. A flexible transmission, such as a tension element drive system, may have these characteristics. One difficulty with conventional tension element drive systems, however, is that they may not be sufficiently fail-safe for use in surgical applications where failure of the drive system could endanger a patient. For example, failure of one tension element (e.g., a cable or cord) in the drive system could result in unintended movement of the robotic arm that could harm the patient. To improve safety, the robotic arm can include joint brakes to constrain movement of the joints of the robotic arm in the event of a tension element failure. Incorporation of joint brakes, however, increases the weight and inertia of the robotic arm, which adversely impacts backdrivability and haptic response.

Another difficulty with conventional tension element drive systems is that the tension elements must be pre-tensioned to eliminate slack that may cause backlash. Pre-tensioning loads, however, are about 15% to 50% of the breaking strength of the tension element, which imparts large forces to drive system components, bearings, and support structure. The high load also increases friction forces in the drive system components and contributes to surgeon fatigue.

Another difficulty with conventional tension element drive systems is that such drive systems may not be easily manufactured, serviced, and/or upgraded. For example, a conventional tension element drive system may be an integral system in the sense that components in one part of the drive system (e.g., in one joint) are, to some degree, dependent on or impacted by components in another part of the drive system (e.g., in another joint). Thus, if one portion of the drive system is defective, it may be necessary to dismantle other portions of the drive system that are functioning properly in order to repair the defective portion. For example, repairing a problem in one joint of the robotic arm may require de-cabling multiple joints of the robotic arm. The inability to isolate portions of a conventional tension element drive system increases the time and labor required to service and upgrade the robotic arm, which results in costly repairs and lengthy downtime that reduces a hospital's ability to optimize use of the robotic arm.

SUMMARY

An embodiment of a transmission apparatus according to the present invention includes a drive member, a driven member, and an at least partially flexible transmission coupled to the drive member and the driven member. The flexible transmission is configured to cause movement of the driven member in response to movement of the drive member. The flexible transmission includes a first tension element having a first portion coupled to the drive member, a second portion coupled to the driven member, and an intermediate portion between the first portion and the second portion. The transmission apparatus also includes an adjustment member that engages the intermediate portion of the first tension element. The adjustment member is configured to be adjusted to vary a tension force applied to the first tension element.

BRIEF DESCRIPTION OF THE DRAWINGS

The accompanying drawings, which are incorporated and constitute a part of this specification, illustrate embodiments of the invention and together with the description serve to explain aspects of the invention.

FIGS. 9A and 9B are top perspective views of the connection mechanism of FIG. 8B.

FIG. 30 is a schematic of an embodiment of a flexible transmission coupled to a drive member of the fourth module of FIG. 28A.

DETAILED DESCRIPTION OF PREFERRED EMBODIMENTS

Figure 1:
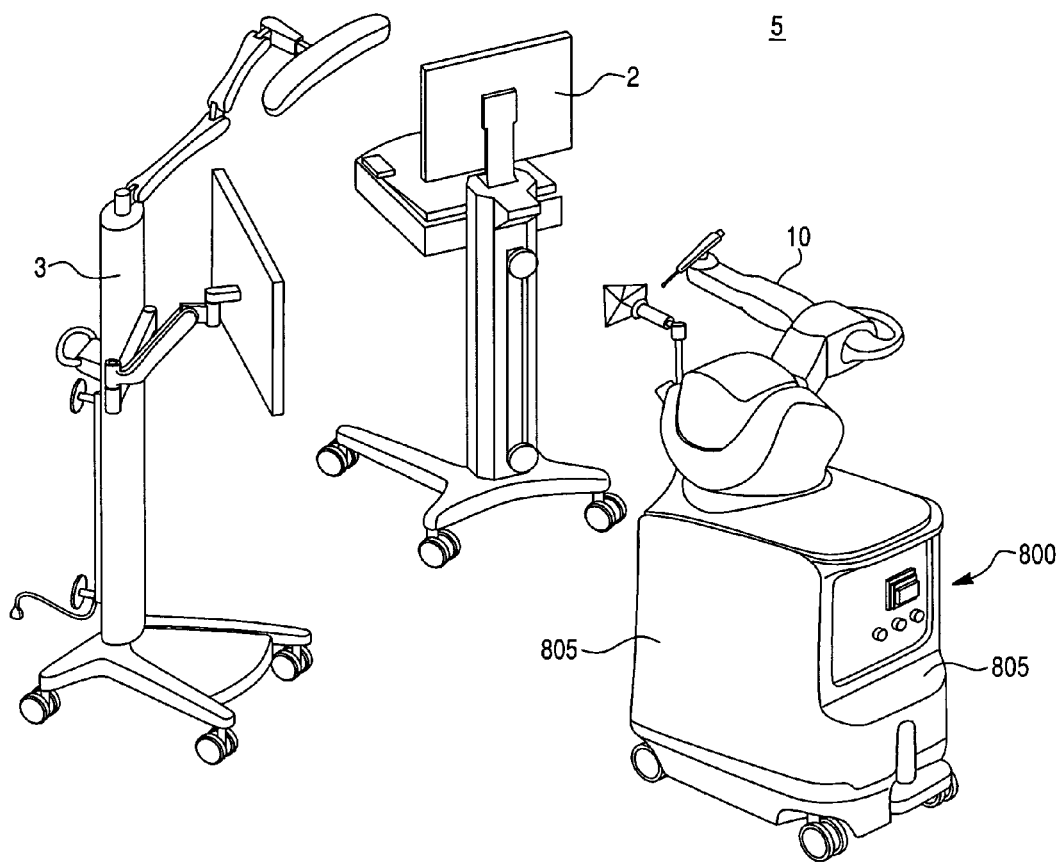
FIG. 1 is a perspective view of a surgical system according to an embodiment.

Presently preferred embodiments of the invention are illustrated in the drawings. An effort has been made to use the same or like reference numbers throughout the drawings to refer to the same or like parts. Although this specification refers primarily to a robotic arm for orthopedic procedures, it should be understood that the subject matter described herein is applicable to other types of robotic systems, including those used for surgical and non-surgical applications, as well as to non-robotic systems that include flexible transmissions.

Overview

A robotic system for surgical applications according to the present invention preferably includes a robotic arm that is used in an interactive manner by a surgeon to perform a surgical procedure on a patient. In a preferred embodiment the robotic system is the RIO® Robotic Arm Interactive Orthopedic System manufactured by MAKO Surgical Corp. of Fort Lauderdale, Fla. The robotic arm is preferably a haptic device that works in combination with a computer aided navigation system and a tracking device. For example, as described in U.S. patent application Ser. No. 11/357,197 (Pub. No. US 2006/0142657), filed Feb. 21, 2006, and hereby incorporated by reference herein in its entirety, a surgical tool, such as a cutting burr, is coupled to the robotic arm. The surgeon manually moves the robotic arm to manipulate the surgical tool to perform a surgical task on the patient, such as bone cutting for a joint replacement operation. As the surgeon manipulates the tool, the robotic arm provides haptic (or force) feedback to limit the surgeon's ability to move the cutting tool beyond a predefined virtual cutting boundary, which results in highly accurate and repeatable bone cuts. The robotic arm works in a passive manner and provides haptic feedback only when the surgeon attempts to cut bone that lies outside the virtual cutting boundary. The haptic feedback is generated by one or more actuators (e.g., motors) in the robotic arm and is transmitted to the surgeon via a flexible transmission, such as a tension element transmission. When the robotic arm is not providing haptic feedback, the robotic arm 10 is freely moveable by the surgeon.

Exemplary Robotic Arm Devices

Figure 2:
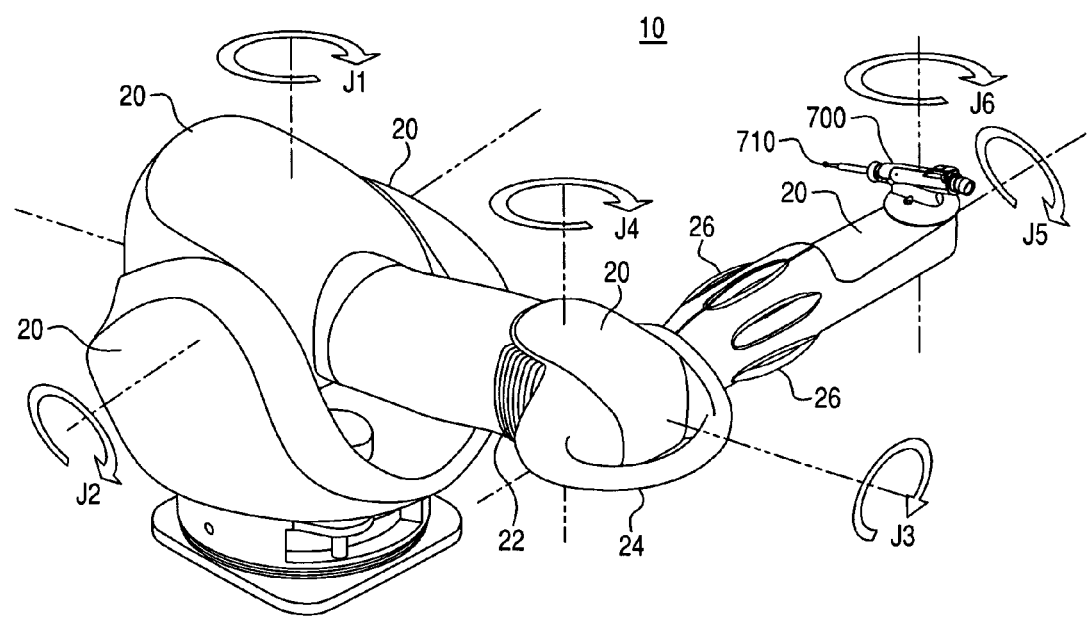
FIG. 2 is a perspective view of an embodiment of a robotic arm of the surgical system of FIG. 1.
Figure 3:
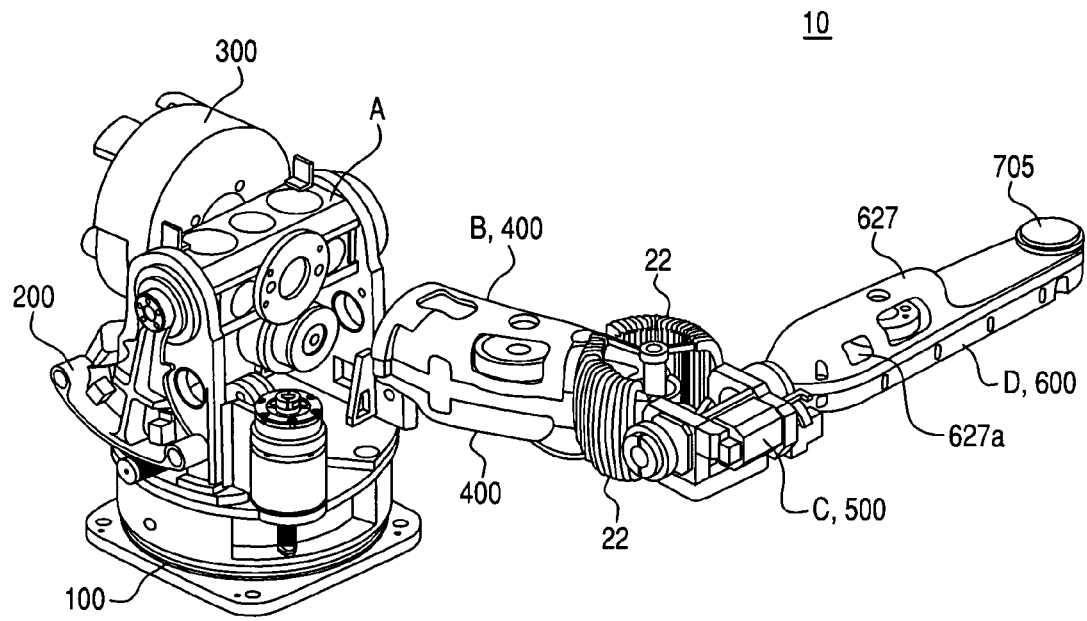
FIG. 3 is a perspective view of the robotic arm of FIG. 2 with protective covers removed.

FIG. 1 shows an example of a surgical system 5 that includes a robotic arm 10 according to an embodiment of the invention. The surgical system 5 may also include a computer aided navigation system 2 and a tracking device 3. The robotic arm 10 includes one or more joint assemblies that provide, for example, rotational degrees of freedom of movement. As illustrated in FIGS. 2 and 3, the robotic arm 10 includes a first joint assembly 100 that provides a first rotational degree of freedom (DOF) J1, a second joint assembly 200 that provides a second rotational DOF J2, a third joint assembly 300 that provides a third rotational DOF J3, a fourth joint assembly 400 that provides a fourth rotational DOF J4, a fifth joint assembly 500 that provides a fifth rotational DOF J5, and a sixth joint assembly 600 that provides a sixth rotational DOF J6. An end effector 700 is coupled to the output of the sixth joint assembly 600. As described further below, each of the joint assemblies 100, 200, 300, 400, 500, 600 includes a first component having a drive member, a second component, and first and second transmission elements each coupled to the first component and the second component and configured to cause movement of at least one of the first and second components in response to movement of the drive member. Although the embodiment of FIGS. 1-3 includes six degrees of freedom, the robotic arm 10 may include more or fewer degrees of freedom depending on the application for which the robotic arm 10 will be used.

Each rotational degree of freedom has a positive direction (indicated by the arrows in FIG. 2) and an opposite negative direction and preferably has a limited total range of motion. For example, in an exemplary embodiment, a range of motion of the first joint assembly 100 is about 250 degrees, a range of motion of the second joint assembly 200 is about 40 degrees, a range of motion of the third joint assembly 300 is about 270 degrees, a range of motion of the fourth joint assembly 400 is about 100 degrees, a range of motion of the fifth joint assembly 500 is about 270 degrees, and a range of motion of the sixth joint assembly 600 is about 260 degrees. These exemplary ranges of motion provide the robotic arm 10 with sufficient dexterity for tasks requiring high accuracy and precision, such as surgery. Additionally, the exemplary ranges of motion enable the robotic arm 10 to be manipulated by both right and left handed users. For example, the robotic arm 10 shown in FIG. 2 is configured for a right handed user. Typically, to manipulate the robotic arm 10, a right handed user will place his or her right hand on the end effector 700 and his or her left hand on either a handle 24 located on the fifth joint assembly 500 or projections 26 located on the sixth joint assembly 600. This configuration, however, does not work well for a left handed user because the user cannot easily grasp the end effector 700 with his or her left hand. To reconfigure the robotic arm 10 for a left handed user, the robotic arm 10 is symmetrically flipped from the pose shown in FIG. 2. In particular, in the left handed configuration, relative to FIG. 2, the first rotational DOF J1 is 180 degrees from that shown, the third rotational degree of freedom J3 is −180 degrees from that shown, the fifth rotational degree of freedom J5 is −180 degrees from that shown, and the sixth rotational degree of freedom J6 is 180 degrees from that shown.

To protect the mechanisms of the joint assemblies from damage and/or contamination and to shield the surgeon from potential hazards (e.g., pinch hazards), the robotic arm 10 includes protective covers 20. As shown in FIG. 2, the protective covers 20 encase the joint assemblies. In contrast, FIG. 3 shows the robotic arm 10 with the protective covers 20 removed and the joint assemblies exposed. The protective covers 20 may be formed of rigid plastic, such as molded plastic sheeting made of a durable thermoplastic alloy. In addition to rigid protective covers, the robotic arm 10 may also include flexible covers, such as a bellows 22. As shown in FIG. 3, the bellows 22 covers a gap between the fourth and fifth joint assemblies 400, 500 to simultaneously protect the surgeon from pinch hazards and allow the gap to expand and contract over the range of motion of the fourth joint assembly 400.

Figure 4:
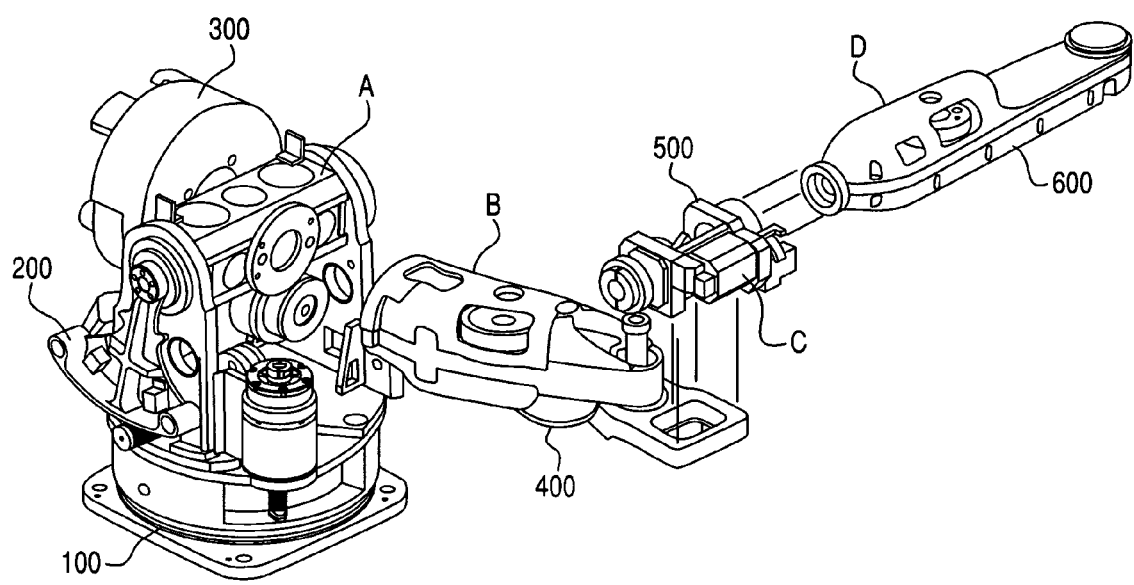
FIG. 4 is a perspective view of the robotic arm of FIG. 2 with protective covers removed and showing modular construction.

Preferably, the robotic arm 10 has a modular design where one or more of the joint assemblies comprise modules that can be independently manufactured and tested before being integrated with the remaining joint assemblies. Modularity advantageously improves manufacturing workflow, especially for high volume production. Modularity also improves serviceability by enabling service personnel to replace only those joint assemblies that require replacement. In addition, modularity enables the robotic arm 10 to be upgraded in the field by replacing one or more existing modular joint assemblies with alternative modular joint assemblies. For example, the degrees of freedom of the robotic arm 10 can be increased or decreased by replacing one or more of the existing modules with a module having a different design. In this manner, features of the robotic arm 10 can be tailored for each application without requiring changes to the overall design of the robotic arm 10. The number of modules and the characteristics of each can be determined based upon various factors, such as desired physical and performance characteristics. For example, in one embodiment, the robotic arm 10 has four modules. As shown in FIG. 4, a first module A includes the first, second, and third joint assemblies 100, 200, 300. A second module B attaches to the first module A and includes the fourth joint assembly 400. A third module C attaches to the second module B and includes the fifth joint assembly 500. A fourth module D attaches to the third module C and includes the sixth joint assembly 600.

FIGS. 5A to 5E show the first module A according to an embodiment of the invention. In this embodiment, the first module A includes the first, second, and third joint assemblies 100, 200, 300. As noted above, each joint assembly 100, 200, 300 provides one rotational degree of freedom. Thus, the first module A provides the first three degrees of freedom of the robotic arm 10. The output motion of the first module A is similar to the motion of a human shoulder joint. For this reason, the first module A is also referred to as the robot shoulder. Preferred embodiments of the joint assemblies 100, 200, 300 will now be described in detail. Specific descriptions of individual joint assemblies are exemplary only and are to be considered in all respects illustrative rather than limiting of the invention described herein. One skilled in the art will realize the invention may be embodied in other specific forms without departing from the spirit or essential characteristics thereof.

First Joint Assembly

Figure 6:
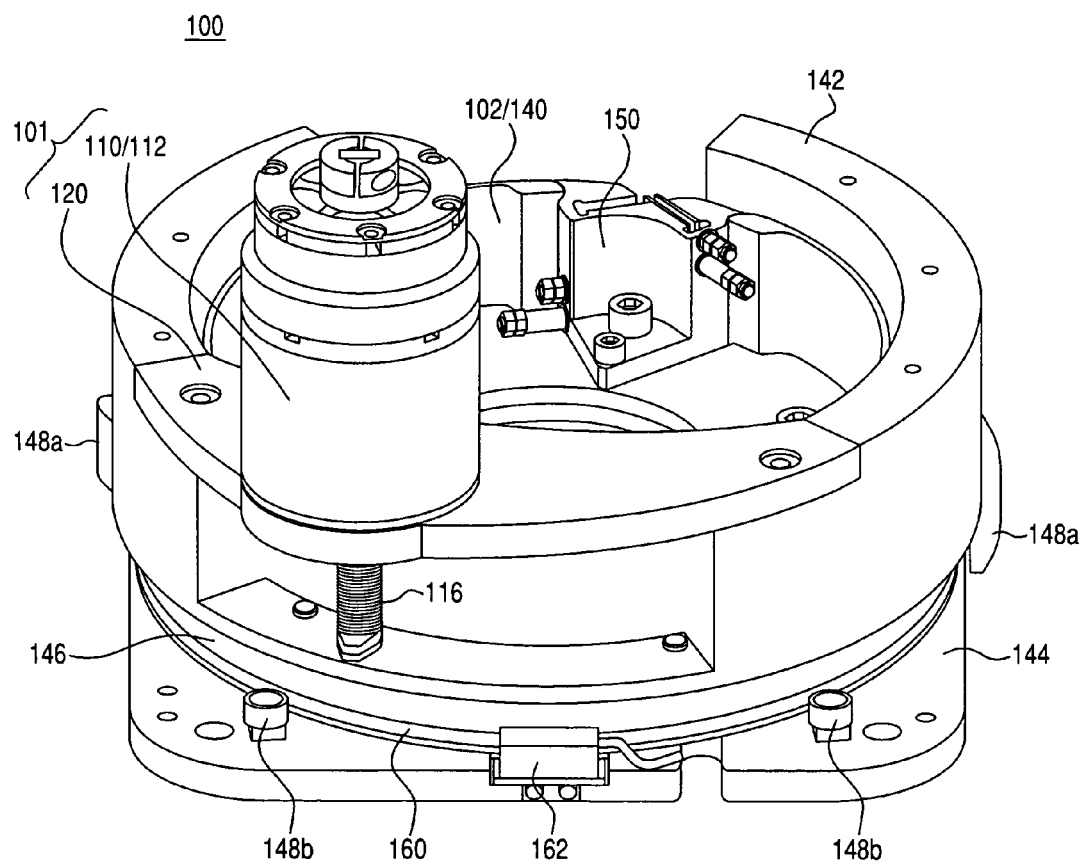
FIG. 6 is a perspective view of an embodiment of a joint assembly of the first module of FIG. 5A.

FIG. 6 shows the first joint assembly 100 according to an embodiment of the invention. The first joint assembly 100 includes a first component 101, a second component 102, and an at least partially flexible transmission 103 (see FIG. 8A). In this embodiment, the first component 101 includes a drive member 110 and a driven member 120. The flexible transmission 103 is coupled to the drive member 110 and the second component 102. When actuated, the drive member 110 imparts rotational motion to the driven member 120 via the flexible transmission 103.

The flexible transmission 103 is configured to transmit force and/or torque from the drive member 110 resulting in motion of the driven member 120. Preferably, the flexible transmission 103 is a tension element drive system (e.g., a cable, steel tape, or polymeric tendon transmission). In an exemplary embodiment, the flexible transmission 103 is a cable drive system. Cable drive systems have advantages over other mechanical drive systems, such as gears and linkages, because cable drive systems can be configured to provide low friction, low inertia, low compliance (i.e., high stiffness), large bandwidth, near-zero backlash, force fidelity, and/or backdrivability. In one embodiment, the flexible transmission 103 includes a first transmission element having a first plurality of transmission sub-elements and a second transmission element having a second plurality of transmission sub-elements. The transmission sub-elements are preferably tension elements, such as cables (or cords). In this embodiment, the first transmission element is a first cable set that includes the first plurality of transmission sub-elements, which are a first cable 130 (i.e., a first transmission sub-element) and a second cable 131 (i.e., a second transmission sub-element). Similarly, the second transmission element is a second cable set that includes the second plurality of transmission sub-elements, which are a third cable 133 (i.e., a third transmission sub-element) and a fourth cable 134 (i.e., a fourth transmission sub-element). The cables 131, 132, 133, 134 may be any cables appropriate for use in a robotic system but are preferably tungsten cables. Although the cables 131, 132, 133, 134 can be configured in a variety of ways to impart motion to the driven member 120, in this embodiment, each of the cables 131, 132, 133, 134 has a proximal end connected to the drive member 110 and a distal end connected to the second component 102 via a connection mechanism 150. The second component 102 includes a main drive 140 that is stationary relative to the first component 101. The manner in which motion is imparted to the driven member 120 is explained below.

In this embodiment, the driven member 120 is the joint output of the first joint assembly 100. As shown in FIG. 6, the driven member 120 includes a riser assembly 142 that can be coupled to a baseplate 144 by, for example, a cross roller bearing 146. For example, an inner race of the cross roller bearing 146 is connected to the baseplate 144, and an outer race of the cross roller bearing 146 is connected to the riser assembly 142. The cross roller bearing 146 is a precision bearing that enables the riser assembly 142 to rotate with low friction relative to the baseplate 144. To limit rotation of the riser assembly 142, hard stops 148a are disposed on the riser assembly 142 and corresponding hard stop bumpers 148b are disposed on the baseplate 144. When rotation of the riser assembly 142 causes one of the hard stops 148a to contact one of the hard stop bumpers 148b, rotation of the riser assembly 142 is constrained. As discussed further below, the driven member 120 (i.e., the riser assembly 142) is preferably unbraked, meaning that the driven member 120 does not have a brake mechanism.

Figure 7A:
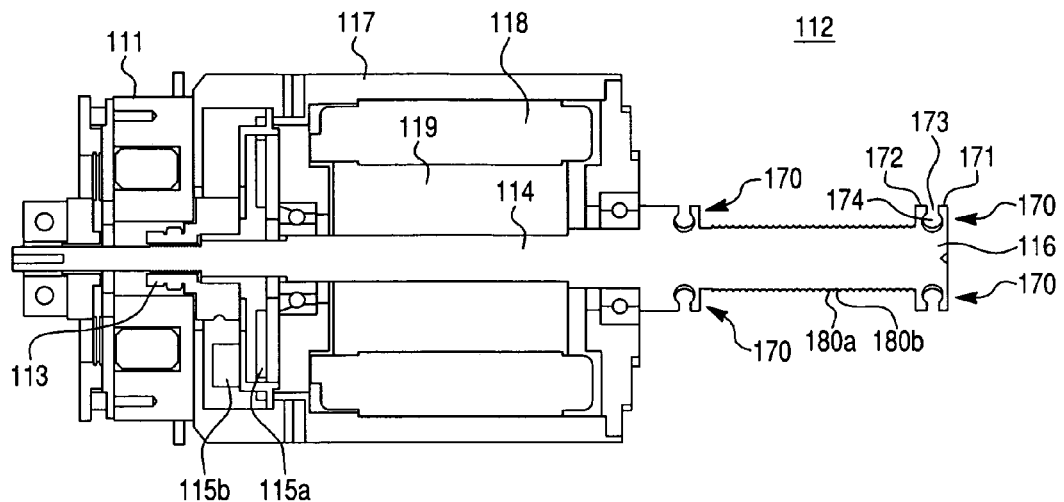
FIG. 7A is a cross-sectional view of an embodiment of a drive member of the joint assembly of FIG. 6.
Figure 7B:
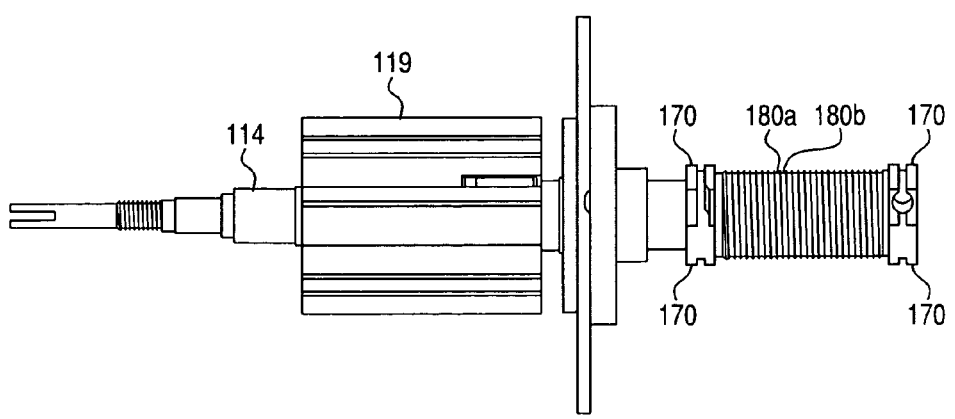
FIG. 7B is a side elevation view of an embodiment of a motor shaft and pinion of the joint assembly of FIG. 6.
Figure 8A:
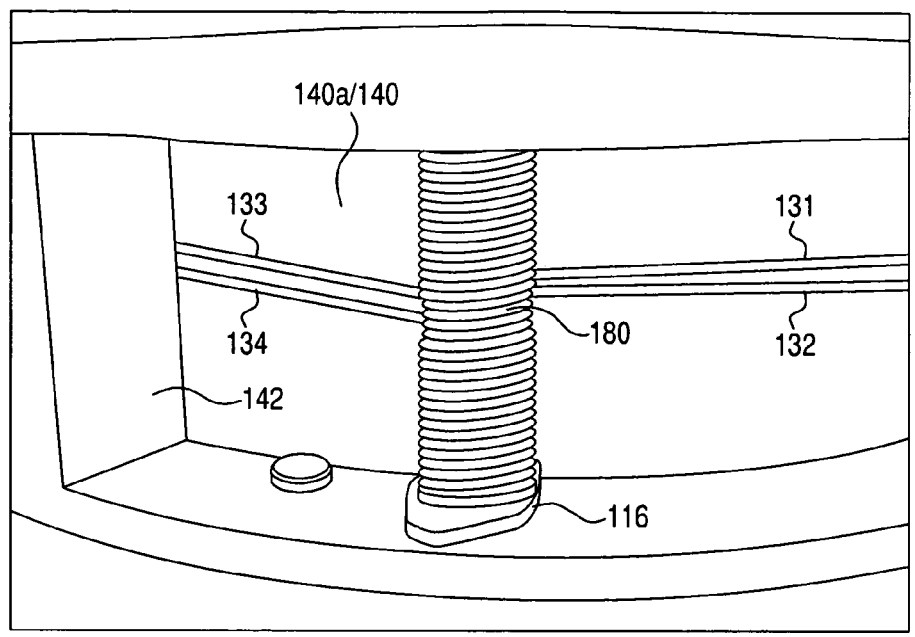
FIG. 8A is an elevation view of an embodiment of a flexible transmission coupled to a drive member of the joint assembly of FIG. 6.
Figure 8B:
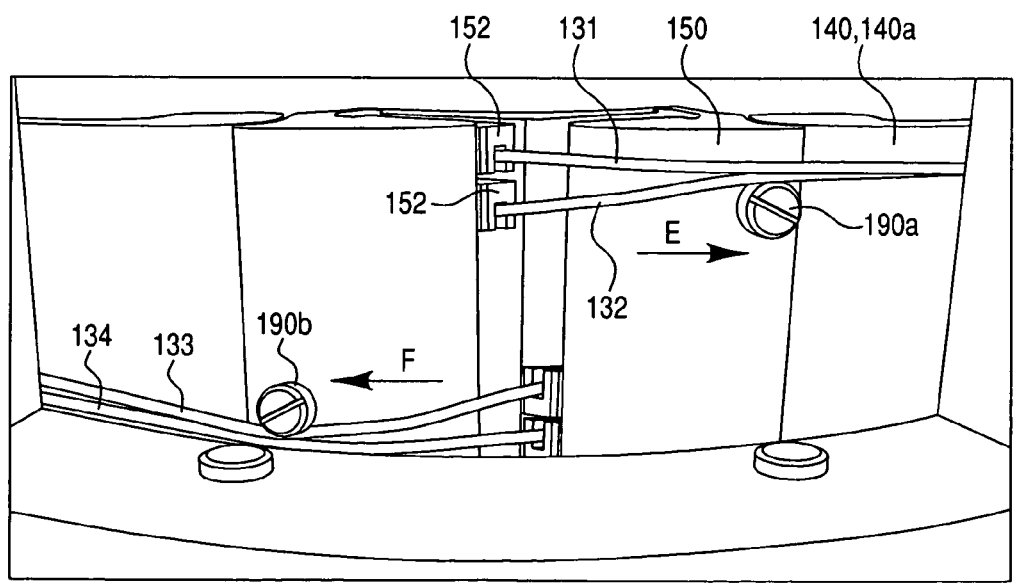
FIG. 8B is an elevation view of an embodiment of a flexible transmission coupled to a connection mechanism of the joint assembly of FIG. 6.

Rotation of the riser assembly 142 is driven by the drive member 110. In this embodiment, the drive member 110 includes a drive motor 112 that is disposed on the riser assembly 142 and thus moves with the riser assembly 142 as the riser assembly 142 rotates. To cause the riser assembly 142 to rotate, the drive motor 112 includes a motor shaft 114 having a pinion 116 extending therefrom, as shown in FIGS. 7A and 7B. The pinion 116 is configured to engage the flexible transmission 103. For example, each of the cables 131, 132, 133, 134 has a proximal end connected to and wound around the pinion 116 and a distal end connected to the main drive 140. The main drive 140 is disposed within the riser assembly 142 and is rigidly fixed to the baseplate 144. Thus, the main drive 142 is stationary relative to the baseplate 144 whereas the riser assembly 142 rotates relative to the baseplate 144. As shown in FIGS. 8A and 8B, the first and second cable sets extend from the pinion 116 in opposite directions around the main drive 140 and connect to the main drive 140 at the connection mechanism 150. When the drive motor 112 is actuated, the pinion 116 rotates causing the first cable set to wind around (or unwind from) the pinion 116 and the second cable set to conversely unwind from (or wind around) the pinion 116 depending on the direction of rotation. Because the distal ends of the cables 131, 132, 133, 134 are connected to the main drive 140 and the main drive 140 is stationary relative to the riser assembly 142, the winding and unwinding of the cables 131, 132, 133, 134 exerts force and/or torque on the riser assembly 142 that causes the riser assembly 142 to rotate around the main drive 140 thereby providing the first rotational degree of freedom J1 shown in FIG. 2. In this manner, the first and second transmission elements are configured to cause movement of the first component 101 in response to movement of the drive member 110.

Preferably, the joint output (in this case, the riser assembly 142, which is the driven member 120) includes a joint encoder configured to measure angular rotation of the joint output. In one embodiment, the joint encoder includes an encoder scale 160 that rotates with the riser assembly 142 and an encoder read head 162 that reads the encoder scale 160 (see FIG. 6). Although any suitable encoder system can be used, in this embodiment, the joint encoder is a tape scale type encoder system. When using a tape scale type encoder system in a rotary application, the circularity of the mounting surface to which the encoder scale 160 is affixed is important for obtaining accurate encoder readings. To ensure sufficient circularity, the encoder scale 160 is preferably mounted to an outside diameter or periphery of the cross roller bearing 146, where the outside diameter is precision ground (e.g., with a run-out tolerance of less than 11 micrometers) after assembly of the cross roller bearing 146. The encoder scale 160 can be attached to the cross roller bearing 146 using, for example, a pressure sensitive adhesive. To prevent delamination of the encoder scale 160 from the cross roller bearing 146, ends of the encoder scale 160 can be fixed under a tape scale clamp (not shown) that clamps the ends to the cross roller bearing 146, for example, using a screw fastener. The encoder read head 162 is mounted on the baseplate 144 so as to have a line of sight to the encoder scale 160. As the riser assembly 142 and outer race of the cross roller bearing 146 rotate, the encoder read head 162 reads the encoder scale 160 to determine relative angular position of the riser assembly 142. Because the joint encoder is a relative, as opposed to an absolute, encoder system, the joint encoder also includes an encoder index mark (not shown) disposed on the riser assembly 142. The encoder index mark includes a magnet that provides a fixed reference, or index mark, for the joint encoder so the robotic arm 10 knows the rotational location of the joint output relative to a known index location. Advantageously, the joint encoder enables rotational output of the joint output to be measured. As discussed further below, the rotational output can be compared to the rotational input from the drive motor 112 to evaluate the integrity of the flexible transmission 103.

As noted above, the drive member 110 includes a drive motor 112 (or actuator) that imparts rotational motion to the driven member 120 via the flexible transmission 103. The drive motor 112 may be any motor suitable for driving the driven member. In one embodiment, the drive motor 112 is a brushless DC permanent magnet motor, although the drive motor 112 could also be a brush-type motor or other motor technology. As shown in FIGS. 7A and 7B, in this embodiment, the drive motor 112 includes a housing 117, a stator 118 bonded to the housing 117, and a rotor 119 bonded to the motor shaft 114. The motor shaft 114 is supported in the housing 117 by motor bearings, such as angular contact ball bearings or any appropriate bearing that reduces friction and permits free rotation of the motor shaft 114 relative to the housing 117. A jam nut and lock nut (collectively 113) thread onto the motor shaft 114 to draw the motor shaft 114 through the housing 117 until axial clearance in the motor bearings is taken up. As a result, the motor bearings are pre-loaded, which eliminates axial and radial play of the motor shaft 114 relative to the housing 117. The jam nut prevents loosening of the lock nut over time (e.g., due to vibration).

Preferably, the drive motor 112 includes a motor encoder configured to measure angular rotation of the motor shaft 114. Similar to the joint encoder, the motor encoder includes an encoder scale 115a that rotates with the motor shaft 114 and an encoder read head 115b that reads the encoder scale. In one embodiment, the encoder scale 115a is a circular glass scale with fine pitch marks etched in the glass. The encoder scale 115a is bonded to a precision hub that is attached to the motor shaft 114. As shown in FIG. 7A, the encoder read head 115b is mounted so as to have a line of sight to the encoder scale 115a. As the motor shaft 114 and encoder scale 115a rotate, the encoder read head 115b reads the pitch marks on the encoder scale 115a to determine relative angular position of the motor shaft 114. Thus, the motor encoder enables measurement of the rotation of the motor shaft 114. As a result, the angular rotational input provided by the drive motor 112 (measured by the motor encoder) can be compared to the angular rotational output of the joint output (measured by the joint encoder). The rotational output should be proportional to the rotational input multiplied by the inverse of the drive ratio (drive reduction) of the first joint assembly 100. A discrepancy between the rotational input and output may indicate a problem with the flexible transmission 103 and can be used to trigger a fault in the robotic arm 10 that alerts the user of the discrepancy, places the robotic arm 10 in a safe mode and/or causes other precautionary action to be taken. Problems that might cause a discrepancy include failure of a cable, a cable tensioning mechanism, a transmission element such as a pinion or pulley, and the like. Advantageously, the combined use of motor and joint encoders contributes to overall failsafe operation of the robotic arm 10.

In an exemplary embodiment, the drive motor 112 includes a portion configured to be actuated to inhibit movement of the drive member, such as a motor brake 111, as shown in FIG. 7A. The motor brake 111 may be any suitable motor brake assembly, such as a brake assembly manufactured by The Carlyle Johnson Machine Company LLC, Bolton, Conn. The motor brake 111 includes a rotor affixed to the motor shaft 114 and a brake body attached to the motor housing 117 via an end cap. If power is applied to the motor brake 111, the brake rotor is free to rotate and the motor shaft 114 and pinion 116 can turn freely. If power is removed from the motor brake 111, the brake rotor, which is rigidly attached to the motor shaft 114, is constrained from rotating, which inhibits movement of the motor shaft 114 and pinion 116. The motor brake 111 can be engaged, for example, in response to a fault signal, such as a fault signal indicating a discrepancy between the rotational input and output of the first joint assembly 100.

Figure 34:
FIG. 34 is a schematic of a double connector tension element according to an embodiment.

The motor shaft 114 of the drive motor 112 is connected to (e.g., coupled to or integral with) the pinion 116. As noted above, the pinion 116 is configured to engage the flexible transmission 103. In one embodiment, the drive member 110 includes a first interface configured to removably secure the first transmission element and a second interface configured to removably secure the second transmission element. The first and second interfaces may be attachment elements 170. For example, the pinion 116 can include an attachment element 170 for each of the cables 131, 132, 133, 134. The attachment element 170 is a point of attachment for securing the proximal end of a cable to the pinion 116. The attachment element 170 may have any configuration suitable for securely anchoring a cable to the pinion 116. In one embodiment, the proximal end of the cable has a connector 4 (such as a stainless steel or brass ball as shown in FIG. 34) swaged thereto, and the attachment element 170 is configured to seat the connector 4 when the cable is under tension. For example, as shown in FIGS. 7A and 7B, the attachment element 170 includes an outer leg 171 and an inner leg 172 extending radially from the pinion 116 and forming an aperture 173. One side of the aperture 173 has a contoured opening 174 large enough to receive the connector 4 with the remaining portion of the aperture 173 being wide enough to receive the cable but not wide enough to permit the connector 4 to pass through the aperture 173. When the connector 4 is fitted into the contoured opening 174, the cable is passed through the aperture 173, and tension is applied to the cable in a direction away from the connector 4, the connector 4 seats into the contoured opening 174. As long as sufficient tension is maintained on the cable, the connector 4 remains seated. The cable can be decoupled from the attachment element 170 by releasing sufficient tension from the cable.

As shown in FIGS. 7B and 8A, the portion of a cable that exits an attachment element 170 engages a guide 180 (individual guides are shown as 180a and 180b). The guide 180 is configured to locate the cable on the pinion 116 and to direct and orient the cable. In one embodiment, the guide 180 comprises a groove (or channel) cut into the pinion 116. Preferably, the groove is a spiral (e.g., helical) groove that extends along a length of the pinion 116. The guide 180 receives the cable and, as the cable winds around the pinion 116, locates and constrains the cable. As shown in FIGS. 8A and 8B, each cable eventually leads off the pinion 116 and wraps around a portion of the main drive 140 before terminating at the connection mechanism 150 located on the main drive 140.

Preferably, the pinion 116 is configured to secure and guide each of the cables 131, 132, 133, 134 in the manner described above. In particular, the pinion 116 includes an attachment element 170 for each of the cables 131, 132, 133, 134. Two attachment elements 170 are disposed on a proximal end of the pinion 116 for interconnection with the cables 131, 132, and two of the attachment elements 170 are disposed on a distal end of the pinion 116 for interconnection with the cables 133, 134. In this embodiment, the pinion 116 includes two guides, where two of the cables share one guide and the other two cables share the other guide. In particular, the drive member 110 includes first and second guides 180a, 180b configured to position the first and second transmission sub-elements (i.e., the cables 131, 132) relative to the drive member 110. The first and second guides 180a, 180b are also configured to position the third and fourth transmission sub-elements (i.e., the cables 133, 134) relative to the drive member 110. For example, as shown in FIGS. 7B and 8A, the first guide 180a is configured to locate the cable 131 and the second guide 180b is configured to locate the cable 132 (or vice versa), where the cables 131, 132 are secured to the proximal end of the pinion 116. Similarly, the first guide 180a is configured to locate the cable 133 and the second guide 180b is configured to locate the cable 134 (or vice versa), where the cables 133, 134 are secured to the distal end of the pinion 116. Preferably, the first and second guides 180a, 180b extend along the length of the pinion 116 (i.e., the drive member 110) and are adjacent one another along the length of the pinion 116. For example, the first guide 180a is a first helical groove (or channel) and the second guide 180b is a second helical groove (or channel). These adjacent helical grooves form a "double helix" arrangement. As a result, as shown in FIG. 8A, the cables 131, 132 are disposed adjacent one another as they wind around the pinion 116 from the proximal end toward the distal end. Similarly, the cables 133, 134 are disposed adjacent one another as they wind around the pinion 116 from the distal end toward the proximal end. In this embodiment, the first and second guides 180a, 180b are congruent in size and shape.

The attachment element and guide embodiments described above are exemplary. As will be apparent to one of skill in the art, the drive member 110 could include alternative designs for attaching and guiding the cables. One advantage of using adjacent helical grooves (or a "double helix" arrangement), however, is that such an arrangement enables the flexible transmission 103 to include two sets of cables compactly packaged on a single pinion 116, where each cable set includes redundant cables (i.e., more than one cable performing the same function). For example, the cables 131, 132 are redundant because each cable 131, 132 performs the same function of exerting a tension force on the main drive 140 in a direction E when the pinion 116 rotates to wind the cables 131, 132 onto the pinion 116. Similarly, the cables 133, 134 are redundant because each cable 133, 134 performs the same function of exerting a tension force on the main drive 140 in a direction F when the pinion 116 rotates to wind the cables 133, 134 onto the pinion 116. One advantage of redundancy is that even if one cable in a cable set fails (e.g., the cable 131), the second cable (e.g., the cable 132) continues to transmit force and/or torque from the drive member 110 and thereby maintains control of the robotic arm 10. Thus, redundant tension elements are a failsafe feature to ensure that failure of a single tension element will not result in an uncontrolled joint output. This is particularly advantageous in surgical applications where malfunction of the robotic arm 10 during surgery could create a potentially dangerous condition for the patient. Additionally, use of a second cable may increase coupling stiffness, which advantageously increases haptic stiffness.

Another advantage of failsafe redundant tension elements is that using redundant tension elements in combination with a braked drive member (e.g., the drive motor 112 with the motor brake 111) enables the use of an unbraked driven member, meaning that the driven member 120 (i.e., the riser assembly 140, which is the joint output) does not have a brake mechanism. A joint brake can be omitted because the drive member 110 incorporates a brake and failure of a single tension element in a redundant tension element set will not result in uncontrolled joint output. As a result, motion of the first joint assembly 100 can be adequately controlled even if one tension element fails so there is no need to be able to independently brake the joint output. Omitting a joint brake improves performance of the robotic arm 10 because problems associated with conventional joint brakes are eliminated. In particular, a joint brake imparts high gravity and inertia loads on the joint assembly, which adversely impacts backdrivability and haptic response. Replacing a joint brake with a smaller brake on the drive member 110 and redundant tension elements advantageously decreases weight and inertia and improves backdrivability and haptic response.

Figure 9A:
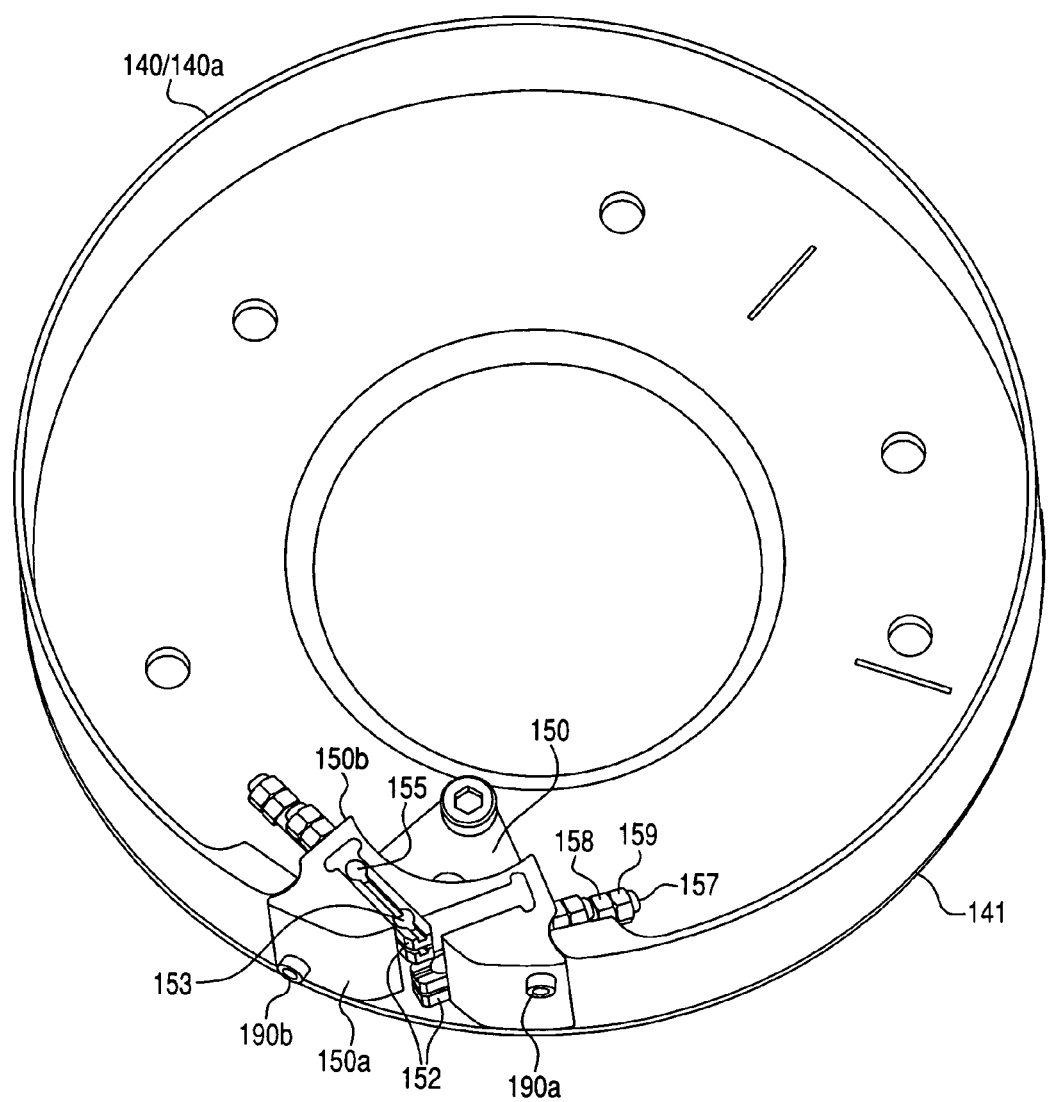

As shown in FIGS. 8A and 8B, the first and second cable sets extend from the pinion 116 in opposite directions around the main drive 140 and connect to the main drive 140 at the connection mechanism 150. Although the connection mechanism 150 is disposed on the main drive 140, which is a stationary component of the first joint assembly 100, it will be apparent to those of skill in the art that the connection mechanism 150 could also be used on a moving member, such as a rotating pulley. For ease of reference, the main drive 140 will be referred to as a pulley 140a. Although the pulley 140a of this embodiment is stationary, in other embodiments, the pulley 140a could be rotating. The connection mechanism 150 may be integral with the pulley 140a or coupled to the pulley 140a, for example, with mechanical fasteners. As shown in FIG. 9A, in one embodiment, the connection mechanism 150 includes, relative to the pulley 140a, an outwardly facing portion 150a and an inwardly facing portion 150b. The outwardly facing portion 150a forms a portion of a circumferential perimeter 141 of the pulley 140a and provides an access interface for the cables. For example, for each cable 131, 132, 133, 134, the connection mechanism 150 includes a coupling member 152 configured to receive a distal end of the cable. The coupling member 152 may have any configuration suitable for securely anchoring the cable. In one embodiment, the distal end of the cable has a connector 4 (such as a stainless steel or brass ball as shown in FIG. 34) swaged thereto, and the coupling member 152 includes an angled spherical pocket 153 (or groove) for receiving and securely seating the connector 4 when the cable is under tension. As long as sufficient tension is maintained on the cable, the connector 4 remains seated. The cable can be decoupled from the coupling member 152 by releasing sufficient tension from the cable. In a preferred embodiment (shown in FIG. 9B), the coupling member 152 includes a single pocket 153 for securing the distal end of the cable. Alternatively, the coupling member 153 may be configured to secure a tension element in at least a first location and a second location. For example, the coupling member may include multiple pockets 153, 155 (shown in FIG. 9A) to enable the end of the cable to be secured in a first location or a second location depending, for example, on the length of the cable.

The connection mechanism 150 preferably includes one or more slots configured to receive the coupling members 152. For example, as shown in FIG. 9B, the connection mechanism 150 includes a first slot 156a and a second slot 156b. The coupling members 152 received in the first slot 156a secure the first set of cables (i.e., the cables 131, 132) which extend in a first direction (i.e., the direction E) from an upper portion of the connection mechanism 150, and the coupling members 152 received in the second slot 156b secure the second set of cables (i.e., the cables 133, 134) which extend in a second direction (i.e., the direction F) from a lower portion of the connection mechanism 150. The first and second slots 156a, 156b are preferably offset from one another by a predetermined angle $\alpha$ (based, for example, on a diameter of the pulley 140a so that the incoming cables are appropriately oriented in the directions E, F. For example, in the embodiment of FIGS. 9A and 9B, the predetermined angle is about 110 degrees. Thus, the first direction is offset from the second direction by the predetermined angle $\alpha$. Once a coupling member 152 is inserted into a slot 156a, 156b, the coupling member 152 can be moved within the slot 156a, 156b to a desired location and then fixed in the slot 156a, 156b using any suitable mechanism. In an exemplary embodiment, the coupling member 152 is fixed in the slot 156a, 156b using a threaded rod 157 that also functions as an adjustment member for adjusting the connection mechanism 150 to vary a tension force applied to the flexible transmission 103. For example, as shown in FIG. 9B, the coupling member 152 is connected to one end of the threaded rod 157, and the other end of the threaded rod 157 includes a tension nut 158, a lock nut 159, and an optional spacer 151 that extend into the interior of the pulley 140a. Thus, the adjustment member is disposed at least partially inwardly of the circumferential perimeter 141 of the pulley 140a. After the distal end of the cable is seated in the coupling member 152, a tension force is applied to the cable by tightening the tension nut 158 until the cable tension reaches a desired value. The lock nut 159 is then tightened to prevent the tension nut 158 from loosening over time (e.g., due to vibration). Tightening or loosening the tension nut 158 adjusts the cable tension accordingly. The optional spacer 151 is useful for positioning the tension and lock nuts 158, 159 so they are easily accessible by manufacturing and service personnel. In this manner, the connection mechanism 150 is configured to be adjusted to vary a tension force applied to the flexible transmission 103. In particular, the connection mechanism 150 is configured to be adjusted to independently vary a tension force applied to each of the plurality of tension elements (i.e., the cables 131, 132, 133, 134). Advantageously, the coupling member 152 is configured to inhibit rotation of the coupled cable when the connection mechanism 150 is adjusted to vary the tension force applied to the flexible transmission 103. In particular, because the coupling member 152 is constrained in the slot 156a, 156b, the coupling member 152 will not rotate, and thus prevents rotation of the cable, when the tension nut 158 is adjusted to vary the tension force applied to the cable.

The connection mechanism 150 may also include a guide member configured to position the distal ends of the cables of a cable set in a desired manner. In particular, the guide member maintains proper leads of the cables from the connection mechanism 150 back to the pinion 116. For example, as shown in FIG. 8B, a guide member 190a gathers the cables 131, 132 of the first cable set together a short distance from where the cables 131, 132 exit the connection mechanism 150. Preferably, the guide member 190a gathers the cables 131, 132 at a position where the distal ends of the cables 131, 132 are appropriately aligned with the proximal ends of the cables 131, 132 leading off the pinion 116. The connection mechanism 150 can also include a second guide member 190b to similarly gather and guide the cables 133, 134 of the second cable set. In particular, it is desirable to position the distal ends of the cables so the proximal ends of the cables coming off the pinion 116 maintain a substantially square or perpendicular relationship to the pinion 116 to avoid unwanted effects, such as grinding. In one embodiment, for example, the guide member 190a is configured to maintain a portion of the cable 131 (i.e., the first transmission sub-element) substantially parallel to a portion of the cable 132 (i.e., the second transmission sub-element), as shown in FIG. 8B, so the distal end of one (or both) of the cables 131, 132 does not pull the proximal end of that cable in an unwanted direction. Similarly, the second guide member 190b can be configured to maintain a portion of the cable 133 (i.e., the third transmission sub-element) substantially parallel to a portion of the cable 134 (i.e., the fourth transmission sub-element). The guide members 190a, 190b may be any device suitable for guiding the cables. In the embodiment of FIG. 8B, the each guide member 190a, 190b includes a threaded pin removably fastened to the connection mechanism 150. To avoid chafing the cables, the guide members 190a, 190b can be configured such that there is substantially no relative motion between the guide member 190a, 190b and the associated cables in response to movement of the drive member 110. This can be accomplished, for example, by disposing the guide members 190a, 190b remotely from the drive member 110. For example, as shown in FIG. 8B, the guide members 190a, 190b can be disposed directly on the connection mechanism 150 in close proximity to the point where the cables engage the coupling members 152.

Second Joint Assembly

FIGS. 5A to 5E show the second joint assembly 200 according to an embodiment of the invention. The second joint assembly 200 is disposed on the joint output (i.e., the riser assembly 142) of the first joint assembly 100 and thus moves with the joint output of the first joint assembly 100. The second joint assembly 200 includes a first component 201, a second component 202, and an at least partially flexible transmission 203. In this embodiment, the first component 201 includes a drive member 210, and the second component 202 includes a driven member 220. The flexible transmission 203 is coupled to the drive member 210 and the driven member 220 and is configured to move the driven member 220 in response to motion of the drive member 210.

The flexible transmission 203 of the second joint assembly 200 is similar to the flexible transmission 103 of the first joint assembly 100 and includes first and second transmission elements that comprise first and second cable sets, respectively. The first cable set includes a first cable 231 and a second cable 232, and the second cable set includes a third cable 233 and a fourth cable 234. Thus, the second joint assembly 200 includes redundant cables the advantages of which are described above in connection with the first joint assembly 100. For example, the cables 231, 232 are redundant because each cable 231, 232 performs the same function of exerting a tension force on the driven member 220 in a direction G (shown in FIG. 5C) when a pinion 216 of the drive member 210 rotates to wind the cables 231, 232 onto the pinion 216. Similarly, the cables 233, 234 are redundant because each cable 233, 234 performs the same function of exerting a tension force on the driven member 220 in a direction H when the pinion 216 rotates to wind the cables 233, 234 onto the pinion 216. In this manner the first tension element (e.g., the cables 231, 232) is configured to cause movement of the driven member 220 in a first direction (e.g., the direction G) in response to a first movement of the drive member 210, and the second tension element (e.g., the cables 233, 234) is configured to cause movement of the driven member 220 in a second direction (e.g., the direction H) in response to a second movement of the drive member 210. The cables 231, 232, 233, 234 may be any cables appropriate for use in a robotic system but are preferably tungsten cables. Although the cables 231, 232, 233, 234 can be configured in a variety of ways to impart motion to the driven member 220, in this embodiment, each of the cables 231, 232, 233, 234 has a proximal end connected to the drive member 210 (i.e., the first component 201) and a distal end connected to the driven member 220 (i.e., the second component 202).

Figure 5A:
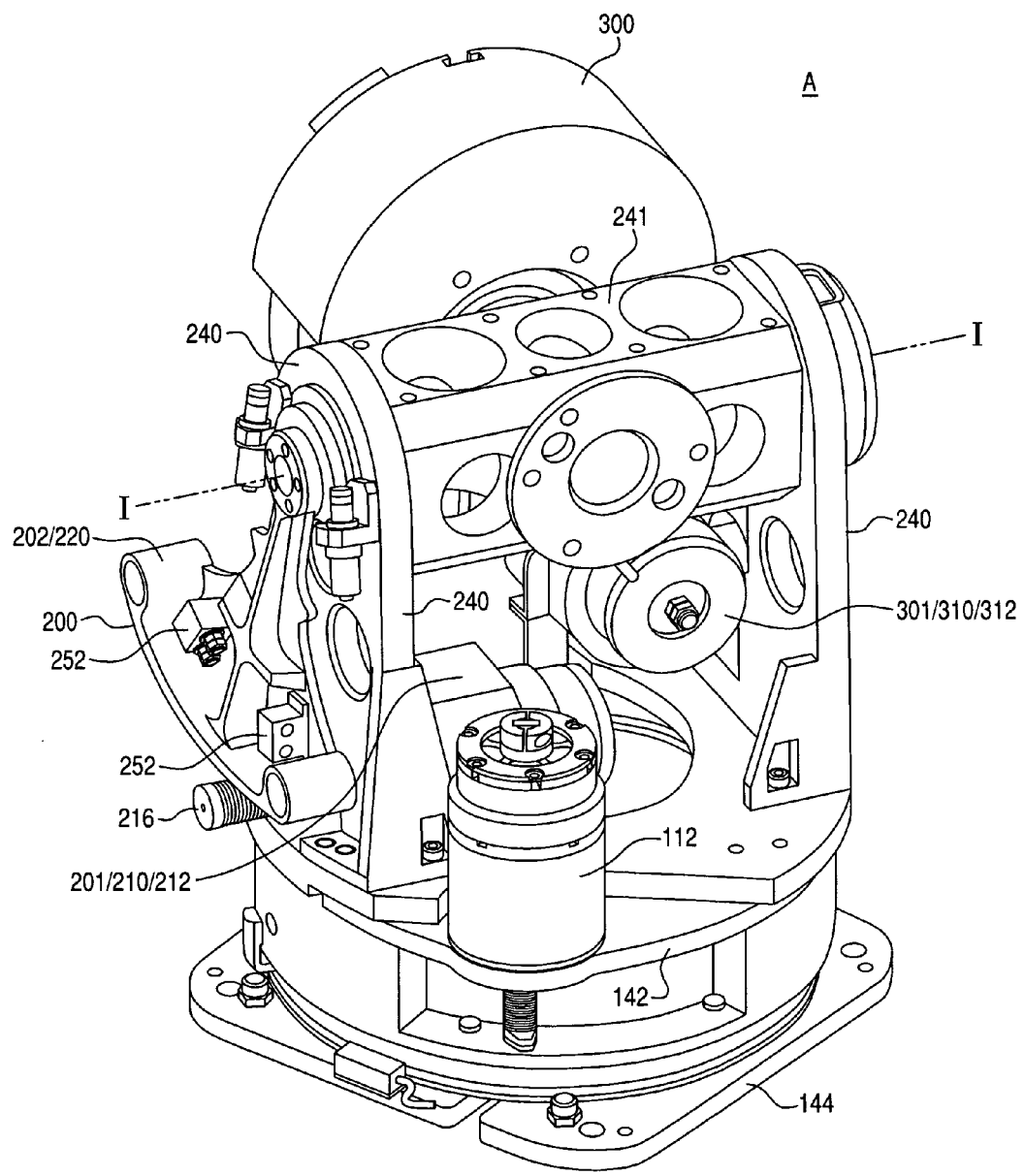
FIG. 5A is a front perspective view of an embodiment of a first module of the robotic arm of FIG. 2.
Figure 5B:
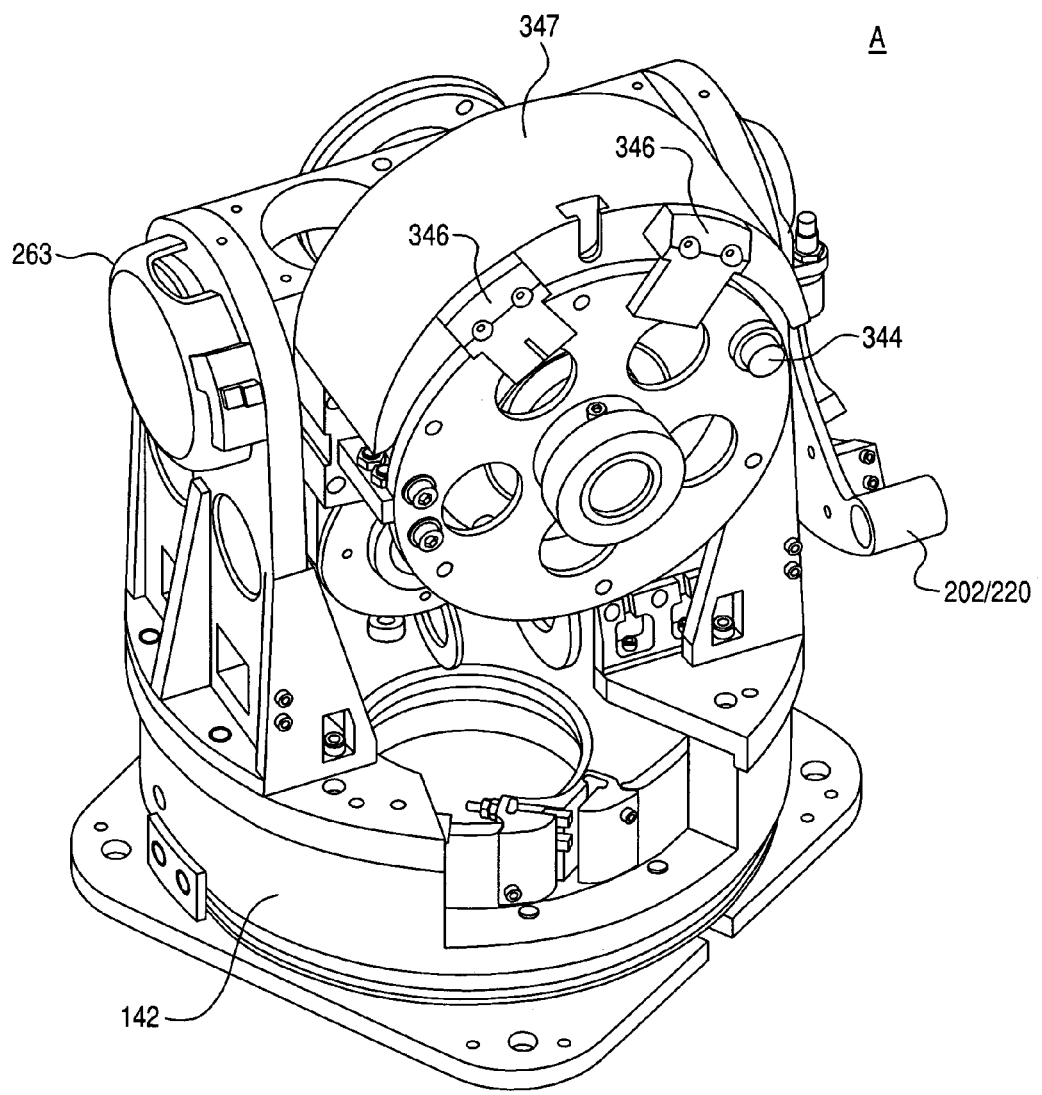
FIG. 5B is a rear perspective view of the first module of FIG. 5A.

According to an embodiment, the driven member 220 of the second joint assembly 200 is coupled to the joint output of the first joint assembly 100, and rotation of the driven member 220 is driven by the drive member 210 via the cables 231, 232, 233, 234. For example, as shown in FIG. 5A, supports 240 are rigidly attached to the riser assembly 142 and include bearings that support a main shaft 241. The main shaft 241 is the joint output of the second joint assembly 200 and is coupled to (or integral with) the driven member 220. For example, the driven member 220 is rigidly attached to the main shaft 241 using mechanical fasteners (e.g., screws) and is also pinned to provide a secondary form of attachment to mitigate the risk of the mechanical fasteners becoming loose. The driven member 220 is configured to rotate about an axis I-I in a pendulum-type motion, which results in rotation of the main shaft 241.

Figure 5C:
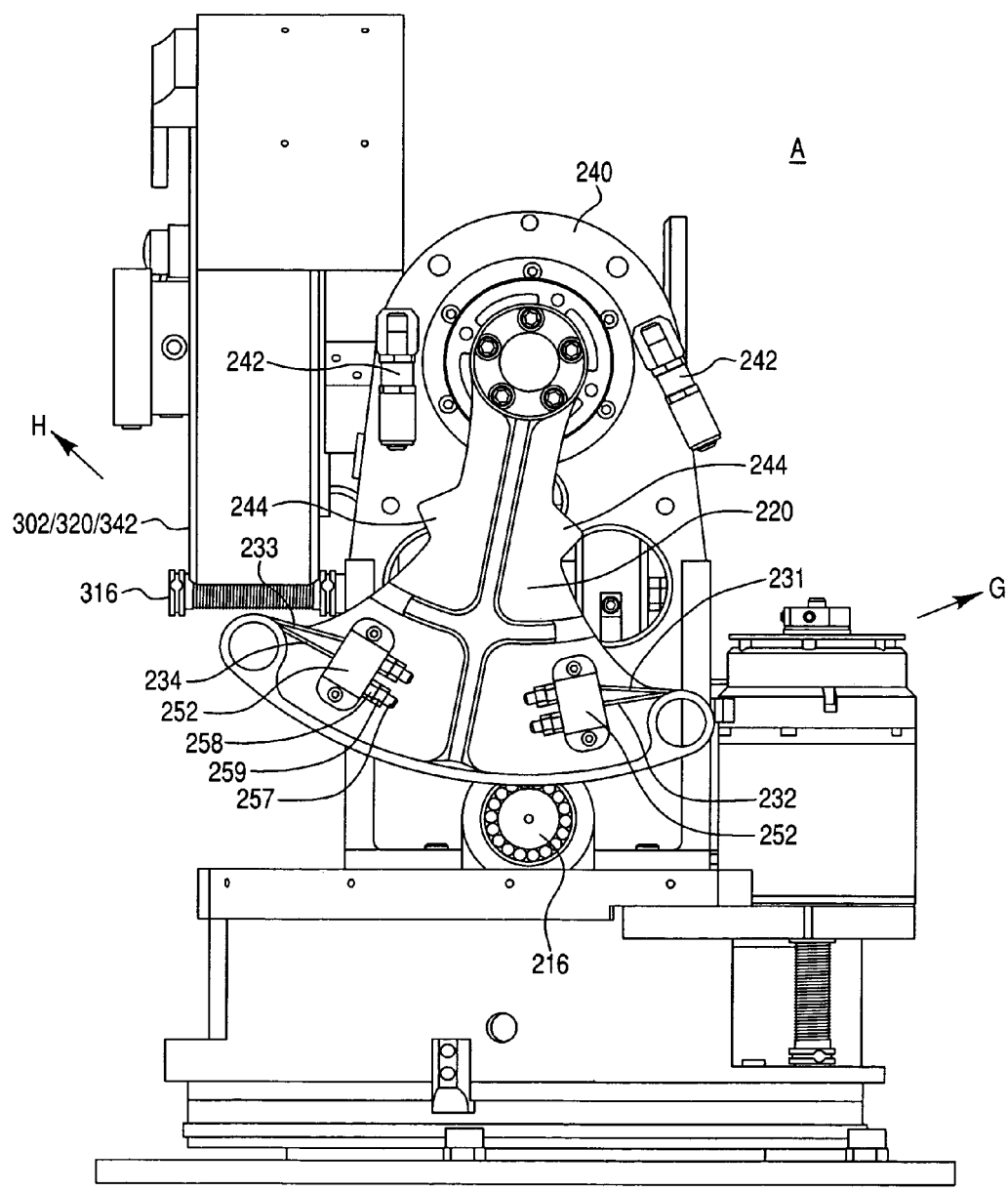
FIG. 5C is a right side elevation view of the first module of FIG. 5A.
Figure 5D:
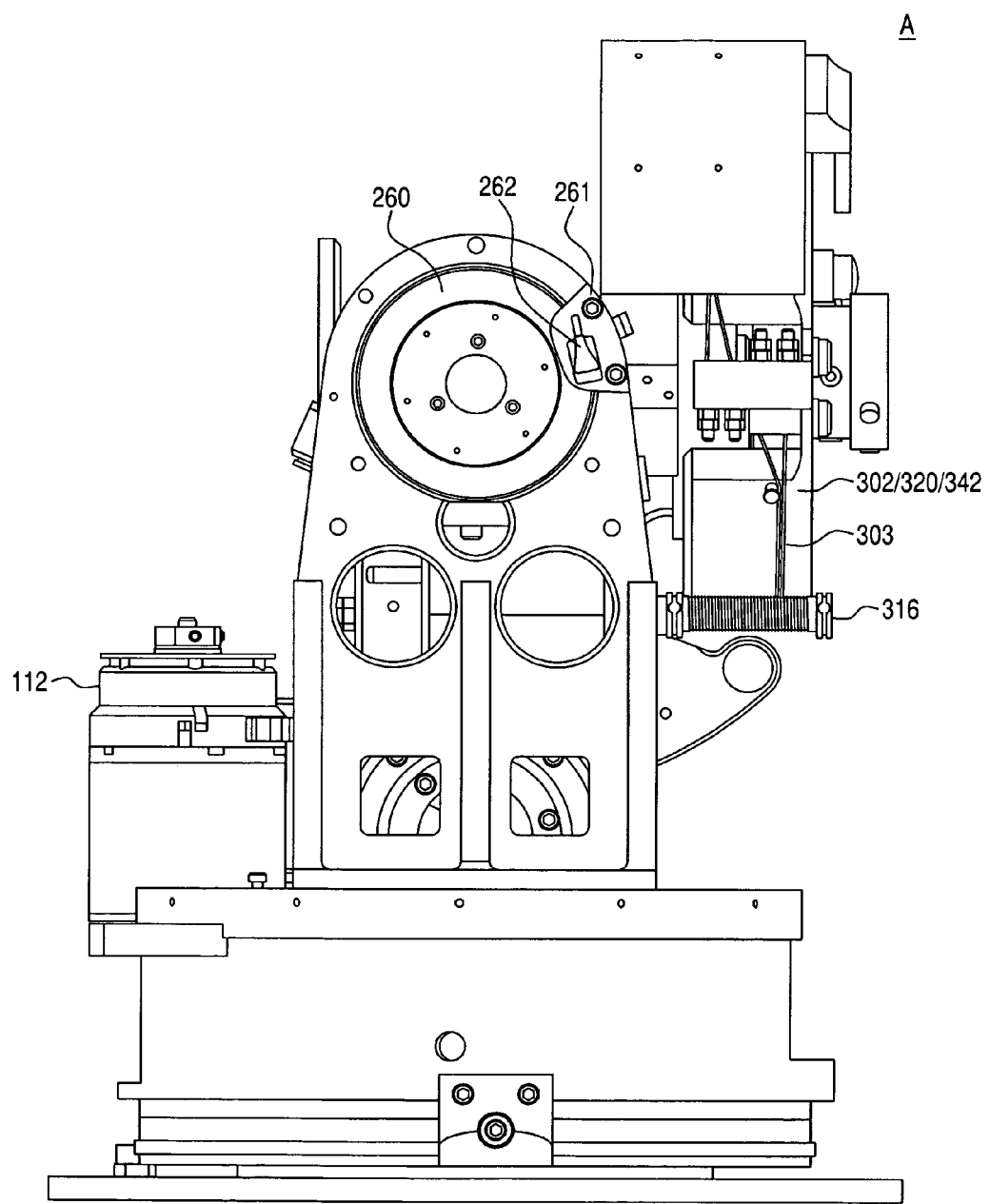
FIG. 5D is a left side elevation view of the first module of FIG. 5A.
Figure 5E:
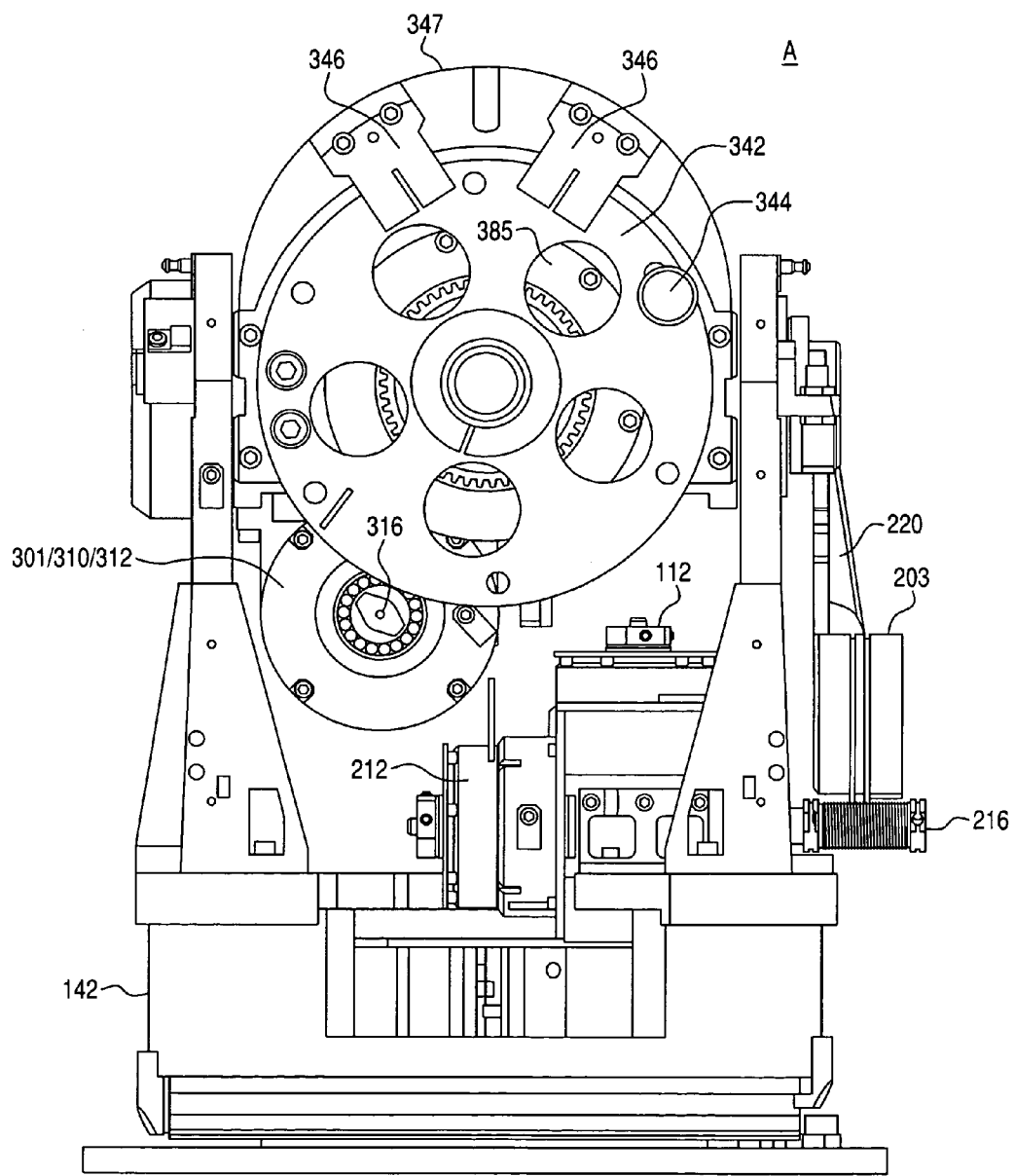
FIG. 5E is a rear elevation view of the first module of FIG. 5A

The drive member 210 includes a drive motor 212 that provides motive force to the driven member 220. The drive motor 212 may be any motor suitable for driving the driven member 220. Preferably, the drive motor 212 of the second joint assembly 200 is similar to the drive motor 112 of the first joint assembly 100 in all aspects, including the pinion, motor encoder, and motor brake, the advantages of which are described above in connection with the first joint assembly 100. As shown in FIG. 5A, the drive motor 212 is mounted to the riser assembly 142 and/or to one of the supports 240. Each of the cables 231, 232, 233, 234 has a proximal end connected to and wound around the pinion 216 in a manner identical to that described above in connection with the pinion 116 of the first joint assembly 100. As best seen in FIGS. 5C and 5E, the first and second cable sets extend from the pinion 216 in opposite directions, travel along an underside of the driven member 220, and then curve up and around the driven member 220 before terminating at a connection mechanism that includes two coupling components 252. A first tension element (e.g., the cables 231, 232) is coupled to one coupling component 252, and a second tension element (e.g., the cables 233, 234) is coupled to the other coupling component 252. When the drive motor 212 is actuated, the pinion 216 rotates causing the first cable set to wind around (or unwind from) the pinion 216 and the second cable set to conversely unwind from (or wind around) the pinion 216 depending on the direction of rotation. Because the distal ends of the cables 231, 232, 233, 234 are connected to the driven member 220, the winding and unwinding of the cables 231, 232, 233, 234 exerts force and/or torque on the driven member 220 that causes the driven member 220 (and thus the main shaft 241) to rotate thereby providing the second rotational degree of freedom J2 shown in FIG. 2. In this manner, the first and second transmission elements are configured to cause movement of the driven member 220 (i.e., the second component 202) in response to movement of the drive member 210.

To limit rotation of the driven member 220, end stop assemblies 242 are disposed on the support 240 and corresponding stop members 244 are disposed on the driven member 220. When rotation of the driven member 220 causes a stop member 244 to contact its corresponding end stop assembly 242, rotation of the driven member 220 is constrained. Preferably, the end stop assemblies 242 include shock absorbing features (e.g., shock absorbers, rubber mounts, or the like) and are adjustable in both length and angular orientation to enable the end stop assemblies 242 to be arranged in a desired alignment relative to the driven member 220 and to be adjusted.

Figure 10:
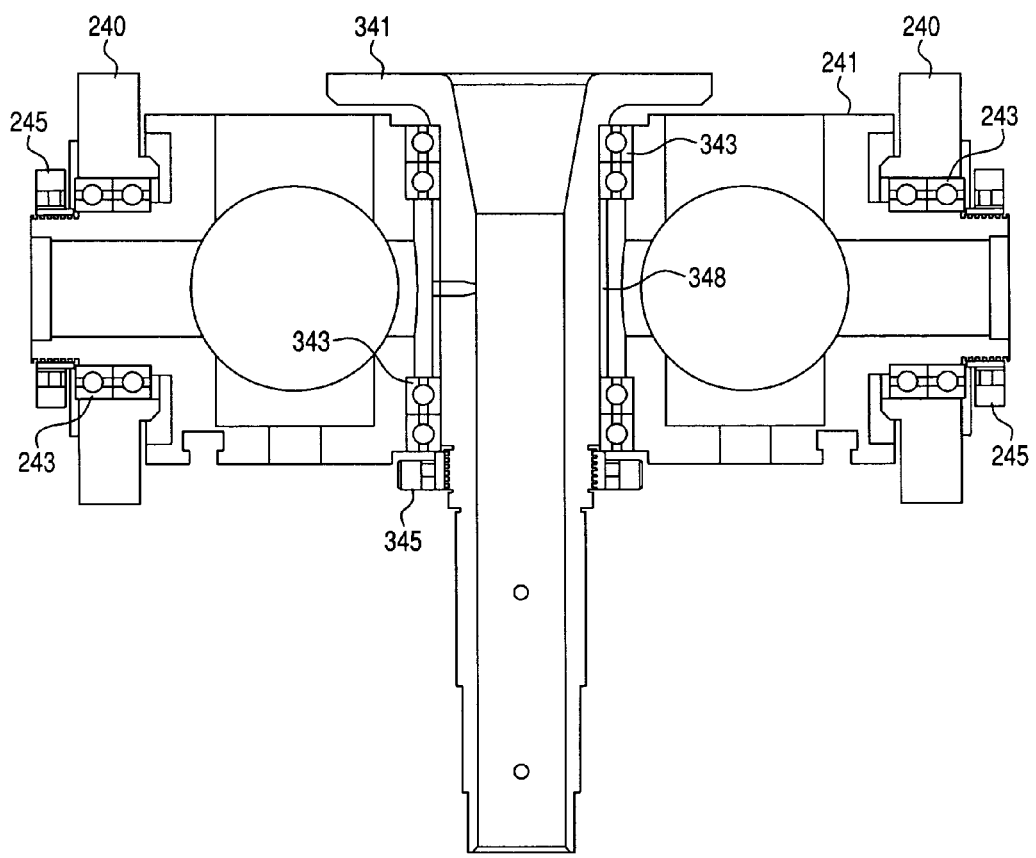
FIG. 10 is a cross-sectional view of an embodiment a joint output of a joint assembly of the first module of FIG. 5A.

To enable rotation of the main shaft 241 with low friction, bearings 243 that support the main shaft on the supports 240 are preferably duplex ball bearing pairs (shown in FIG. 10). The duplex ball bearing pairs are designed such that when the inner races of the duplex pair are pressed together axially with a preload force, the axial and radial play of the bearings 243 are removed. In the embodiment of FIG. 10, the inner races of each duplex ball bearing pair are mounted on a precision ground outside diameter of the main shaft 241 with a shoulder machined into the main shaft 241 to locate the duplex ball bearing pair axially on the main shaft 241. Threads on the outer ends of the main shaft 241 accept bearing preload nuts 245 that are tightened until the inner races of the duplex ball bearing pair are pressed together, preloading the bearings 243 to eliminate play while maintaining low rotational friction of the main shaft 241.

Preferably, the joint output (in this case, the main shaft 241) includes a joint encoder configured to measure angular rotation of the joint output. Any suitable encoder system can be used. In one embodiment, the joint encoder includes an encoder scale 260 that rotates with the main shaft 241 and an encoder read head 262 that reads the encoder scale 260. As shown in FIG. 5D, the encoder scale 260 is rigidly attached to an end of the main shaft 241 (e.g., using mechanical fasteners, adhesive, and/or the like), and the encoder read head 262 is fixedly mounted to the support 240 via a bracket 261 so as to have a line of sight to the encoder scale 260. The bracket 261 is configured to position the encoder read head 262 correctly relative to the encoder scale 260. As the main shaft 241 rotates, markings on the encoder scale 260 are read by the encoder read head 262 to determine angular position of the main shaft 241. For relative encoder systems, an encoder index mark (as described above in connection with the joint encoder of the first joint assembly 110) is also included. Preferably, the joint encoder is at least partially enclosed by a protective cover 263 (shown in FIG. 5B). Advantageously, the joint encoder enables rotational output of the joint output to be measured. As discussed above in connection with the first joint assembly 100, the rotational output can be compared to the rotational input from the drive motor 212 (measured by the motor encoder) to determine whether the integrity of the flexible transmission has been compromised.

As shown in FIGS. 5C and 5E, the first and second cable sets of the second joint assembly 200 extend from the pinion 216 in opposite directions and connect to the driven member 220 at the connection mechanism, which includes the coupling components 252. The coupling components 252 may be integral with or coupled to the driven member 220 and may have any configuration suitable for securely anchoring the cables. In one embodiment, the connection mechanism includes first and second coupling components (i.e., the two coupling components 252), where the second coupling component is disposed remotely from the first coupling component, as seen in FIG. 5C. In this embodiment, each coupling component 252 includes a machined block that is attached to the driven member 220 using one or more fasteners. The distal end of each cable 231, 232, 233, 234 includes a connector adapted to engage a threaded rod 257, and the machined block includes a through hole (for each cable) that receives the threaded rod 257. The threaded rod 257 is inserted into the appropriate through hole and secured in the machined block using a tension nut 258 and a lock nut 259 in a mariner identical to that described above in connection with the connection mechanism 150 of the first joint assembly 100.

In an exemplary embodiment, the connection mechanism (i.e., the coupling components 252) also functions as an adjustment member for varying a tension force applied to each cable. For example, a tension force is applied to a cable by tightening the associated tension nut 258 until the cable tension reaches a desired value in a manner identical to that described above in connection with the connection mechanism 150. Thus, the connection mechanism is a tensioning mechanism disposed on the driven member 220 (i.e., the second component 202) and configured to apply a tension force to the first transmission element (e.g., the cables 231, 232) and the second transmission element (e.g., the cables 233, 234) and to be adjusted to vary the tension force. Because the tensioning mechanism is located on the driven member 220 and thus moves with the driven member 220, it is referred to as a "floating" tensioner. In contrast, conventional cable tensioners are typically fixed to a stationary component. One advantage of using a floating tensioner is a more compact design. Additionally, a floating tensioner enables the use of shorter cables, which can result in a stiffer drive mechanism.

Third Joint Assembly

FIGS. 5A to 5E show the third joint assembly 300 according to an embodiment of the invention. The third joint assembly 300 is disposed on the joint output (i.e., the main shaft 241) of the second joint assembly 200 and thus moves with the joint output of the second joint assembly 200. The third joint assembly 300 includes a first component 301, a second component 302, and an at least partially flexible transmission 303. In this embodiment, the first component 301 includes a drive member 310, and the second component 302 includes a driven member 320. The flexible transmission 303 is coupled to the drive member 310 and the driven member 320 and is configured to move the driven member 320 in response to movement of the drive member 310.

The flexible transmission 303 of the third joint assembly 300 is similar to the flexible transmission 103 of the first joint assembly 100 and includes first and second transmission elements that comprise first and second cable sets, respectively. The first cable set includes a first cable 331 and a second cable 332, and the second cable set includes a third cable 333 and a fourth cable 334. Thus, the third joint assembly 300 includes redundant cables the advantages of which are described above in connection with the first joint assembly 100. For example, the cables 331, 332 are redundant because each cable 331, 332 performs the same function of exerting a tension force on the driven member 320 in a direction J (shown in FIG. 11) when a pinion 316 of the drive member 310 rotates to wind the cables 331, 332 onto the pinion 316. Similarly, the cables 333, 334 are redundant because each cable 333, 334 performs the same function of exerting a tension force on the driven member 320 in a direction K when the pinion 316 rotates to wind the cables 333, 334 onto the pinion 316. In this manner, a first tension element (e.g., the cables 331, 332) is configured to cause movement of the driven member 320 in a first direction (e.g., the direction J) in response to a first movement of the drive member 310, and a second tension element (e.g., the cables 333, 334) is configured to cause movement of the driven member 320 in a second direction (e.g., the direction K) in response to a second movement of the drive member 310. The cables 331, 332, 333, 334 may be any cables appropriate for use in a robotic system but are preferably tungsten cables. Although the cables 331, 332, 333, 334 can be configured in a variety of ways to impart motion to the driven member 320, in this embodiment, each of the cables 331, 332, 333, 334 has a proximal end connected to the drive member 310 and a distal end connected to the driven member 320.

According to an embodiment, the driven member 310 of the third joint assembly 300 is coupled to the joint output of the second joint assembly 200 (i.e., the main shaft 241), and rotation of the driven member 320 is driven by the drive member 310 via the cables 331, 332, 333, 334. For example, as shown in FIG. 10, an output shaft 341 of the third joint assembly 300 intersects and is disposed on the main shaft 241 of the second joint assembly 200 supported by bearings 343. The output shaft 341 is the joint output of the third joint assembly 300 and is coupled to (or integral with) the driven member 320. For example, in an exemplary embodiment, the driven member 320 is a pulley 342 that slides onto the output shaft 341 and is fixedly secured to the output shaft 341 by a clamp ring or collar. The pulley 342 (i.e., the driven member 320) is connected to the flexible transmission 303. When actuated by the drive member 310, the flexible transmission 303 causes the pulley 342, and thus the output shaft 341, to rotate.

Figure 11:
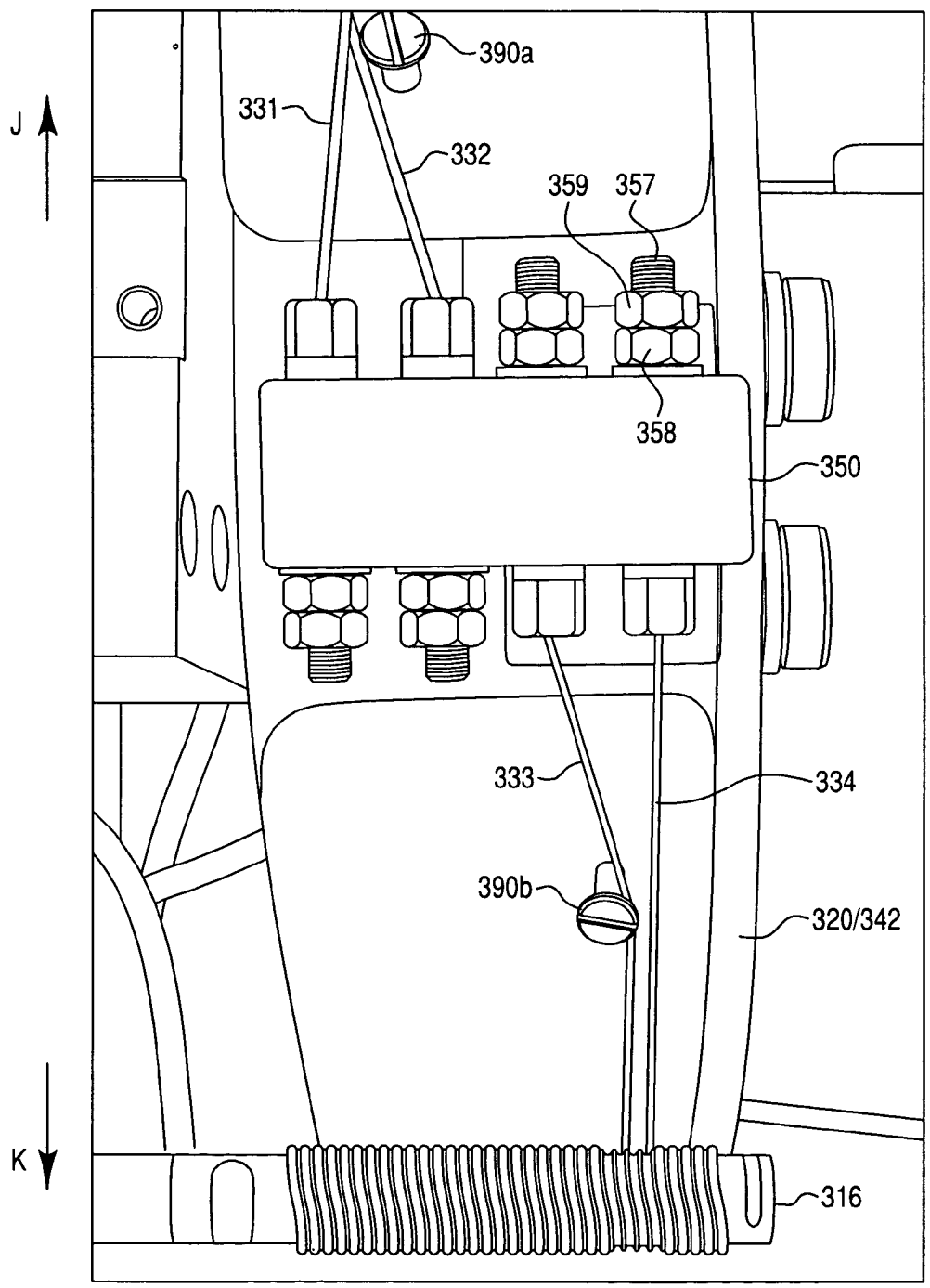
FIG. 11 is an elevation view of an embodiment of a flexible transmission coupled to a driven member of the first module of FIG. 5A.

The drive member 310 includes a drive motor 312 that provides motive force to the driven member 320. The drive motor 312 may be any motor suitable for driving the driven member 320. Preferably, the drive motor 312 of the third joint assembly 300 is similar the drive motor 112 of the first joint assembly 100, including the pinion and motor encoder, the advantages of which are described above in connection with the first joint assembly 100. The drive motor 312 is mounted on the main shaft 241. Each of the cables 331, 332, 333, 334 has a proximal end connected to and wound around the pinion 316 in a manner identical to that described above in connection with the pinion 116 of the first joint assembly 100. The first and second cable sets extend from the pinion 316 in opposite directions, travel around a portion of a circumference of the pulley 342, and terminate at a connection mechanism 350 disposed on the pulley 342. As shown in FIG. 11, the first and second cable sets engage the connection mechanism 350 on opposite sides. When the drive motor 312 is actuated, the pinion 316 rotates causing the first cable set to wind around (or unwind from) the pinion 316 and the second cable set to conversely unwind from (or wind around) the pinion 316 depending on the direction of rotation. Because the distal ends of the cables are connected to the pulley 342, the winding and unwinding of the cables 331, 332, 333, 334 exerts force and/or torque on the pulley 342 that causes the pulley 342 (and thus the output shaft 341) to rotate thereby providing the third rotational degree of freedom J3 shown in FIG. 2.

To limit rotation of the pulley 342, a bumpstop assembly 344 is disposed on the pulley 342 and stop members 346 are disposed on a counterbalance weight 347 that is mounted on the main shaft 341 (e.g., to counteract the weight of the joint assemblies 400, 500, 600). When rotation of the pulley 342 causes the bumpstop assembly 344 to contact a stop member 346, rotation of the pulley 342 (and thus the output shaft 341) is constrained.

To enable rotation of the output shaft 341 with low friction, the bearings 343 that support the output shaft 341 on the main shaft 241 are preferably duplex ball bearing pairs like those discussed above in connection with the main shaft 241 of the second joint assembly 200. The duplex ball bearing pairs are mounted in a similar fashion to the bearings 243 except the distance between the duplex ball bearing pairs is controlled by a spacer 348 that functions to translate preload force imparted by a bearing preload nut 345 to both duplex ball bearing pairs.

One difference between third joint assembly 300 and the first and second joint assemblies 100, 200 is that the drive motor 312 of the third joint assembly 300 does not include a motor brake. Instead, the third joint assembly 300 utilizes a joint brake 385 coupled directly to the joint output (i.e., the output shaft 341). The joint brake 385 may be any suitable brake assembly. In one embodiment, the joint brake 385 includes a stator that is connected to the counterbalance weight 347 and a rotor that is attached to the output shaft 341. The joint brake 385 can be actuated to constrain rotation of the output shaft 341 as appropriate, such as when a fault condition is triggered.

Preferably, the joint output (in this case, the output shaft 341) includes a joint encoder configured to measure angular rotation of the joint output. Any suitable encoder system can be used. In one embodiment, the joint encoder is disposed behind the joint brake 385 and is similar to the joint encoder of the second joint assembly 200 except an encoder scale (not shown) is attached to the output shaft 341 and an encoder read head (not shown) is attached to the main shaft 241. As the output shaft 341 rotates relative to the main shaft 241, the encoder read head reads the encoder scale. Advantageously, the joint encoder enables rotational output of the joint output to be measured. As discussed above in connection with the first joint assembly 100, the rotational output can be compared to the rotational input from the drive motor 312 (measured by the motor encoder) to determine whether the integrity of the flexible transmission has been compromised.

As noted above, the first and second cable sets of the third joint assembly 300 extend from the pinion 316 in opposite directions and connect to the pulley 342 (i.e., the driven member 320) at the connection mechanism 350. As best shown in FIG. 11, when connected, the cables 331, 332 (i.e., a first tension element) extend from a first side of the connection mechanism 350, and the cables 333, 334 (i.e., a second tension element) extend from a second side of the connection mechanism 350. The connection mechanism 350 may be integral with the pulley 342 or coupled to the pulley 342 (e.g., with mechanical fasteners) and may have any configuration suitable for securely anchoring the cables. In an exemplary embodiment, the connection mechanism 350 includes a machined block that is attached to the pulley 342 using one or more fasteners. In this embodiment, the distal end of each cable includes a connector adapted to engage a threaded rod 357, and the machined block includes a through hole (for each cable) that receives the threaded rod 357. The threaded rod 357 is inserted into the appropriate through hole and secured in the machined block using a tension nut 358 and a lock nut 359 in a manner identical to that described above in connection with the connection mechanism 150 of the first joint assembly 100. In an exemplary embodiment, the connection mechanism 350 also functions as an adjustment member for varying a tension force applied to each cable. For example, a tension force is applied to a cable by tightening the tension nut 358 until the cable tension reaches a desired value in the same manner discussed above in connection with the connection mechanism 150 of the first joint assembly 100. In this manner, the connection mechanism 350 is configured to engage each of the cables 331, 332, 333, 334 and is adjustable to vary a tension force applied to each of the cables 331, 332, 333, 334. Additionally, the connection mechanism 350 is a floating tensioner because it moves with the driven member 320.

The connection mechanism 350 may also be used in combination with a guide member that is configured to position the distal ends of the cables of a cable set in a desired manner. In particular, the guide member maintains proper leads of the cables from the connection mechanism 350 back around to the pinion 316. In one embodiment, the guide member includes guide members 390a, 390b that are identical to the guide members 190a, 190b described above in connection with the first joint assembly 100 and function in the same manner.

Fourth Joint Assembly

Figure 12:
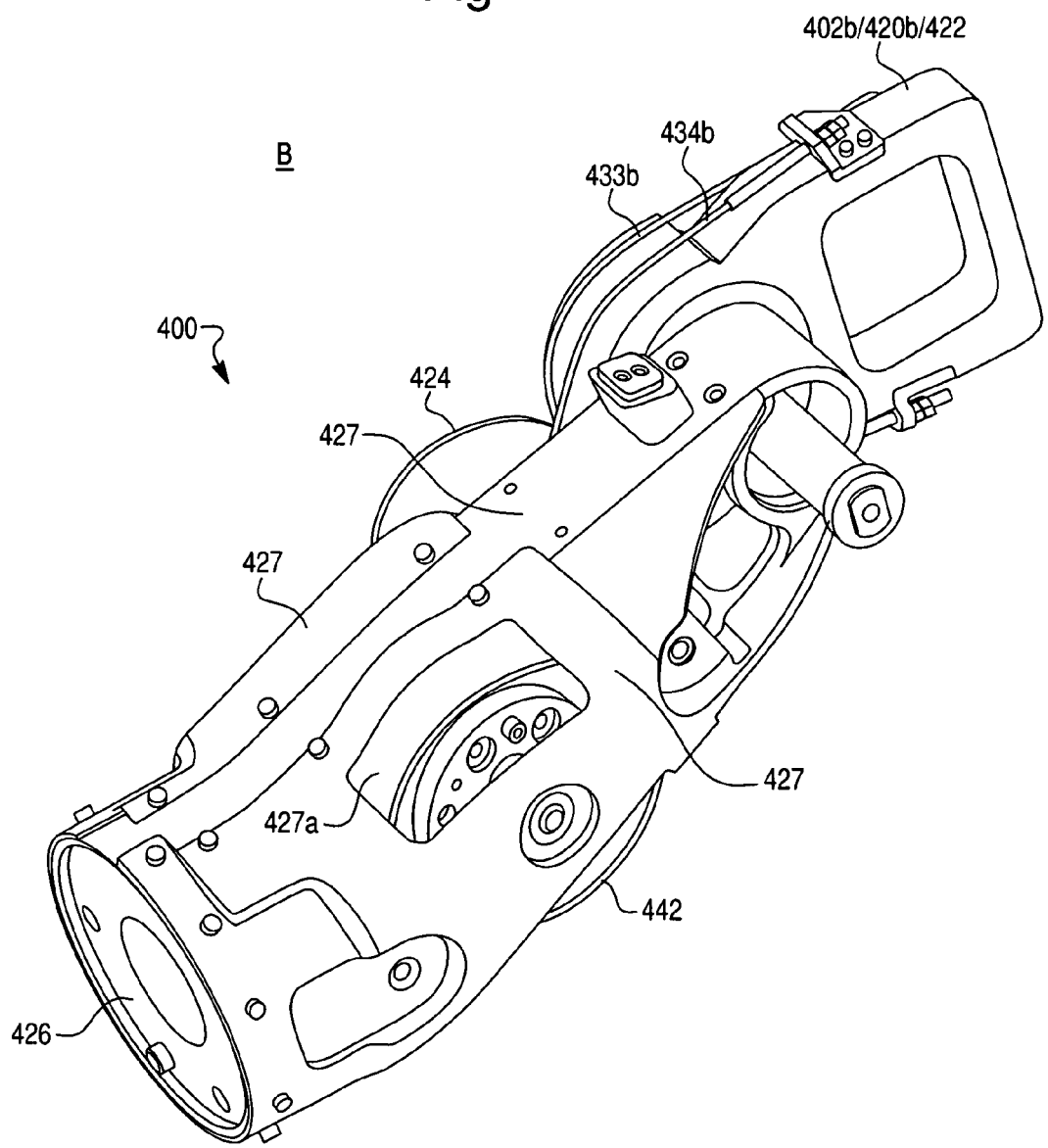
FIG. 12 is a perspective view of a second module according to an embodiment.

FIG. 12 shows the second module B according to an embodiment of the invention. In this embodiment, the second module B includes the fourth joint assembly 400. As noted above, the fourth joint assembly 400 provides one rotational degree of freedom. Thus, the second module B provides the fourth degree of freedom of the robotic arm 10. The output motion of the second module B is similar to the motion of a human elbow joint. For this reason, the second module B is also referred to as the robot elbow.

Figure 13:
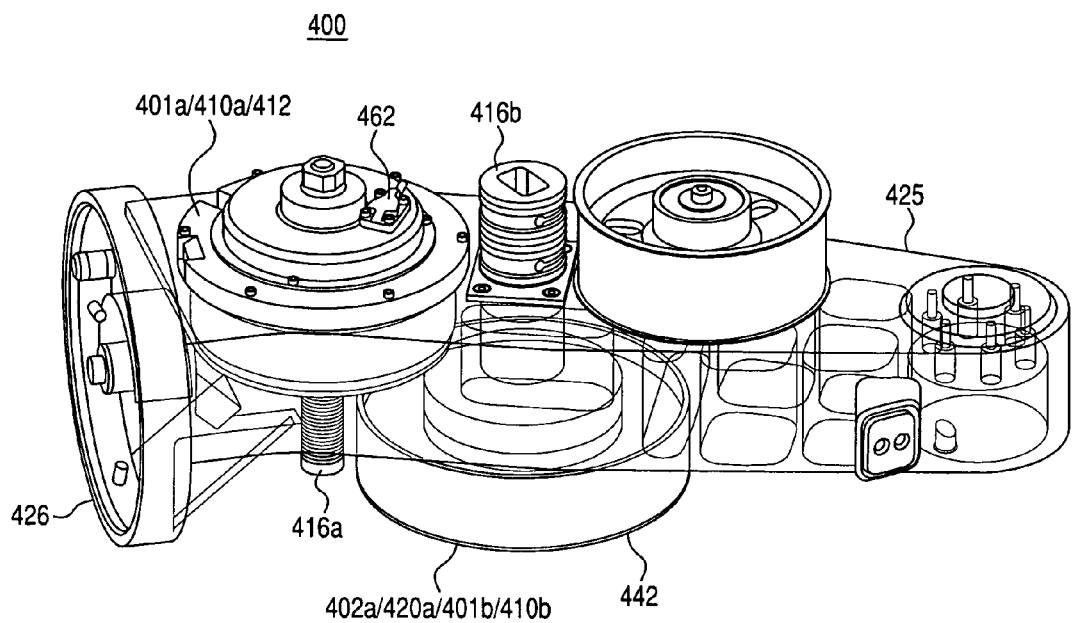
FIG. 13 is a perspective view of an embodiment of a joint assembly of the second module of FIG. 12.

FIGS. 12 and 13 show the fourth joint assembly 400 according to an embodiment of the invention. The fourth joint assembly 400 is disposed on the joint output (i.e., the output shaft 341) of the third joint assembly 300 and thus moves with the joint output of the third joint assembly 300. In contrast to the joint assemblies 100, 200, 300, the fourth joint assembly 400 preferably has a two stage transmission (i.e., two stages of drive reduction). In one embodiment, the first stage of the transmission includes a first component 401a (which includes a drive member 410a), a second component 402a (which includes a driven member 420a), and an at least partially flexible transmission 403a. Similarly, the second stage of the transmission includes a first component 401b (which includes a drive member 410b), a second component 402b (which includes a driven member 420b), and an at least partially flexible transmission 403b. For the avoidance of confusion, as used in this specification, a drive member is a component used to impart motion to a driven member and may be (a) "active," meaning capable of independent motion (e.g., a drive motor), or (b) "passive," meaning driven by another component (e.g., a pulley that is driven by a motor). The drive members of the joint assemblies 100, 200, 300 preferably are active drive members. In contrast, the fourth joint assembly 400 preferably includes both active and passive drive members.

As shown in FIGS. 12-16, the fourth joint assembly 400 incorporates a first stage transmission and a second stage transmission. The first stage transmission includes the drive member 410a that drives the driven member 420a via the flexible transmission 403a. Similarly, the second stage transmission includes the drive member 410b that drives the driven member 420b via the flexible transmission 403b. As can be seen in FIG. 13, the first and second stage transmissions share a component in common. Specifically, the driven member 420a and the drive member 410b are the same component. Because the drive member 410a imparts motion to the drive member 410b, the drive member 410b is a passive drive member as defined above.

According to an embodiment, the drive member 410a is a drive motor 412 (i.e., an active drive member) having a first stage pinion 416a and the driven member 420a is a pulley assembly 442 having a second stage pinion 416b. The flexible transmission 403a includes a plurality of cables that are connected to the drive motor 412 (via the first stage pinion 416a) and the pulley assembly 442 and transmit force and/or torque from the drive motor 412 to the pulley assembly 442. As can be seen in FIG. 13, the pulley assembly 442 is also the drive member 410b (i.e., a passive drive member). The flexible transmission 403b includes a plurality of cables that are connected to the pulley assembly 442 (via the second stage pinion 416b) and the driven member 420b and transmit force and/or torque from the pulley assembly 442 to the driven member 420b. The driven member 420b is an output member 422, which is the joint output of the fourth joint assembly 400. The second stage transmission also incorporates an idler pulley 424, which is a non-driven pulley included, for example, to reduce the amount of unsupported cable in the second stage transmission, which enables the drive member 410b to be located remotely from the driven member 420b.

The first and second stage transmissions of the fourth joint assembly 400 are disposed on a rigid frame 425 having a proximal end with an attachment flange 426 that is mounted on the output shaft 341 of the third joint assembly 300 (e.g., using mechanical fasteners). The rigid frame 425 supports the mechanisms of the drive train and has a length sufficient to ensure that the fourth joint assembly 400 provides the appropriate range of motion and "reach" needed by the surgeon to manipulate the robotic arm 10 to access the relevant portions of the patient's anatomy. The rigid frame 425 can be made of a rigid material, such as aluminum, a composite (e.g., a Kevlar® composite), or the like. Structural covers 427 can be mounted to the rigid frame 425 to provide additional stiffness to resist bending and/or torsion caused, for example, by forces applied by the surgeon as the surgeon manipulates the end effector 700. Preferably, the structural covers 427 include access openings 427a to facilitate inspection of the first and second transmissions and permit adjustment of cable tension and encoder system components without having to remove the structural covers 427. The ability to inspect and adjust joint assembly mechanisms without removing the structural covers 427 is particularly advantageous because the process of removing and reinstalling the structural covers 427 can alter the overall geometry of the robotic arm 10, such as by altering the overall flatness and location of a joint assembly's output (e.g., a distal end of the joint assembly) relative to the joint assembly's input (e.g., a proximal end of the joint assembly). Such alteration would adversely impact the accuracy of the robotic arm 10, requiring recalibration to restore accuracy. Calibration is a time consuming procedure that involves, for example, kinematically calibrating the robotic arm 10 by placing the robotic arm 10 in various known relative positions, capturing data at each position, comparing measured versus known position data, and reducing the error therebetween using a best fit process. Because kinematic calibration takes approximately thirty minutes, it is desirable to make every effort not to disturb the structural elements of the joint assemblies during service and inspection. The use of the access openings 427a in the structural covers 427 advantageously enables service and adjustment without disturbing the overall geometry of the robotic arm 10.

The flexible transmissions 403a, 403b of the fourth joint assembly 400 are similar to the flexible transmission 103 of the first joint assembly 100. Each flexible transmission 403a, 403b includes tension elements (e.g., cables) and may optionally include redundant tension elements. In one embodiment, the flexible transmission 403b includes redundant tension elements while the flexible transmission 403a is non-redundant. For example, in this embodiment, the flexible transmission 403a includes a first transmission element comprising a first cable 431a and a second transmission element comprising a second cable 432a. Although the cables 431a, 432a can be configured in a variety of ways to impart motion to the pulley assembly 442, in this embodiment, each of the cables 431a, 432a has a proximal end connected to the drive motor 412 and a distal end connected to a connection mechanism on the pulley assembly 442. The cables 431a, 432a are not redundant because each cable performs a different function. Specifically, the cable 431a functions to exert a tension force on the pulley assembly 442 in a direction L (shown in FIG. 14A) when the pinion 416a of the drive motor 412 rotates to wind the cable 431a onto the pinion 416a. In contrast, the cable 432a functions to exert a tension force on the pulley assembly 442 in a direction M when the pinion 416a rotates to wind the cable 432a onto the pinion 416a. In this manner, the flexible transmission 403a is coupled to the drive member 410a and the driven member 420a and is configured to cause movement of the driven member 420a in response to movement of the drive member 410a. As explained above, the flexible transmission 403a utilizes two cables that are not redundant in function. In contrast, the flexible transmission 403b includes a first transmission element having a first plurality of tension elements (or transmission sub-elements) and a second transmission element having a second plurality of tension elements (or transmission sub-elements). In this embodiment, the first transmission element is a first cable set that includes the first plurality of tension elements, which includes a first cable 431b and a second cable 432b. Similarly, the second transmission element is a second cable set that includes the second plurality of tension elements, which includes a third cable 433b and a fourth cable 434b. Thus, the flexible transmission 403b includes redundant cables the advantages of which are described above in connection with the first joint assembly 100. For example, the cables 431b, 432b are redundant because each cable 431b, 432b performs the same function of exerting a tension force on the output member 422 in a direction N (shown in FIG. 14) when the pinion 416b of the pulley assembly 442 rotates to wind the cables 431b, 432b onto the pinion 416b. Similarly, the cables 433b, 434b are redundant because each cable 433b, 434b performs the same function of exerting a tension force on the output member 422 in a direction P when the pinion 416b of the pulley assembly 442 rotates to wind the cables 433b, 434b onto the pinion 416b. Although the cables 431b, 432b, 433b, 434b can be configured in a variety of ways to impart motion to the output member 422, in this embodiment, each of the cables 431b, 432b, 433b, 434b has a proximal end connected to the pulley assembly 442 and a distal end connected to the output member 422. The cables 431a, 432a, 431b, 432b, 433b, 434b may be any cables appropriate for use in a robotic system but are preferably tungsten cables.

Figure 14A:
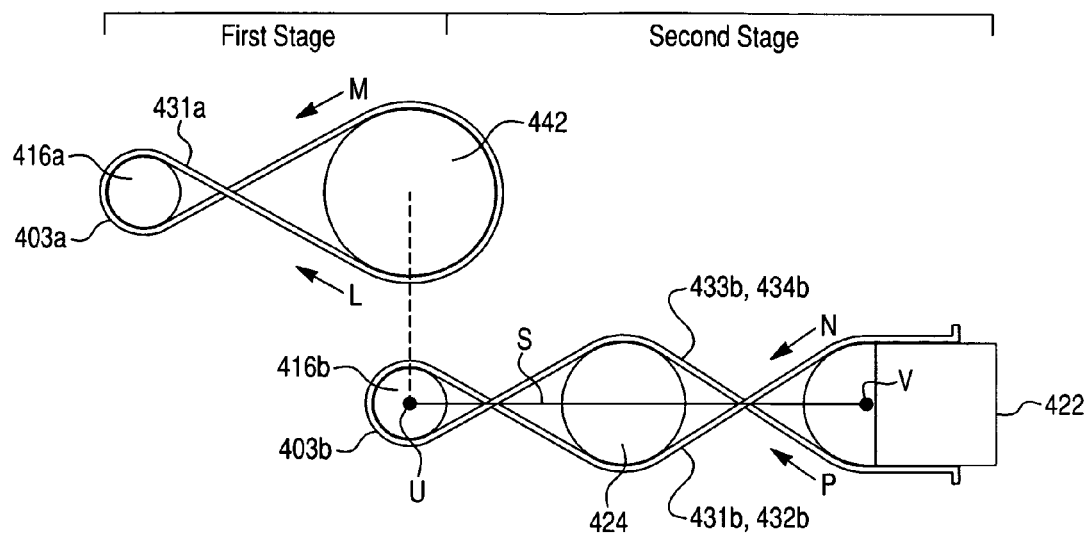
FIG. 14A is a schematic of an embodiment of first and second stage flexible transmissions of the second module of FIG. 12.
Figure 14B:
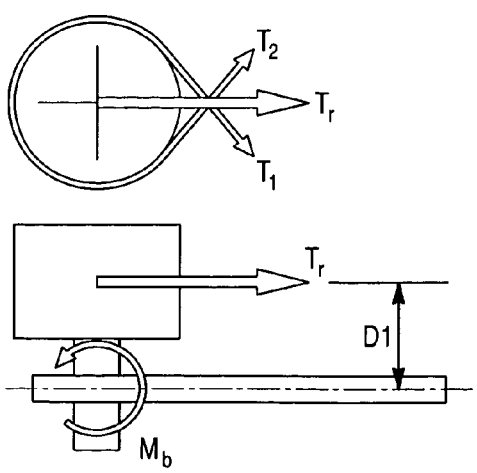
FIG. 14B is a force diagram of an embodiment of a tension element configuration of the second module of FIG. 12.
Figure 14C:
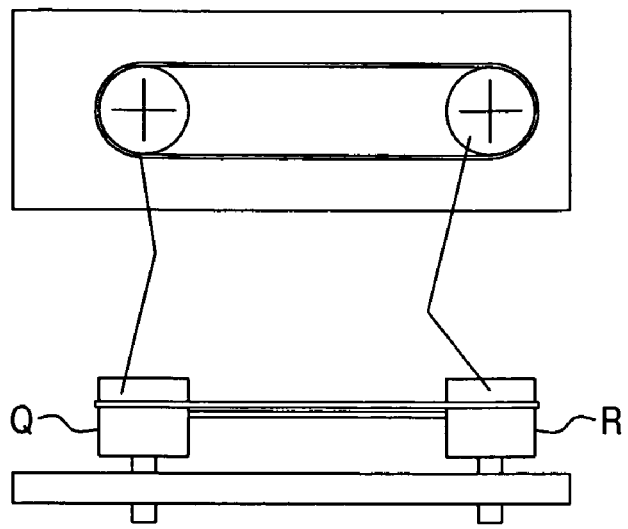
FIG. 14C is a schematic of a conventional tension element configuration.
Figure 14D:
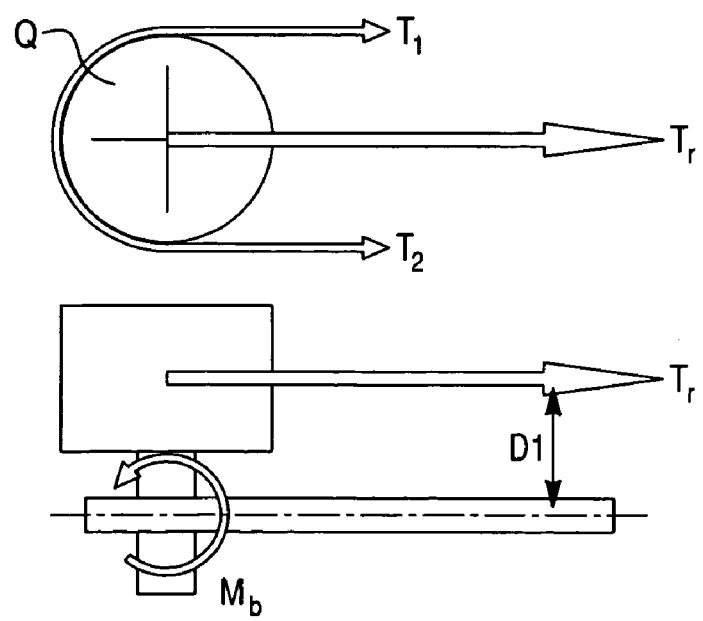
FIG. 14D is a force diagram of the conventional tension element configuration of FIG. 14C.

One potential disadvantage of using a cable transmission is the need to pre-tension the cables to eliminate slack that would cause backlash of the transmission. Pre-tensioning load values are typically 15% to 50% of the cable breaking strength, which results in large cable tension forces being imparted to bearings of drive train components and their support structure. For example, as shown in FIG. 14C, the simplest cable arrangement is one where each cable leads off one side of a drive train component Q (e.g., a drive member) and leads onto the next drive train component R (e.g., a driven member) on the same side. The resultant cable force Tr is the sum of a cable tension force T1 and a cable tension force T2, and the bending moment Mb is the resultant cable force Tr times a distance D1 from the cables to a neutral axis of the support structure (e.g., the rigid frame 425). As illustrated by the length of the arrow in FIG. 14D, for this simple cable arrangement, the resultant cable force Tr has a large magnitude, which results in large bearing loads and bending moments. The high load also increases friction forces in the drive train components and contributes to surgeon fatigue because, to manipulate the robotic arm 10, the surgeon must apply sufficient force to overcome the increased friction forces.

According to an embodiment, the cables of the first and second stage transmissions are preferably configured to reduce loads on drive train component bearings and bending moments on the rigid frame 425. One way to decrease the loads and moments is to arrange the cables in a manner that decreases the resultant cable force Tr. In one embodiment, this is accomplished by arranging the cables in a "crossover" (or "tangent wrap") configuration where the cables overlap one another between drive train components. In other words, the cables are crossed at each juncture between drive train components. For example, as shown in FIG. 14A, the cables of the first stage transmission are arranged so the cable 431a crosses over (or under) the cable 432a after the cables 431a, 432a lead off the drive motor 412 but before they contact the pulley assembly 442. The cables of the second stage transmission are similarly arranged. Thus, for both the first and second stage transmissions, the first transmission element crosses the second transmission element at least once between the coupling of the first transmission element to the drive member 410a, 410b and the coupling of the first transmission element to the driven member 420a, 420b. Another way to describe the crossover configuration (using the second stage transmission in FIG. 14A to illustrate) is to consider a plane S defined by an axis of rotation U of the drive member 410b and an axis of rotation V of the driven member 420b (or an intermediate component, such as the idler pulley 424). The axes of rotation U, V are parallel. As can be seen, the first and second transmission elements of the second stage transmission each include a portion in contact with the drive member 410a, a portion in contact with at least one of the driven member 420b and the intermediate component (e.g., the idler pulley 424), and a portion therebetween, where the portion therebetween intersects the plane S. Because the cables 431b, 432b and the cables 433b, 434b are oriented to overlap one another in this manner, the tension forces of the cables 431b, 432b, 433b, 434b partially offset one another so the resultant cable force Tr is less than the sum of a tension force T1 of the cables 431b, 432b and a tension force T2 of the cables 433b, 434b. As illustrated in FIG. 14B, this results in a lower resultant cable force Tr than that shown in FIG. 14D, which advantageously reduces bearing loads and bending moments.

Motive force is provided to the fourth joint assembly 400 by the drive member 410a. As noted above, the drive member 410a includes the drive motor 412, which imparts rotational motion to the pulley assembly 442 via the flexible transmission 403a. The drive motor 412 may be any motor suitable for driving the pulley assembly 442. In one embodiment, the drive motor 412 is integral with the rigid frame 425. The integral construction includes a stator bonded directly to the rigid frame 425 and a rotor 419 having a motor shaft 414 from which the first stage pinion 416a extends. Integral construction advantageously increases structural strength of the rigid frame 425 while creating a compact design for the fourth joint assembly 400. Additionally, integral construction improves drive motor cooling because the rigid frame 425 is a substantial heat sink, and thermal conduction is greater with an integral stator than with a separate stator that is bolted to the rigid frame 425.

Preferably, the drive motor 412 includes a motor encoder configured to measure angular rotation of the motor shaft 414. The motor encoder may be similar to the encoder measurement systems discussed above in connection with the drive motors of the joint assemblies 100, 200, 300. For example, as shown in FIG. 13, the motor encoder includes an encoder scale (not shown) that rotates with the motor shaft 414 and an encoder read head 462a that reads the encoder scale. Thus, the motor encoder enables measurement of the angular rotation of the motor shaft 414, which, as discussed above in connection with the joint assembly 100 can be compared with the angular rotation of the joint output (e.g., as measured by a joint encoder) to evaluate the integrity of the flexible transmission of the fourth joint assembly 400. Additionally, the drive motor 412 may optionally include a motor brake similar to the motor brake 111 described above in connection with the first joint assembly 100.

Figure 17:
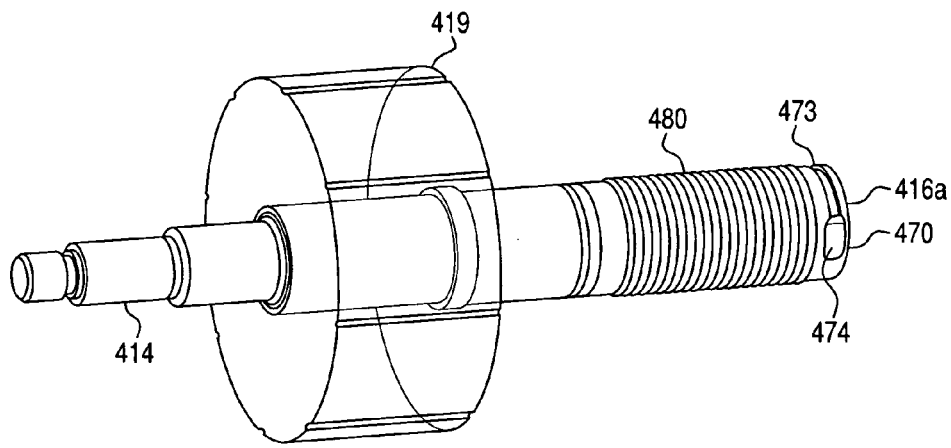
FIG. 17 is a perspective view of an embodiment of a motor shaft and pinion of the second module of FIG. 12.

As shown in FIG. 17, the motor shaft 414 of the drive motor 412 is bonded to the rotor 419, and the first stage pinion 416a extends from the motor shaft 414. The first stage pinion 416a may be coupled to or integral with the motor shaft 414 and includes attachment elements 470 for securing the proximal ends of the cables 431a, 432a. An attachment element 470 may have any configuration suitable for securely anchoring a cable to the pinion 416a. For example, the attachment element 470 may be similar to the attachment elements 170 described above in connection with pinion 116 of the first joint assembly 100. Alternatively, in one embodiment, the proximal end of each cable 431a, 432a has a connector 4 (such as a stainless steel or brass ball as shown in FIG. 34) swaged thereto, and the attachment element 470 is configured to seat the connector 4 when the cable is under tension. For example, as shown in FIG. 17, the attachment element 470 comprises a rounded (e.g., hemispherical) groove 474 (or relief) sized to receive the connector 4 and a channel groove 473 large enough to receive the cable but not to permit the connector 4 to pass from the rounded groove 474 to the channel groove 473. When the connector 4 is fitted into the rounded groove 474, the cable is seated in the channel groove 473, and tension is applied to the cable in a direction away from the connector 4, the connector 4 seats into the rounded groove 474. As long as sufficient tension is maintained on the cable, the connector 4 remains seated. The cable can be decoupled from the attachment element 470 by releasing sufficient tension from the cable.

Preferably, one attachment element 470 is disposed on each end of the pinion 416a. The cable 431a engages the attachment element 470 on a distal end of the pinion 416a, and the cable 432a engages the attachment element 470 on a proximal end of the pinion 416a. For each attachment element 470, the portion of the cable that exits the attachment element 470 engages a guide 480. The guide 480 may be similar to the guide 180 described above in connection with the first joint assembly 100 except, in this embodiment, the guide 480 is configured for use with single cables as opposed to redundant cables. For example, instead of a double helix arrangement, the guide 480 may be a single spiral (e.g., helical) groove (or "single helix" arrangement) that extends along a length of the first stage pinion 416a. The guide 480 receives the cables 431a, 432a, which wind around the first stage pinion 416a in opposite directions and eventually lead off the first stage pinion 416a and wrap circumferentially around the pulley assembly 442 in opposite directions before terminating at a connection mechanism disposed on the pulley assembly 442.

Figure 18:
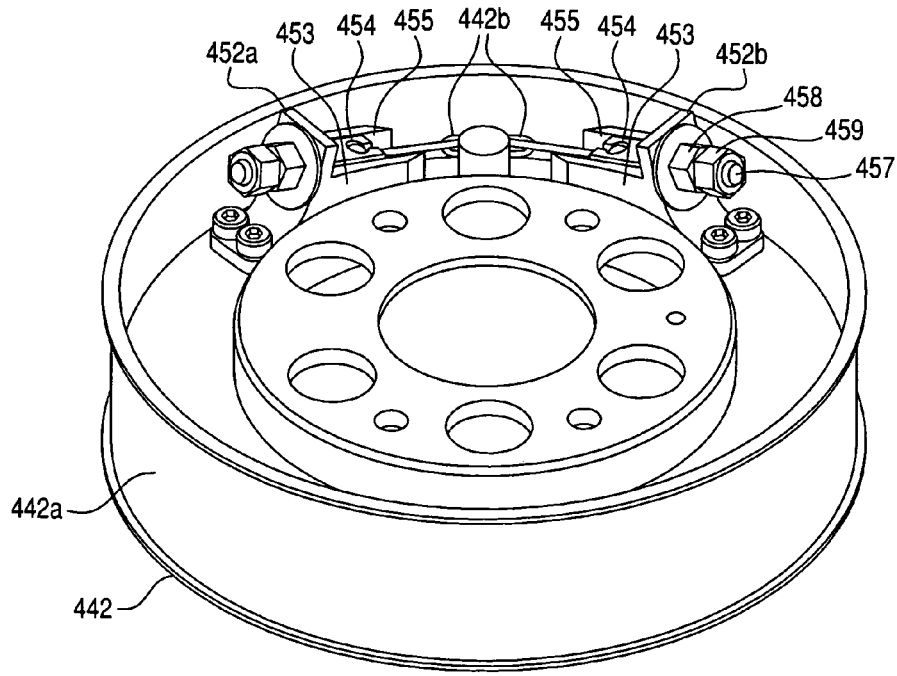
FIG. 18 is a top perspective view of an embodiment of a connection mechanism of the second module of FIG. 12.

The connection mechanism may be integral with or coupled to the pulley assembly 442 and may have any configuration suitable for securely anchoring the cables 431a, 432a. For example, the connection mechanism may be similar to one or more of the connection mechanisms described above in connection with the joint assemblies 100, 200, 300. In the embodiment of FIG. 18, the connection mechanism includes a first coupling component 452a and a second coupling component 452b disposed remotely from the first coupling component 452a. In this embodiment, each coupling component 452a, 452b is disposed inwardly of a circumferential perimeter 442a of the pulley assembly 442 and includes a base 453 that is attached to the pulley assembly 442 with mechanical fasteners. The pulley assembly 442 includes apertures 442b through which the cables 431a, 432a pass to reach the coupling components 452a, 452b. Each coupling component 452a, 452b includes a coupling member 454 configured to receive a distal end of a cable and a slot 455 configured to receive the coupling member 454. The coupling member 454 and slot 455 are preferably similar to the coupling member 152 and slots 156a, 156b described above in connection with the first joint assembly 100, including incorporating a threaded rod 457, tension nut 458, and lock nut 459 that function as an adjustment member for varying a tension force applied to the cable.

Rotation of the pulley assembly 442 occurs when the drive motor 412 actuates causing the first stage pinion 416a to rotate. When the first stage pinion 416a rotates, the cable 431a winds around (or unwinds from) the pinion 416a and the cable 432a conversely unwinds from (or winds around) the pinion 416a depending on the direction of rotation. Because the distal ends of the cables 431a, 432a are coupled to the pulley assembly 442, the winding and unwinding of the cables 431a, 432a exerts force and/or torque on the pulley assembly 442 that causes the pulley assembly 442 to rotate. As explained above, the pulley assembly 442 is a passive drive member that imparts rotational motion to the output member 422 via the flexible transmission 403b. In particular, the pulley assembly 442 includes the second stage pinion 416b to which proximal ends of the cables 431b, 432b, 433b, 434b are coupled. When the pulley assembly 442 rotates, the cables 431b, 432b wind around (or unwind from) the second stage pinion 416b and the cables 433b, 434b conversely unwind from (or wind around) the second stage pinion 416b depending on the direction of rotation. Because the distal ends of the cables 431b, 432b, 433b, 434b are coupled to the output member 422, the winding and unwinding of the cables 431b, 432b, 433b, 434b exerts force and/or torque on the output member 422 that causes the output member 422 to rotate thereby providing the fourth rotational degree of freedom J4 shown in FIG. 2.

Figure 20:
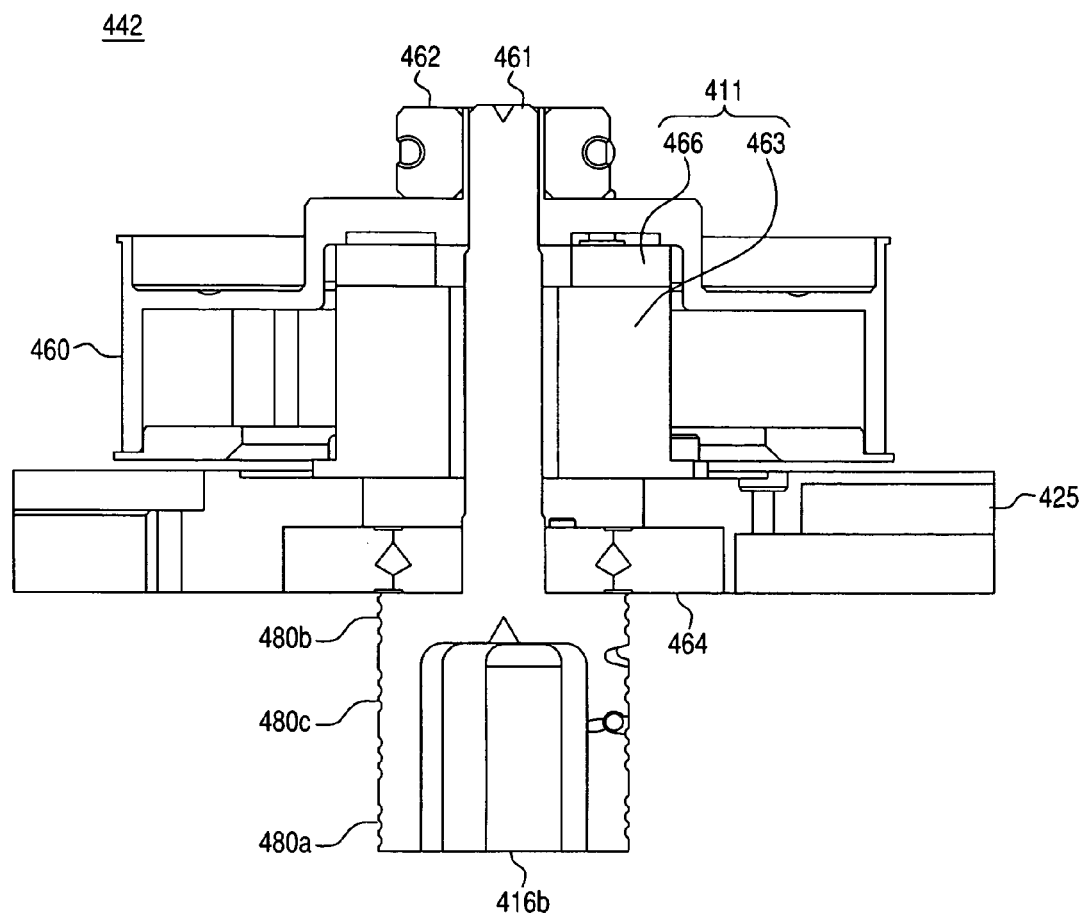
FIG. 20 is a cross-sectional view of an embodiment of a drive member of the second module of FIG. 12.

The pulley assembly 442 preferably includes a pulley brake 411 configured to inhibit rotation of the second stage pinion 416b. The pulley brake 411 may be any suitable brake assembly but is preferably a permanent magnet type brake manufactured by Kendrion Electromagnetic Group of Germany. The brake 411 is internal to the pulley assembly 442. For example, as shown in FIG. 20, the pulley assembly 442 includes a pulley 460 that is rigidly attached to a shaft 461 of the second stage pinion 416b with a collar type shaft clamp 462. The shaft 461 is mounted to the rigid frame 425 via a cross roller bearing 464. The brake 411 includes a brake hub 466 that is fixed to an internal portion of the pulley 460 and a brake body 463 that is fixed to the rigid frame 425. In operation, when the brake 411 is energized, the brake hub 462 (and thus pulley 460, shaft clamp 462, and second stage pinion 416b) is free to rotate relative to the rigid frame 425. When power is removed from the brake 411, however, the brake 411 constrains the brake hub 462, which inhibits rotation of the pulley 460, shaft clamp 462, and second stage pinion 416b. Similar to the motor brake 111 discussed above in connection with the first joint assembly 100, the pulley brake 411 is a failsafe mechanism that can be triggered, for example, in response to a fault signal. Additionally, as described above in connection with the first joint assembly 100, the incorporation of a brake on the second stage drive member (i.e., the pulley assembly 442) along with redundant cables in the second stage flexible transmission 403b, enables the joint output (i.e., the output member 422) to be unbraked.

Figure 19A:
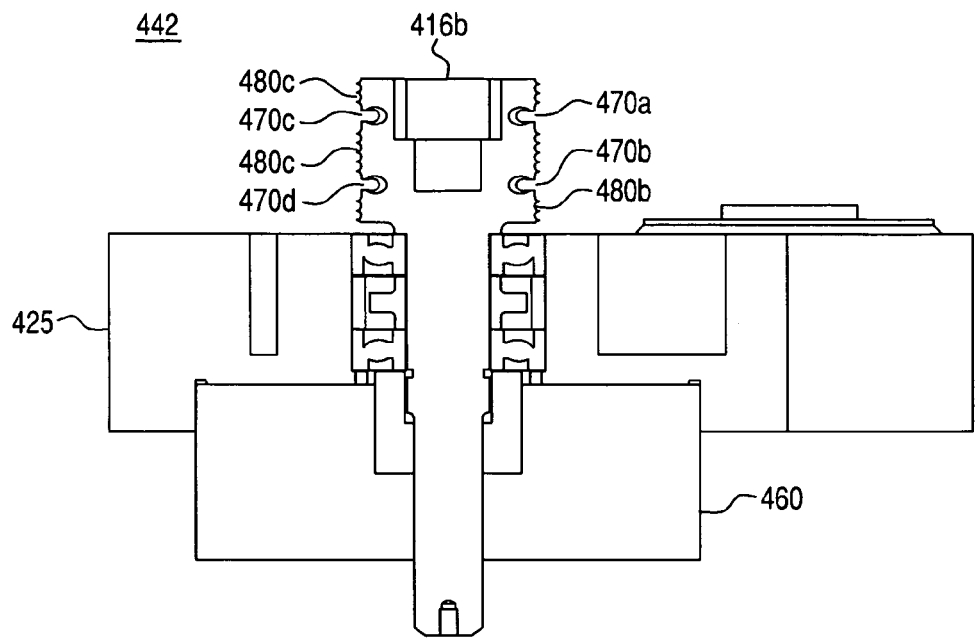
FIG. 19A is a cross-sectional view of an embodiment of a drive member of the second module of FIG. 12.
Figure 19B:
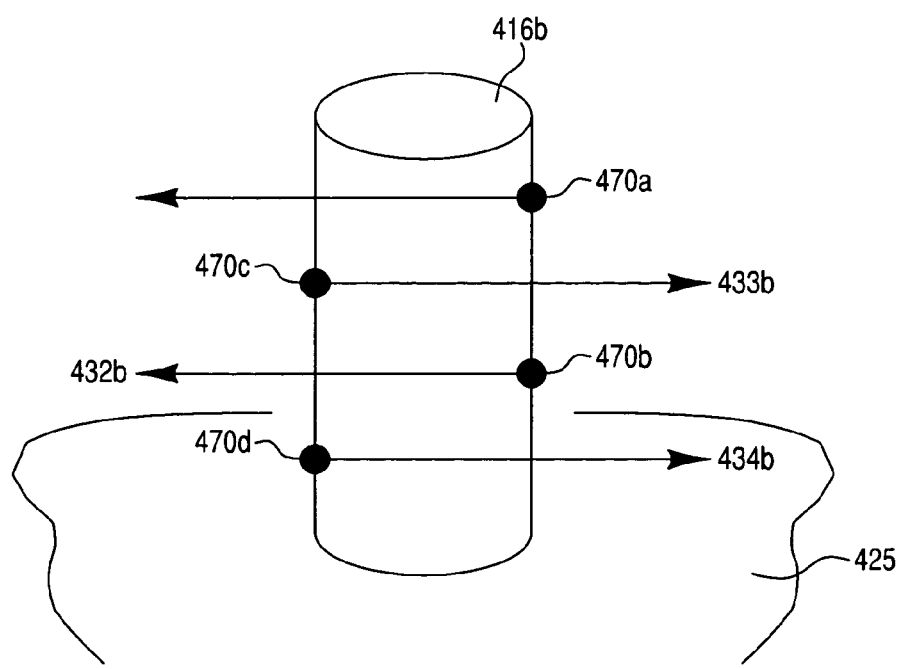
FIG. 19B is a schematic of an embodiment of a flexible transmission coupled to a drive member of the second module of FIG. 12.

The second stage pinion 416b includes attachment elements for securing the proximal ends of the cables 331b, 332b, 333b, 334b. An attachment element may have any configuration suitable for securely anchoring a cable to the pinion 416b. For example, the attachment element may be similar to the attachment elements 170 described above in connection with the first joint assembly 100. Alternatively, in one embodiment, the second stage pinion 416b includes attachment elements that are similar to the attachment elements 470 of the first stage pinion 416a, and the proximal end of each of the cables 431b, 432b, 433b, 434b includes a connector 4 (such as stainless steal or brass balls as shown in FIG. 34) swaged thereto that seats in an attachment element in the same manner described above in connection with the first stage pinion 416a. In contrast to the first stage pinion 416a (which includes two attachment elements 470 for two cables), the second stage pinion 416b includes four attachment elements 470a, 470b, 470c, 470c (shown in FIG. 19A) disposed along a length of the second stage pinion 416b to accommodate the four cables 431b, 432b, 433b, 434b. As shown in FIG. 19B, the cables 431b, 432b couple to the attachment elements 470a, 470b, respectively, and the cables 433b, 434b couple to the attachment elements 470c, 470d, respectively. For each attachment element 470a, 470b, 470c, 470d, the portion of the cable that exits the attachment element engages a guide. The guide may be similar to the guide 480 described above in connection with the first stage pinion 416a except the guide is configured for use with redundant cables as opposed to single cables. For example, in this embodiment, the guide includes a first guide 480a that receives and guides the cable 431b and a second guide 480b that receives and guides the cable 434b. The guide also includes a third guide 480c disposed between the first and second guides 480a, 480b that receives and guides the cables 432b, 433b. In particular, the cable 432b is received in a proximal portion of the third guide 480c, and the cable 333b is received in a distal portion of the third guide 480c. Each of the first, second, and third guides 480a, 480b, 480c comprises a single spiral (e.g., helical) groove (or "single helix" arrangement) that extends along a portion of the length of the second stage pinion 416b. Alternatively, the second stage pinion 416b could incorporate a double helix arrangement as described above in connection with the pinion 116 of the first joint assembly 100. As shown in FIGS. 14A and 19B, the cables 331b, 332b and the cables 333b, 334b wind around the second stage pinion 416b in opposite directions, lead off the second stage pinion 416b and wrap circumferentially around the idler pulley 424, lead off the idler pulley 424 and are routed onto a proximal curved end of the output member 422, and terminate at connection mechanisms disposed on the output member 422.

The idler pulley 424 is a non-driven pulley included, for example, to reduce the amount of unsupported cable in the second stage transmission. Although this embodiment includes one idler pulley, other embodiments may include multiple idler pulleys or no idler pulleys. Whether to include an idler pulley(s) can be determined based on, for example, transmission configuration details, such as the distance between the drive member and the driven member. The idler pulley 424 may be any pulley known in the art for supporting a tension element in a tension element drive transmission. Advantageously, the combined use of idler pulleys and the crossover cable configuration enables transmission of power over a distance while minimizing drive friction and structural loading due to cable tension, which allows the design of a flexible transmission that is backdrivable with extremely low backlash.

Figure 15:
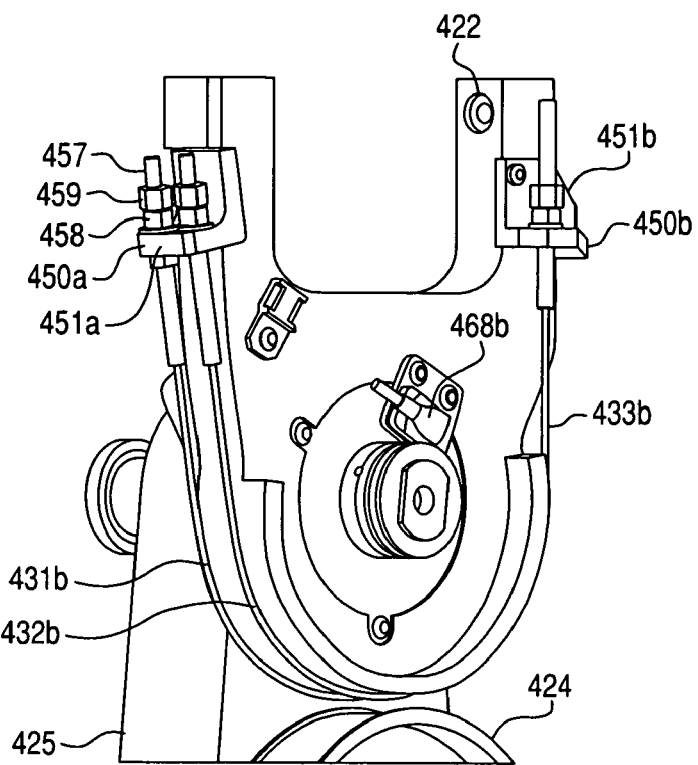
FIGS. 15 and 16 are perspective views of an embodiment a driven member of the second module of FIG. 12.
Figure 16:
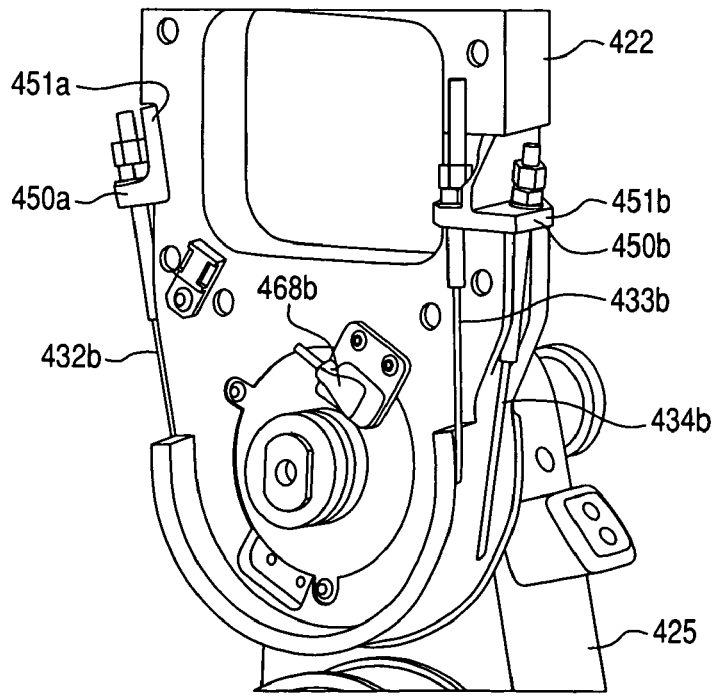
Figure 21:
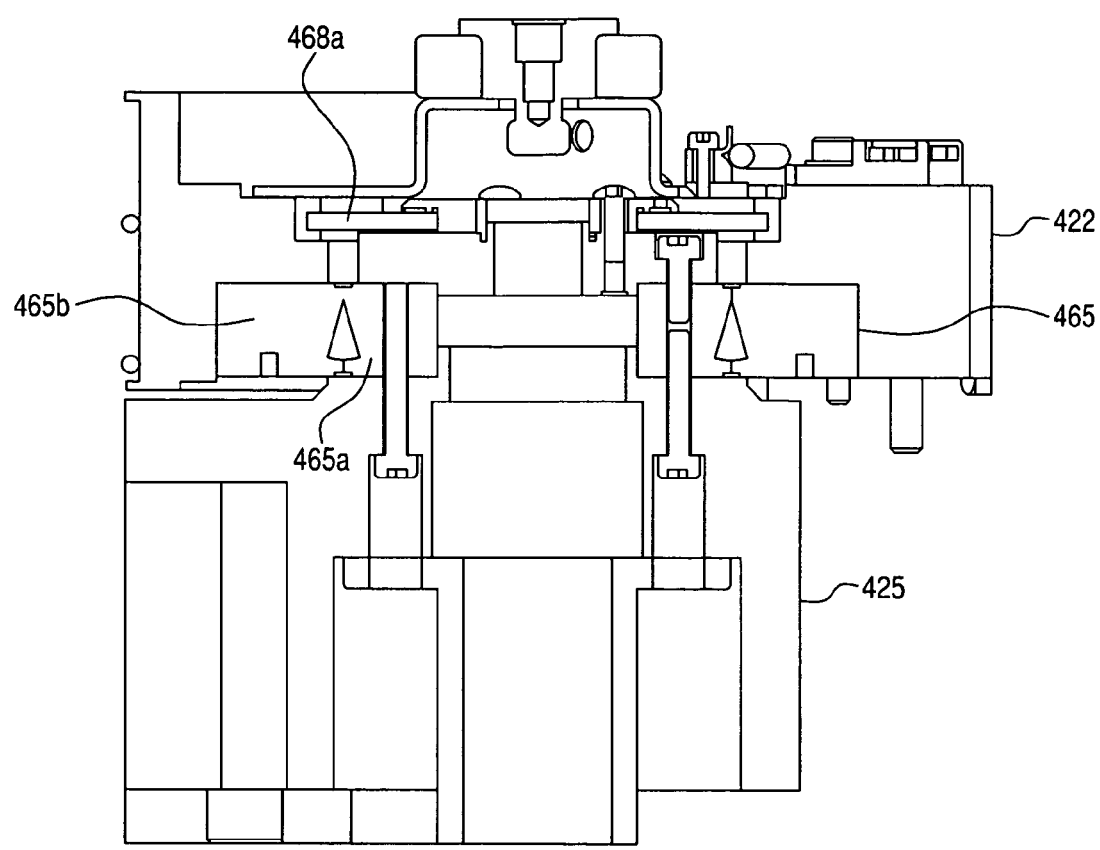
FIG. 21 is a cross-sectional view of an embodiment of a driven member of the second module of FIG. 12.

The output member 422, which is driven by the pulley assembly 442 via the flexible transmission 403b, is the joint output for the fourth joint assembly 400. As shown in FIGS. 15 and 16, in one embodiment, the output member 422 is a plate-like component having a curved proximal end onto which the cables 431b, 432b, 433b, 434b wrap. The output member 422 is coupled to the rigid frame 425 via a cross roller bearing 465. The cross roller bearing 465 may be any suitable cross roller bearing that can maintain stiffness of the elbow joint while keeping friction low. In a preferred embodiment, the cross roller bearing 465 is manufactured by IKO Nippon Thompson Co., Ltd. of Japan. As shown in FIG. 21, an inner race 465a of the cross roller bearing 465 is coupled to the rigid frame 425 with mechanical fasteners, and an outer race 465b of the cross roller bearing 465 is coupled to the output member 422 with mechanical fasteners. The output member 422 may also provide points of attachment for the protective covers 20 and/or the bellows 22 as well as mounting posts for the protective cover 20 for the fifth joint assembly 500.

As with the joint assemblies 100, 200, 300, the joint output (in this case the output member 422) of the fourth joint assembly 400 preferably includes a joint encoder configured to measure angular rotation of the joint output. Any suitable encoder system can be used. In one embodiment, as shown in FIG. 21, the joint encoder includes an encoder scale 468a mounted to the inner race 465a of the cross roller bearing 465 through a spacer and an encoder read head 468b (shown in FIGS. 15 and 16) coupled to the output member 422. As the output member rotates, markings on the encoder scale 468a are read by the encoder read head 468b to determine angular position of the output member 422. For relative encoder systems, an encoder index mark is also included as discussed above in connection with the joint encoder of the first joint assembly 100. As explained above, the rotational output can be compared to the rotational input from the drive motor 412 (measured by the motor encoder) to determine whether the integrity of the flexible transmission has been compromised.

As shown in FIGS. 15 and 16, the output member includes a first connection mechanism 450a for securing the cables 331b, 332b and a second connection mechanism 450b for securing the cables 333b, 334b. The first and second connection mechanisms 450a, 450b may be integral with or coupled to the output member 422 and may have any configuration suitable for securely anchoring the cables 431b, 432b, 433b, 434b. According to an embodiment, the first and second connection mechanisms 450a, 450b comprise brackets 451a, 451b, respectively, that are mounted on the output member 422 using mechanical fasteners. Each bracket 451a, 451b includes two through holes for receiving the respective cables. In this embodiment, the distal end of each cable includes a threaded rod 457 that is inserted into the corresponding through hole and secured using a tension nut 458 and a lock nut 459 in a manner identical to that described above in connection with the coupling components 252 of the second joint assembly 200. In an exemplary embodiment, the threaded rod 457, tension nut 458, and lock nut 459 also function as an adjustment member for varying a tension force applied to each cable 431b, 432b, 433b, 434b as described above in connection with the coupling components 252 of the second joint assembly 200.

Fifth Joint Assembly

Figure 22A:
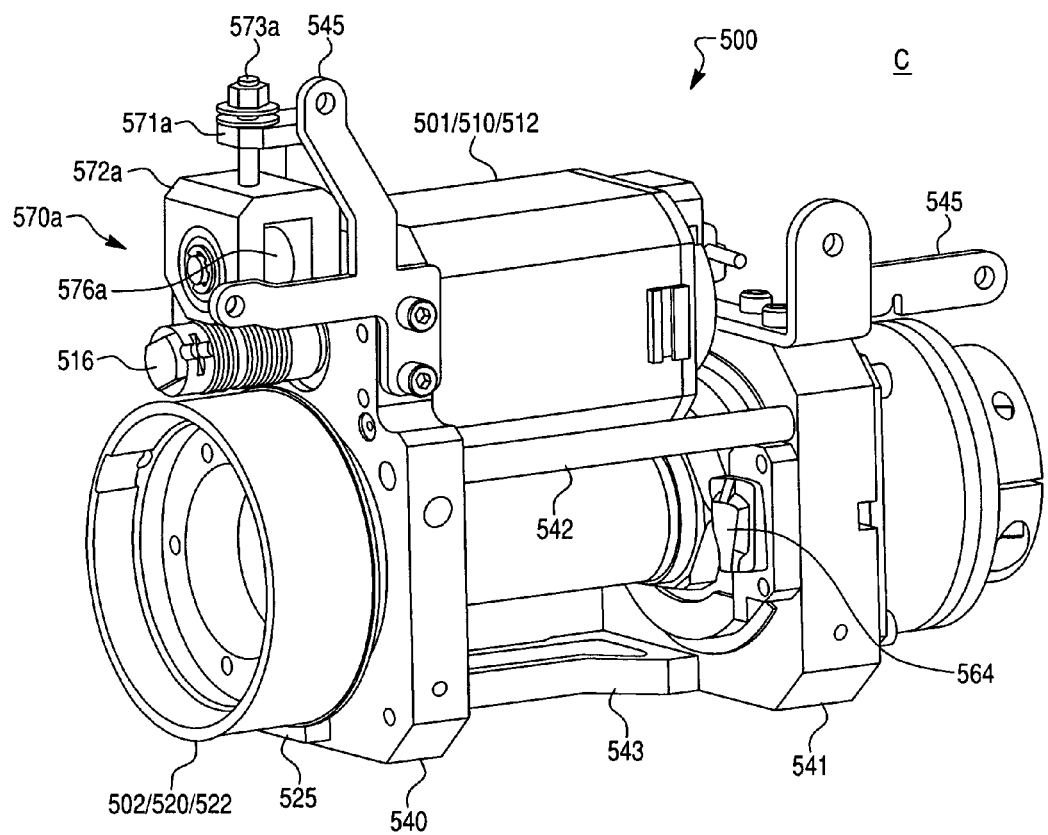
FIG. 22A is a perspective view of a third module according to an embodiment.

FIG. 22A shows the third module C according to an embodiment of the invention. In this embodiment, the third module C includes the fifth joint assembly 500. As noted above, the fifth joint assembly 500 provides one rotational degree of freedom. Thus, the third module C provides the fifth degree of freedom of the robotic arm 10. The output motion of the third module C is similar to the rotation of a human forearm.

FIGS. 22A-22D show the fifth joint assembly 500 according to an embodiment of the invention. The fifth joint assembly 500 is disposed on the joint output (i.e., the output member 422) of the fourth joint assembly 400 and thus moves with the joint output of the fourth joint assembly 400. The fifth joint assembly 500 includes a first component 501, a second component 502, and an at least partially flexible transmission 503. In this embodiment, the first component 501 includes a drive member 510, and the second component 502 includes a driven member 520. The flexible transmission 503 is coupled to the drive member 510 and the driven member 520 and is configured to move the driven member 520 in response to movement of the drive member 510.

According to an embodiment, the fifth joint assembly 500 includes a support structure comprising front and back plates 540, 541 separated by spacers 542 and a lateral plate 543. This support structure supports the drive member 510 and the driven member 520 and provides points of attachment for attaching the fifth joint assembly 500 (e.g., using mechanical fasteners) to the output member 422 of the fourth joint assembly 400, as shown in FIG. 4. The front and back plates 540, 541 also support brackets 545, which provide mounting locations for the protective covers 20. In this embodiment, the drive member 510 is a drive motor 512 (i.e., an active drive member), and the driven member 520 is an output pulley 522 disposed on an output shaft 524 that is supported on angular contact bearings 523. The bearings 523 are axially preloaded using a bearing preload nut 521 to remove axial and radial play that could contribute to errors in positioning of the end effector 700. The flexible transmission 503 includes a plurality of cables that are connected to the drive motor 512 and the output pulley 522 and transmit force and/or torque from the drive motor 512 to the output pulley 522. The output pulley 522 is the joint output of the fifth joint assembly 500. To limit rotation of the output pulley 522, a hard stop 525 is disposed on the front plate 540 and corresponding hard stop bumpers (not shown) are disposed on the output pulley 522. When rotation of the output pulley 522 causes a hard stop bumper to contact the hard stop 525, rotation of the output pulley 522 is constrained.

Figure 22B:
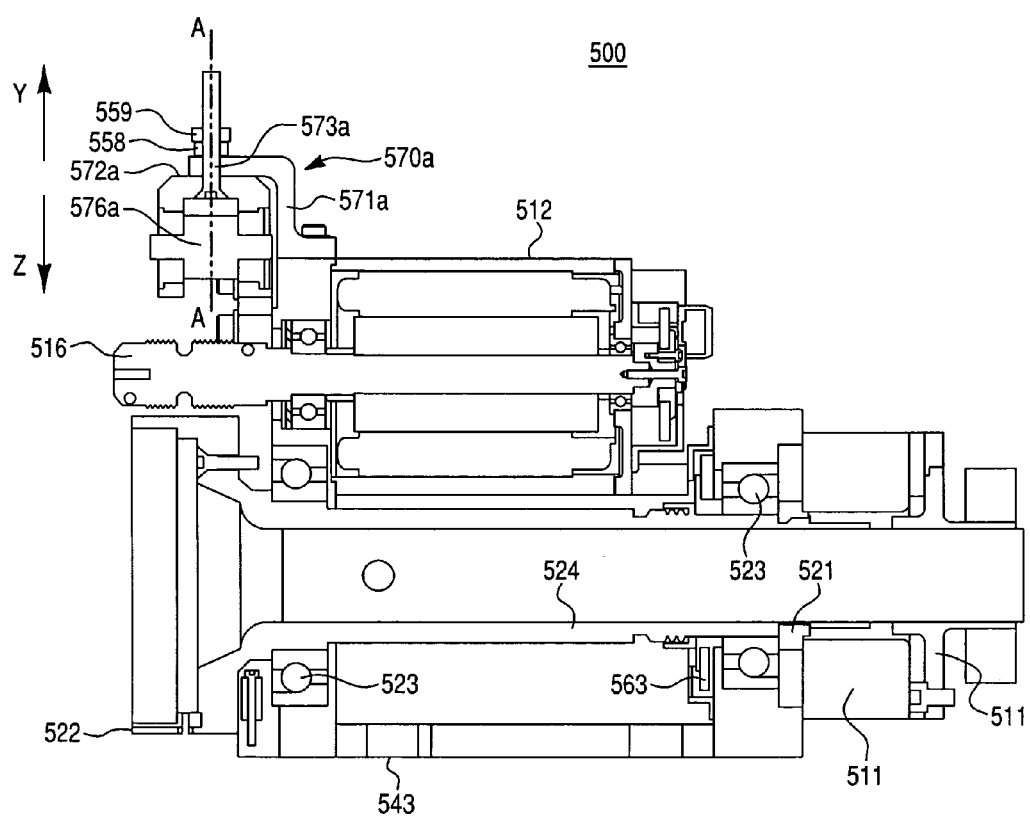
FIG. 22B is a cross-sectional view of the third module of FIG. 22A.
Figure 23:
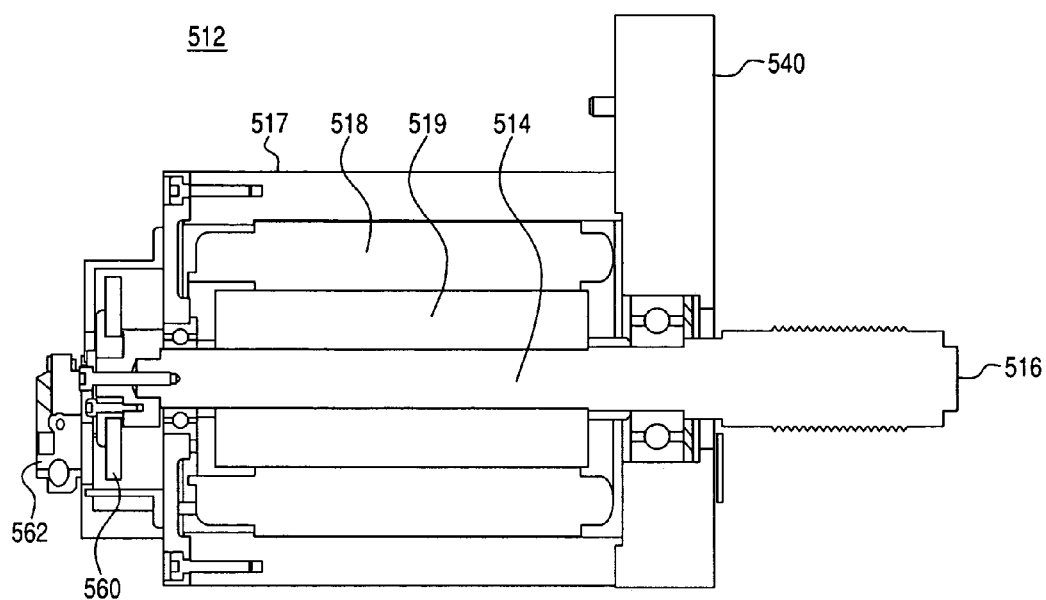
FIG. 23 is a cross-sectional view of an embodiment a drive member of the third module of FIG. 22A.

The drive member 510 provides motive force to the fifth joint assembly 500. As noted above, the drive member 510 includes the drive motor 512, which imparts rotational motion to the output pulley 522 via the flexible transmission 503. The drive motor 512 may be any motor suitable for driving the output pulley 522. As shown in FIG. 23, the drive motor 512 includes a housing 517 that houses a rotor 519 and a stator 518 that turn a motor shaft 514. As with the joint assemblies 100, 200, 300, 400, the drive motor 512 includes a motor encoder to enable measurement of the angular rotation of the motor shaft 514. In this embodiment, the motor encoder includes an encoder scale 560 that rotates with the motor shaft 514 and an encoder read head 562 mounted to the housing 517 that reads the encoder scale 560. Similarly, the joint output (in this case, the output pulley 522) includes a joint encoder configured to measure angular rotation of the joint output. In one embodiment, the joint encoder includes an encoder scale 563 (shown in FIG. 22B) attached to the output shaft 524 via a locking nut and an encoder read head 564 (shown in FIG. 22A) attached to the back plate 541 via a bracket. As the output shaft 524 (and thus the output pulley 522) rotates relative to the back plate 541, the encoder read head 564 reads the encoder scale 563. As a result, the angular rotational input provided by the drive motor 512 (measured by the motor encoder) can be compared to the angular rotational output of the joint output (measured by the joint encoder) to determine whether the integrity of the flexible transmission of the fifth joint assembly 500 has been compromised.

The fifth joint assembly 500 is similar to the third joint assembly 300 in that the drive motor 512 does not include a motor brake. Instead, the fifth joint assembly 500 utilizes a joint brake 511 coupled directly to the joint output (i.e., the output pulley 522). The joint brake 511 may be any suitable brake assembly. In one embodiment, the joint brake 511 is coupled to the output pulley 522 via the output shaft 524. For example, the joint brake 511 includes a rotor that is rigidly attached to the output shaft 524 using a brake shaft clamp. The joint brake 511 can be actuated to constrain rotation of the output shaft 524 (and thus the output pulley 522) as appropriate, such as when a fault condition is triggered or if loss of power occurs. Inclusion of the joint brake 511 in the fifth joint assembly 500 means that non-redundant cables can be used in the flexible transmission 503 without compromising the safety of the robotic arm 10.

As shown in FIG. 23, the drive motor shaft 514 includes a pinion 516 to which the flexible transmission 503 is coupled. According to an embodiment, the flexible transmission 503 of the fifth joint assembly 500 is similar to the flexible transmission 403*a* of the first stage transmission of the fourth joint assembly 400 and includes a plurality of tension elements. Although the flexible transmission 503 may optionally include redundant tension elements, in this embodiment, incorporation of the joint brake 511 enables the use of non-redundant tension elements, as noted above. In this embodiment, the flexible transmission 503 is non-redundant and includes a first transmission element comprising a first cable 531 (i.e., a first tension element) and a second transmission element comprising a second cable 532 (i.e., a second tension element). Although the cables 531, 532 can be configured in a variety of ways to impart motion to the output pulley 522, in this embodiment, each of the cables 531, 532 has a proximal end connected to the drive motor 512 (i.e., at the pinion 516) and a distal end connected to the output pulley 522. The cables 531, 532 are not redundant because each cable 531, 532 performs a different function. Specifically, the cable 531 functions to exert a tension force on the output pulley 522 in a direction W (shown in FIG. 22C) when the pinion 516 rotates to wind the cable 531 onto the pinion 516. In contrast, the cable 532 functions to exert a tension force on the output pulley 522 in a direction X when the pinion 516 rotates to wind the cable 532 onto the pinion 516. Thus, the flexible transmission 503 utilizes two cables that are not redundant in function. The cables 531, 532 may be any cables appropriate for use in a robotic system but are preferably tungsten cables.

Figure 22C:
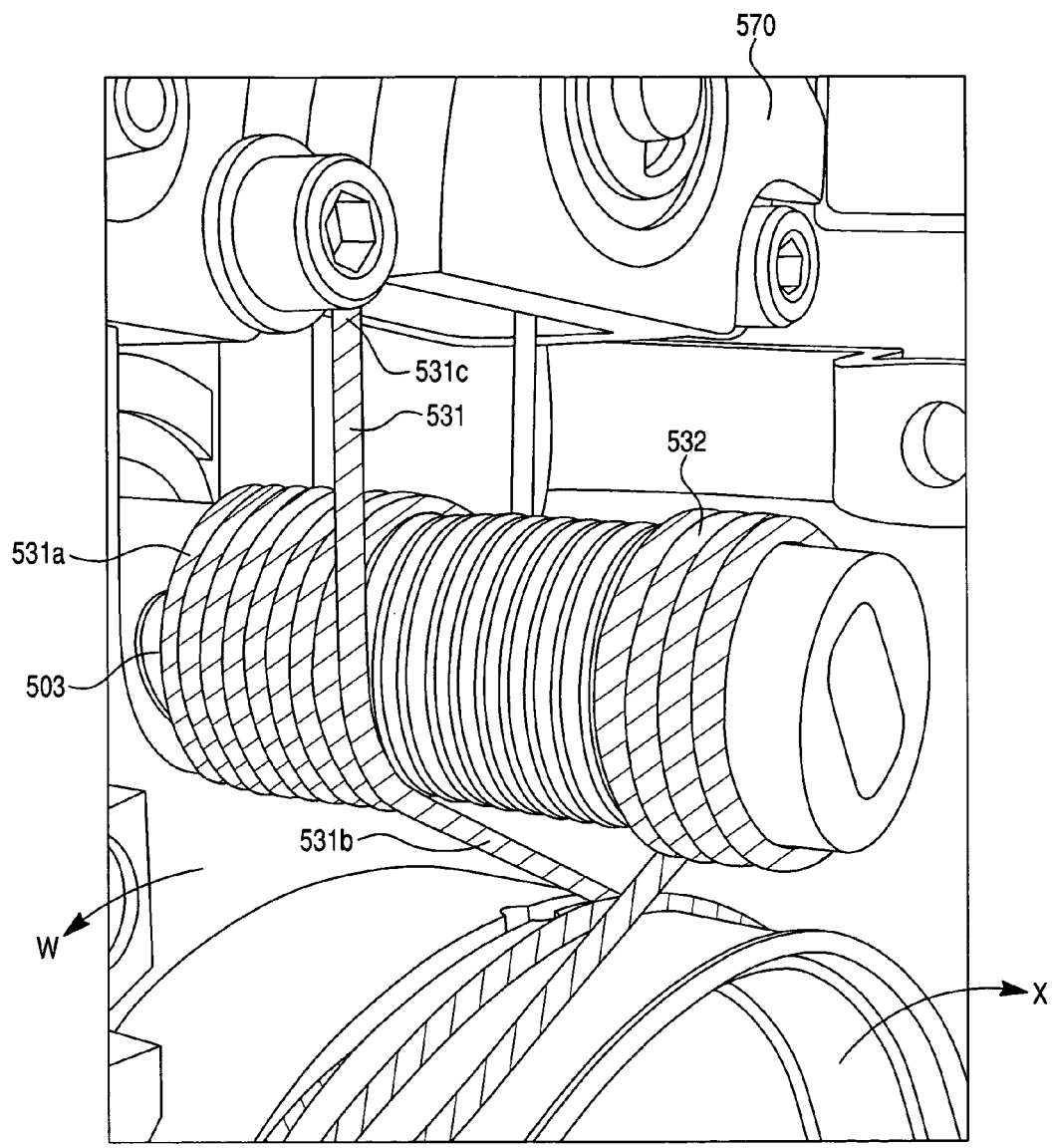
FIG. 22C is a perspective view of an embodiment of a flexible transmission of the third module of FIG. 22A.
Figure 24:
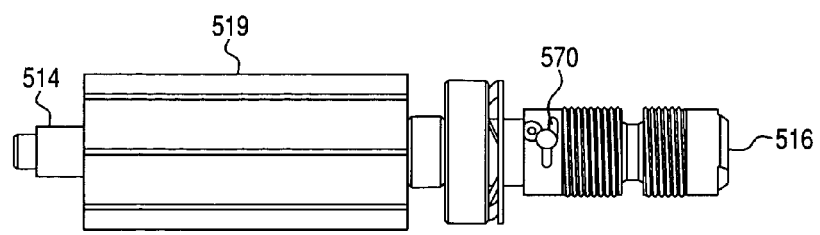
FIG. 24 is a side elevation view of an embodiment of a motor shaft and pinion of the third module of FIG. 22A.

As shown in FIG. 24, the pinion 516 includes attachment elements 570 for securing the proximal ends of the cables 531, 532. An attachment element 570 may have any configuration suitable for securely anchoring a cable to the pinion 516. For example, an attachment element 570 may be similar to any of the attachment elements described herein, such as the attachment elements described in connection with the joint assemblies 100, 400. In one embodiment, the proximal end of each cable 531, 532 has a connector 4 (such as a stainless steel or brass ball as shown in FIG. 34) swaged thereto, and the attachment element 570 is configured to seat the connector 4 when the cable is under tension in the same manner as described above in connection with the attachment elements of the fourth joint assembly 400. The pinion 516 includes two attachment elements 570 (one for the cable 531 and one for the cable 532) disposed on opposite ends of the pinion 516. As shown in FIG. 22C, each cable 531, 532 has a proximal end connected to and wound around the pinion 516 in the same manner as described above in connection with the pinion 116 of the first joint assembly 100. The first and second cables 531, 532 lead off (or extend from) the pinion 516 in opposite directions. Although both cables 531, 532 could be routed directly from the pinion 516 to the driven member 520 (e.g., as described above in connection with the pinion 416*a* of the fourth joint assembly 400), in this embodiment, the cable 531 leads off the pinion 516 and loops around an adjustment member 570 (e.g., a tensioner assembly) located above the pinion 516, then travels downward past the pinion 516 and wraps around a circumferential perimeter of the output pulley 522, and finally terminates at a connection mechanism 550 on the output pulley 522. Thus, as best shown in FIG. 22C, the flexible transmission 503 includes a first tension element (i.e., the cable 531) having a first (or proximal) portion 531*a* coupled to the drive member 510 (i.e., the pinion 516), a second (or distal) portion 531*b* coupled to the driven member 520, and an intermediate portion 531*c* between the first portion 531*a* and the second portion 531*b*, where the adjustment member 570 engages the intermediate portion 531*c*. In contrast, the second tension element (i.e., the cable 532) is not engaged by the adjustment member 570. Instead, the cable 532 includes a portion coupled to the drive member 510 and a portion coupled to the driven member 520. The cable 532 leads off the pinion 516, travels downward and wraps around the circumference of the output pulley 522, and then terminates at the connection mechanism 550 on the output pulley 522. The cables 531, 532 engage the connection mechanism 550 from opposite sides. When the drive motor 512 is actuated, the pinion 516 rotates causing the cable 531 to wind around (or unwind from) the pinion 516 and the cable 532 to conversely unwind from (or wind around) the pinion 516 depending on the direction of rotation. Because the distal ends of the cables 531, 532 are connected to the output pulley 522, the winding and unwinding of the cables 531, 532 exerts force and/or torque on the output pulley 522 that causes the output pulley 522 to rotate thereby providing the fifth rotational degree of freedom J5 shown in FIG. 2.

The drive member 510 is disposed between the driven member 510 and the adjustment member 570. The adjustment member 570 is configured to be adjusted to vary a tension force applied to at least one of the cables 531, 532. Unlike conventional cable tensioning devices, the adjustment member 570 is not coupled to an end of the cable to be tensioned. Instead, the adjustment member 70 is configured to engage the intermediate portion 531*c* of the cable, which is a part of the cable located between the proximal and distal ends. Although the adjustment member 570 can be designed to engage the cable 531, the cable 532, or both of the cables 531, 532, in a preferred embodiment, the adjustment member 570 engages only the cable 531. In operation, movement of the adjustment member 570 toward or away from the pinion 516 varies the tension force applied to the intermediate portion 531*c* (and thus to the cable 531 overall). Because (1) the cables 531, 532 are both coupled to the pinion 516 and the output pulley 522 and (2) the output pulley 522 is able to rotate, adjustment of the tension force applied to the cable 531 automatically results in adjustment of the tension force applied to the cable 532 in accordance with principles of equilibrium. Thus, the flexible transmission 503 is configured so that a tension force applied to the second tension element (i.e., the cable 532) is varied when the adjustment member 570 is adjusted to vary the tension force applied to the first tension element (i.e., the cable 531). As a result, the two separate cables 531, 532 of the fifth joint assembly 500 can both be tensioned by adjusting only one tensioning mechanism (i.e., the adjustment member 570). In contrast, conventional cable tension devices may require adjustment of two separate tensioning mechanisms to adjust the tension of two separate cables. Alternative embodiments include engaging both cables 531, 532 with the adjustment member 570 or including an independent adjustment member for each cable 531, 532.

Figure 26:
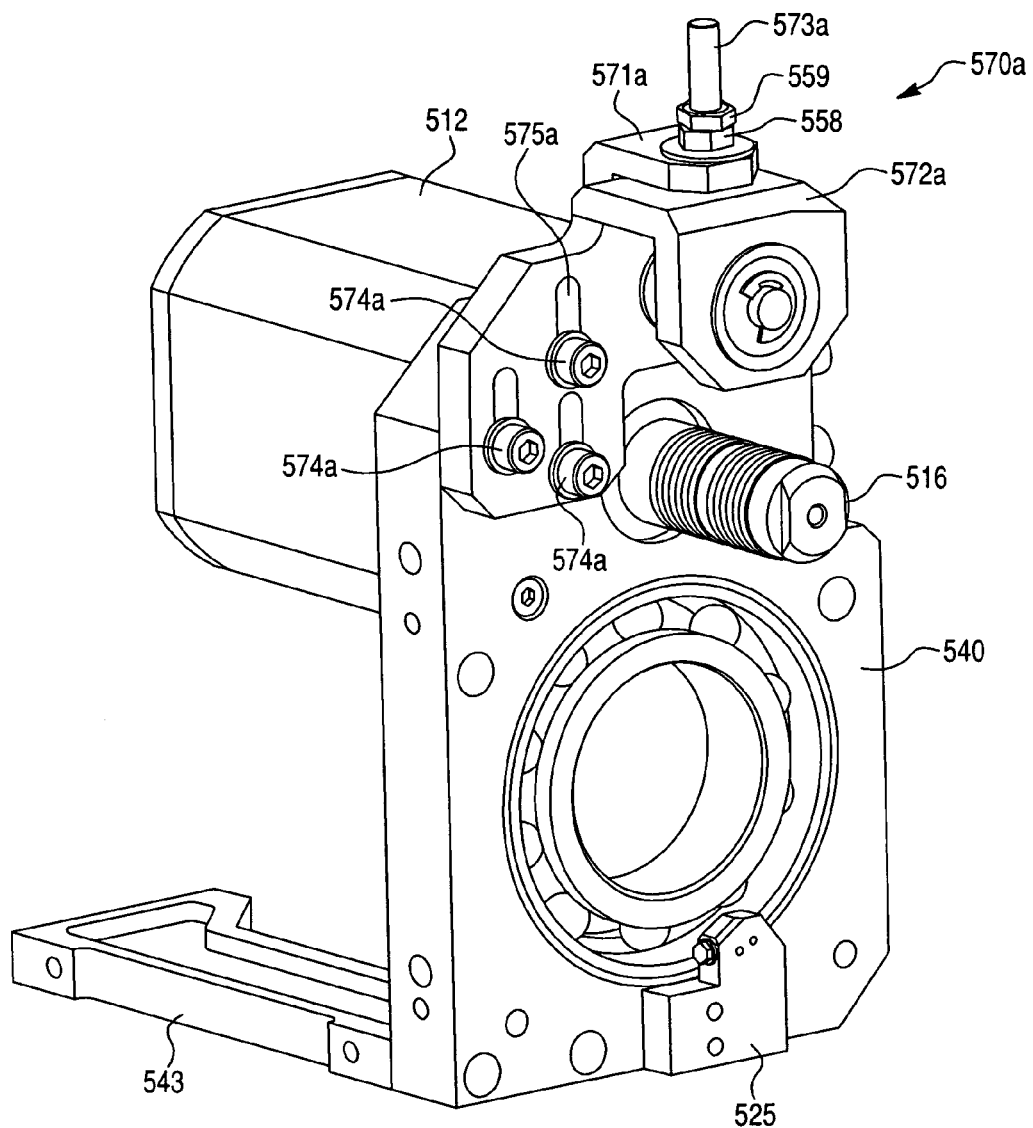
FIG. 26 is a front perspective view of an embodiment an adjustment member of the third module of FIG. 22A.

As will be recognized by one of skill in the art, the adjustment member 570 can have any configuration that (a) is capable of engaging the intermediate portion of at least one of the cables 531, 532 and (b) is adjustable to vary a tension force applied thereto. The configuration of the adjustment member 570 can be determined based on various factors, such as the size of the joint assembly and the amount of space available for travel of the adjustment member 570. According to one embodiment, as shown in FIGS. 22B and 26, an adjustment member 570*a* includes a support bracket 571*a* coupled to the front plate 540 and a yoke 572*a* coupled to the support bracket 571*a* by a tension adjustment screw 573*a*. The tension adjustment screw 573*a* is held in position by a tension nut 558 and a lock nut 559. The yoke 572a is also coupled directly to the front plate 540 via fasteners 574a that engage corresponding elongated slots 575a in the yoke 571a. A portion of the adjustment member 570a comprises a tension pulley 576a that is supported in the yoke 571a by bearings. In the installed configuration, the cable 531 leads off the pinion 516 and loops around the tension pulley 576a, then travels downward past the pinion 516 and wraps around a circumference of the output pulley 522 before being secured to the connection mechanism 550 on the output pulley 522. The portion of the cable 531 that loops over the tension pulley 576a is the intermediate portion 531c. To tension the cable 531, the fasteners 574a are loosened, which enables the yoke 571a (and thus the tension pulley 576a) to move relative to the front plate 540 along a linear path. The tension nut 558 is then tightened, which draws up the tension adjustment screw 573a. The yoke 571a is coupled to the tension adjustment screw 573a and therefore travels upward as the tension adjustment screw 573a is drawn up in a direction Y. The tension pulley 576a moves upward with the yoke 571a, thereby increasing a tension force applied to the cable 531. To decrease the tension force, the tension nut 558 is loosened, which moves the yoke 571a and tension pulley 576a downward in a direction Z. In this manner, the adjustment member 570a is configured to increase a tension force applied to the first tension element (i.e., the cable 531) when the adjustment member 570a moves in a first direction (i.e., the direction Y) and to decrease a tension force applied to the first tension element when the adjustment member 570a moves in a second direction (i.e., the direction Z). In this embodiment, the first and second directions are along a line (or a predetermined axis A-A). When the cable 531 is tensioned to a desired value, the lock nut 559 is tightened to prevent loosening of the tension nut 558 (e.g., due to vibration). The fasteners 574a are also tightened to constrain the yoke 571a relative to the front plate 540. As explained above, tensioning the cable 531 in this manner advantageously also results in tensioning of the cable 532.

Figure 27A:
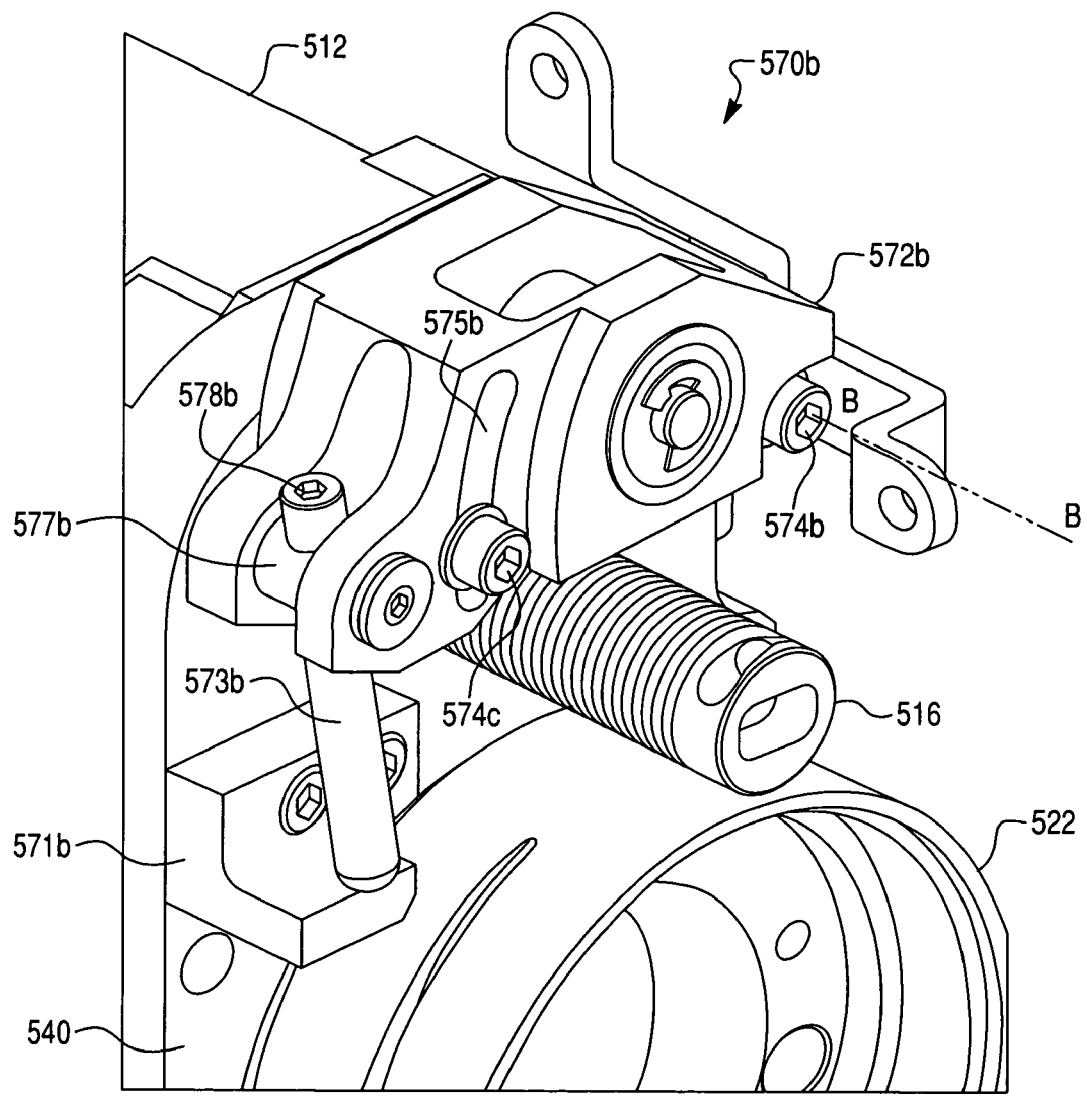
FIG. 27A is a front perspective view of an embodiment of an adjustment member of the third module of FIG. 22A.
Figure 27B:
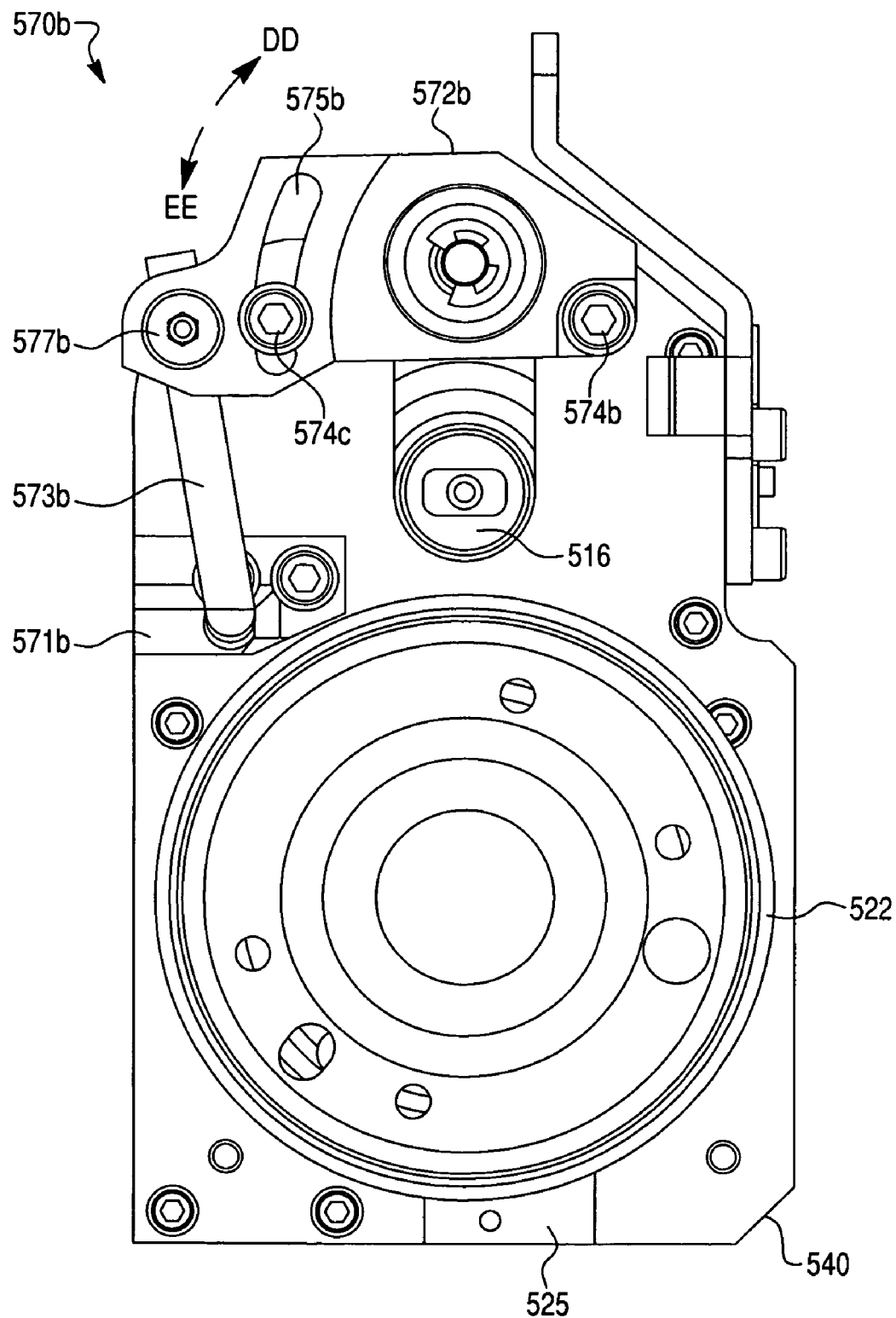
FIG. 27B is a front elevation view of the adjustment member of FIG. 27A.

According to another embodiment, as shown in FIGS. 27A and 27B, an adjustment member 570b is configured to travel along a nonlinear path (e.g., an arcuate path) to tension a cable. A nonlinear path may be desirable, for example, in situations where a joint assembly does not have sufficient space for an adjustment member to travel linearly. In this embodiment, the adjustment member 570b is similar to the adjustment member 570a except the adjustment member 570b is configured to rotate about a pivot line B-B (or a predetermined axis), which results in a tensioner pulley 576b moving along an arc. For example, the adjustment member 570b includes a yoke 572b that is coupled to the front plate 540 with a first fastener 574b that defines the pivot line B-B and a second fastener 574c that engages an elongated slot 575b in the yoke 572b. When the fasteners 574b, 574c are tightened, the yoke 572b is constrained relative to the front plate 540. When the fasteners 574b, 574c are loosened, the yoke 572b is permitted to rotate about the pivot line B-B. The adjustment member 570b also includes a support bracket 571b that supports a tension adjustment screw 573b. The tension adjustment screw 573b is coupled to a threaded pin 577b that is pivotably coupled to the yoke 572b. The yoke 572b further includes bearings that support the tension pulley 576b. In the installed configuration (which is identical to the installed configuration of the adjustment member 570a), the cable 531 leads off the pinion 516 and loops around the tension pulley 576b, then travels downward past the pinion 516 and wraps around the circumference of the output pulley 522 before being secured to the connection mechanism 550 on the output pulley 522. To tension the cable 531, the fasteners 574b, 574c are loosened, and the tension adjustment screw 573b is adjusted (e.g., using a hex wrench engaged with a recess 578b in the tension adjustment screw 573b, which causes the yoke 572b to pivot about the pivot line B-B. For example, turning the tension adjustment screw 573b so that the yoke 572b pivots in a clockwise direction about the pivot line B-B causes the tension pulley 576b disposed on the yoke 572b to move upward in a first direction DD along a slight arc, thereby increasing a tension force exerted on the cable 531. To decrease the tension force, the tension adjustment screw 573b is turned so that the yoke 572b pivots in a counterclockwise direction about the pivot line B-B, which causes the tension pulley 576b to move downward in a direction EE thereby decreasing a tension force exerted on the cable 531. In this embodiment, the first and second directions DD, EE are along an arc. When the cable 531 is tensioned to a desired value, the fasteners 574b, 574c are tightened to constrain the yoke 572b relative to the front plate 540. As explained above, tensioning the cable 531 in this manner advantageously also results in tensioning of the cable 532.

Figure 25A:
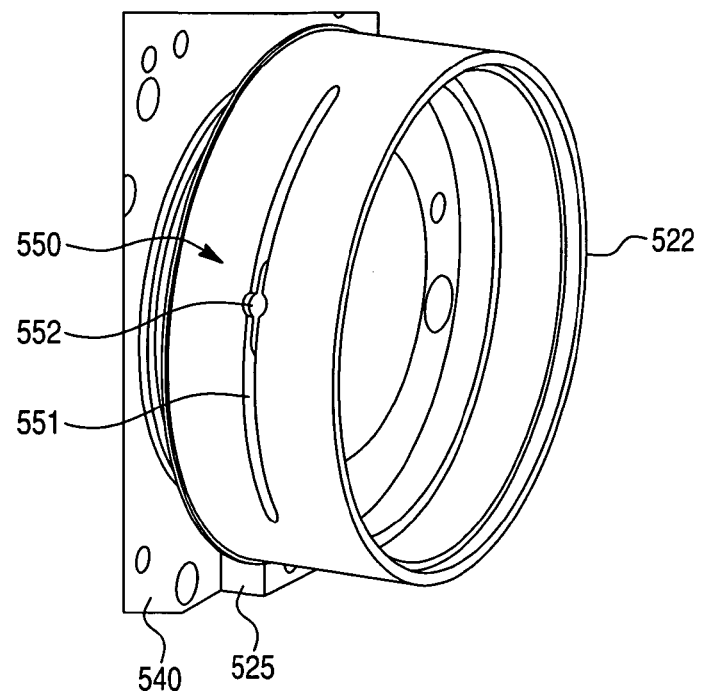
FIGS. 25A-25C are perspective views of an embodiment of a connection mechanism of the third module of FIG. 22A.
Figure 25B:
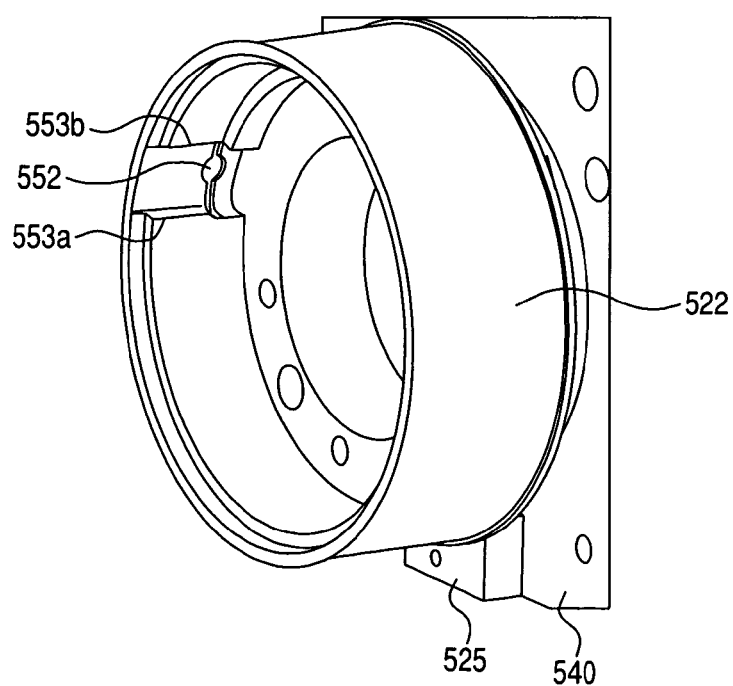
Figure 25C:
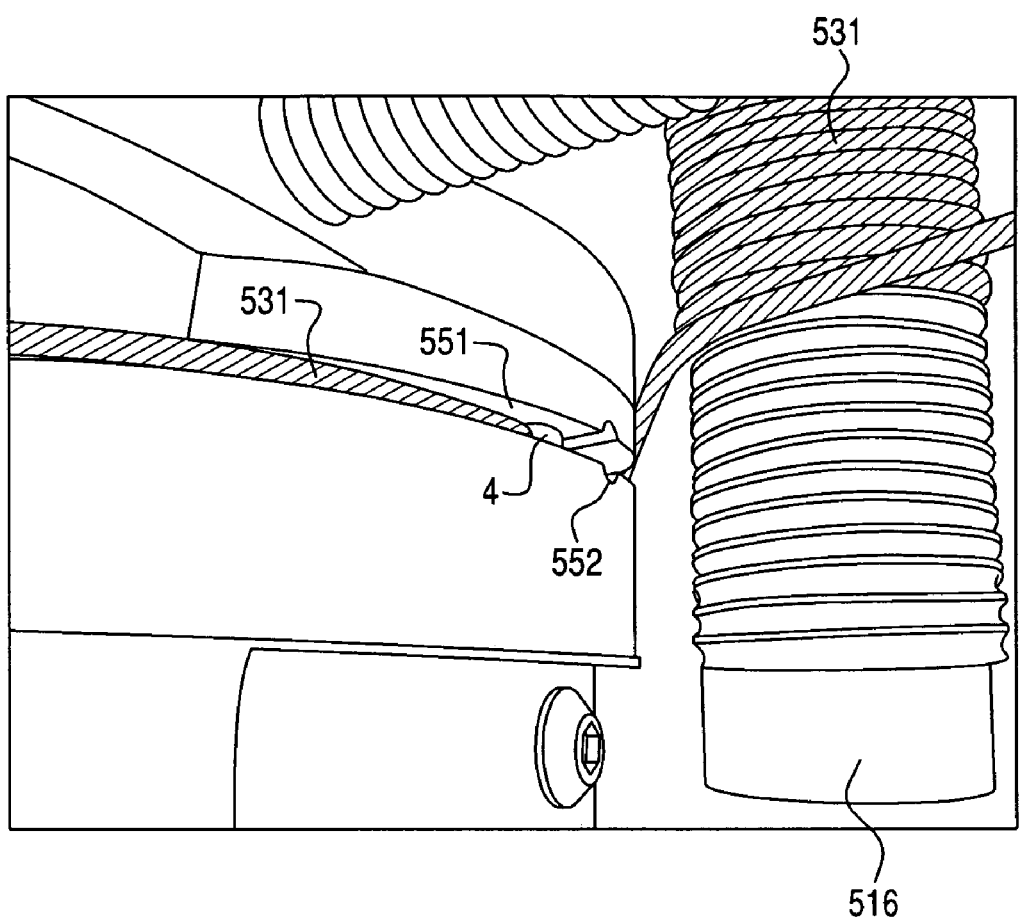

As shown in FIGS. 22A-C, the output pulley 522 includes the connection mechanism 550 for securing the cables 531, 532. The connection mechanism 550 may have any configuration suitable for securing the cables 531, 532. For example, the connection mechanism 550 could be similar to any of the connection mechanisms described herein. Additionally, in lieu of the adjustment member 570, the connection mechanism 550 could be configured to be adjustable to vary the tension force applied to each cable 531, 532. In one embodiment, the connection mechanism 550 is formed integrally with the output pulley 522. For example, the connection mechanism 550 comprises a slot 551 formed in the circumferential perimeter of the output pulley 522. The slot 551 includes an opening 552 that is large enough to receive a connector 4 (such as a stainless steel or brass ball as shown in FIG. 34) that is coupled to the distal end of each of the cables 531, 532. The slot 551 also includes a projection 553a adapted to restrain the connector 4 of one of the cables 531, 532 when the connector 4 is inserted into the opening 552 and tension is exerted on the cable in a direction away from the connector 4. Similarly, the slot 551 includes a projection 553b adapted to restrain the connector 4 of the other cable 531, 532 when the connector 4 is inserted into the opening 552 and tension is exerted on the cable in a direction away from the connector 4. As long as sufficient tension is maintained on a cable, the connector 4 is retained by the connection mechanism 550, as shown in FIG. 25C. A cable can be decoupled from the connection mechanism 550 by releasing tension from the cable. In this manner, the connection mechanism 550 is configured to removably secure the cables 531, 532 to the output pulley 522.

Sixth Joint Assembly

FIGS. 28A-28E show the fourth module D according to an embodiment of the invention. In this embodiment, the fourth module D includes the sixth joint assembly 600. As noted above, the sixth joint assembly 600 provides one rotational degree of freedom. Thus, the fourth module D provides the sixth degree of freedom of the robotic arm 10. The output motion of the fourth module D is similar to the motion of a human wrist joint. For this reason, the fourth module D is also referred to as the robot wrist.

FIGS. 28A-28E show the sixth joint assembly 600 according to an embodiment of the invention. The sixth joint assembly 600 is disposed on the joint output (i.e., the output pulley 522) of the fifth joint assembly 500 (as shown in FIG. 4) and thus moves with the joint output of the fifth joint assembly 500. Like the fourth joint assembly 400, the sixth joint assembly 600 has a two stage transmission. In one embodiment, the first stage of the transmission includes a first component 601a (which includes a drive member 610a), a second component 602a (which includes a driven member 620a), and an at least partially flexible transmission 603a. Similarly, the second stage of the transmission includes a first component 601b (which includes a drive member 610b), a second component 602b (which includes a driven member 620b), and an at least partially flexible transmission 603b. As with in the fourth joint assembly 400, the sixth joint assembly 600 includes both active and passive drive members.

Figure 28A:
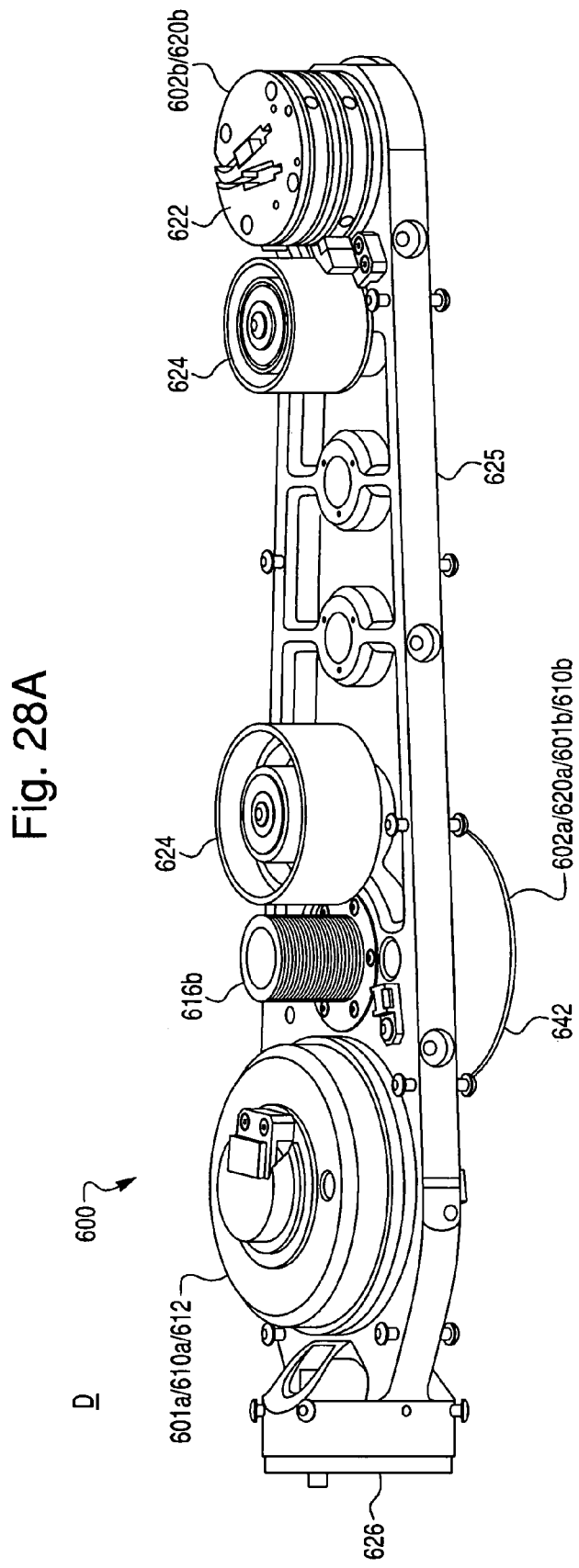
FIG. 28A is a top perspective view of a fourth module according to an embodiment.
Figure 28B:
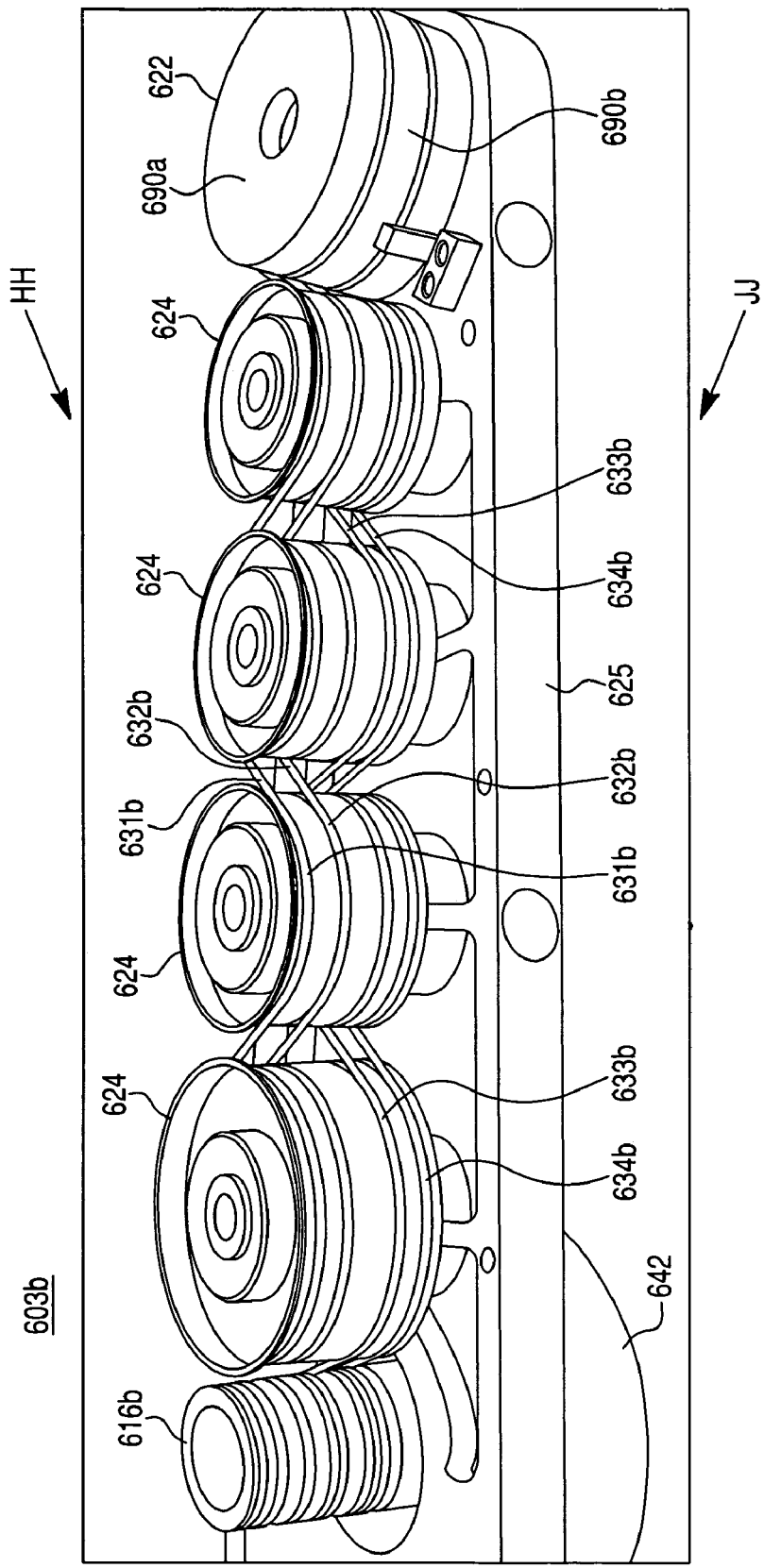
FIG. 28B is a perspective view of an embodiment of a flexible transmission of the fourth module of FIG. 28A.
Figure 28C:
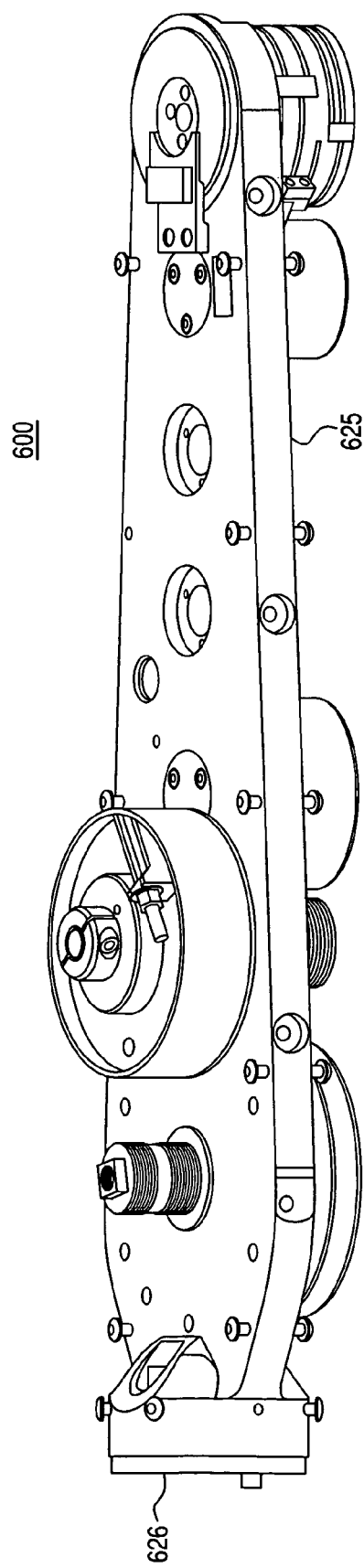
FIG. 28C is a bottom perspective view of the fourth module of FIG. 28A
Figure 28D:
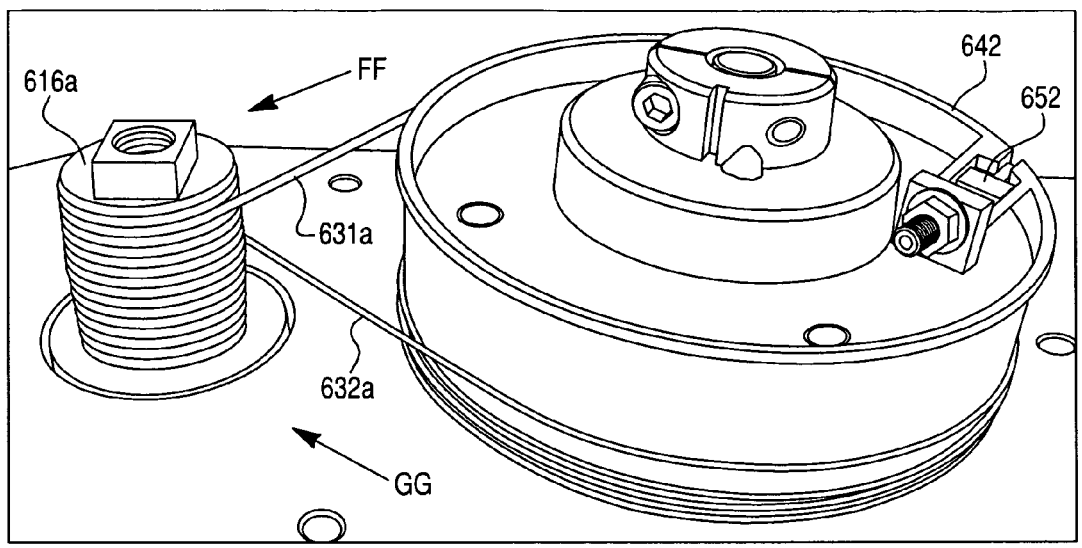
FIG. 28D is a perspective view of an embodiment of a flexible transmission of the fourth module of FIG. 28A.
Figure 28E:
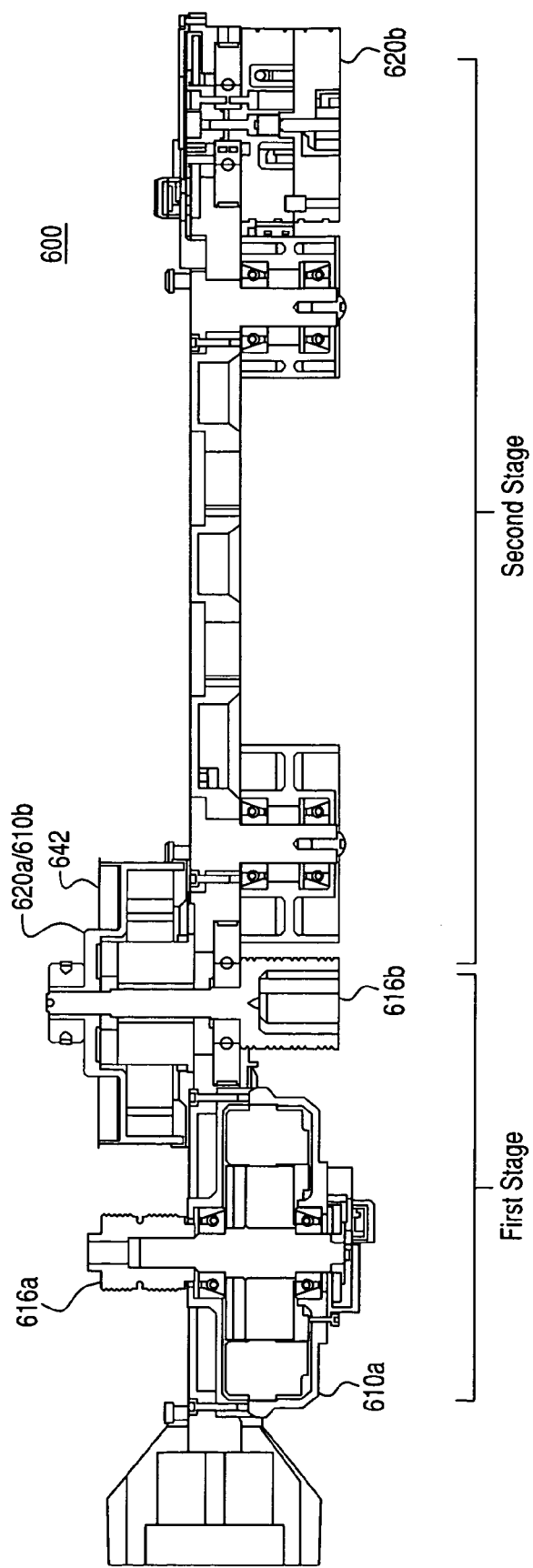
FIG. 28E is a cross-sectional view of the fourth module of FIG. 28A.

As shown in FIG. 28E, the six joint assembly 600 incorporates a first stage transmission and a second stage transmission. The first stage transmission includes the drive member 610a that drives the driven member 620a via the flexible transmission 603a. Similarly, the second stage transmission includes the drive member 610b that drives the driven member 620b via the flexible transmission 603b. As can be seen, the first and second stage transmissions share a component in common. Specifically, the driven member 620a and the drive member 610b are the same component. Because the drive member 610a imparts motion to the drive member 610b, the drive member 610b is a passive drive member as defined above.

According to an embodiment, the drive member 610a is a drive motor 612 (i.e., an active drive member) having a first stage pinion 616a, and the driven member 620a is an intermediate pulley assembly 642 having a second stage pinion 616b. The flexible transmission 603a includes a plurality of cables that are connected to the first stage pinion 616a and the intermediate pulley assembly 642 and transmit force and/or torque from the drive motor 612 to the intermediate pulley assembly 642. As can be seen in FIG. 28A, the intermediate pulley assembly 642 is also the drive member 610b (i.e., a passive drive member). The flexible transmission 603b includes a plurality of cables that are connected to the second stage pinion 616b and the driven member 620b and transmit force and/or torque from the intermediate pulley assembly 642 to the driven member 620b. The driven member 620b is an output pulley assembly 622, which is the joint output of the sixth joint assembly 600. The second stage transmission also incorporates multiple idler pulleys 624, which are non-driven pulleys included, for example, to reduce the amount of unsupported cable in the second stage transmission, minimize radial loads on the bearings that support drive train components, and minimize bending moments on a rigid frame 625 that supports the drive train components. As shown in FIG. 28B, the cables of the second stage transmission are routed in a serpentine fashion around the idler pulleys 624. The drive reduction of the first stage transmission is the ratio of the diameter of the intermediate pulley assembly 642 to the diameter of the first stage pinion 616a. This drive reduction causes the rotation angle of the intermediate pulley assembly 642 to be less than the rotational angle of the first stage pinion 616a by the inverse of the value of the drive reduction and also causes the torque transmitted between the drive motor 612 and the intermediate pulley assembly 642 to be higher by the ratio of the drive reduction. Similarly, the drive reduction of the second stage transmission is the ratio of the diameter of the output pulley assembly 622 to the diameter of the second stage pinion 616b. The total drive reduction of the sixth joint assembly 600 is the drive reduction of the first stage transmission multiplied by the drive reduction of the second stage transmission.

The first and second stage transmissions of the sixth joint assembly 600 are disposed on the rigid frame 625 having a proximal end with an attachment flange 626 that is mounted on the output pulley 522 of the fifth joint assembly 500 (e.g., using mechanical fasteners). The rigid frame 625 supports the drive components and has a length (e.g., from the attachment flange 626 to a center of rotation of the driven member 620b) sufficient to ensure that the sixth joint assembly 600 provides the appropriate range of motion and "reach" needed by the surgeon to manipulate the robotic arm 10 to access the relevant portions of the patient's anatomy. The rigid frame 625 can be made of a rigid material, such as aluminum, a composite (e.g., a Kevlar® composite), or the like. Structural covers 627 (shown in FIG. 3) can be mounted to the rigid frame 625 to provide additional stiffness to resist bending and/or torsion caused, for example, by forces applied by the surgeon as the surgeon manipulates the end effector 700. Preferably, the structural covers 627 include access openings 627a to facilitate inspection of the first and second transmissions and permit adjustment of cable tension and encoder system components without having to remove the structural covers 627.

The flexible transmissions 603a, 603b of the sixth joint assembly 600 are similar to the flexible transmission 103 of the first joint assembly 100. Each flexible transmission 603a, 603b includes tension elements (e.g., cables or cords) and may optionally include redundant tension elements. In one embodiment, the flexible transmission 603b includes redundant tension elements while the flexible transmission 603a is non-redundant. For example, in this embodiment, the flexible transmission 603a includes a first transmission element comprising a first cable 631a and a second transmission element comprising a second cable 632a. Although the cables 631a, 632a can be configured in a variety of ways to impart motion to the intermediate pulley assembly 642, in this embodiment, each of the cables 631a, 632a has a proximal end connected to the drive motor 612 (i.e., at the pinion 616a) and a distal end connected to the intermediate pulley assembly 642. The cables 631a, 632a are not redundant because each cable 631a, 632a performs a different function. Specifically, the cable 631a functions to exert a tension force on the intermediate pulley assembly 642 in a direction FF (shown in FIG. 28D) when the pinion 616a rotates to wind the cable 631a onto the pinion 616a. In contrast, the cable 632a functions to exert a tension force on the intermediate pulley assembly 642 in a direction GG when the pinion 616a rotates to wind the cable 632a onto the pinion 616a. Thus, the flexible transmission 603a utilizes two cables that are not redundant in function. In contrast, the flexible transmission 603b includes a first transmission element having a first plurality of tension elements (transmission sub-elements) and a second transmission element having a second plurality of tension elements (transmission sub-elements). In this embodiment, the first transmission element is a first cable set that includes the first plurality of tension elements, which includes a first cable 631b and a second cable 632b. Similarly, the second transmission element is a second cable set that includes the second plurality of tension elements, which includes a third cable 633b and a fourth cable 634b. Thus, the flexible transmission 603b includes redundant cables the advantages of which are described above in connection with the first joint assembly 100. For example, the cables 631b, 632b are redundant because each cable 631b, 632b performs the same function of exerting a tension force on the output pulley assembly 622 in a direction HH (shown in FIG. 28B) when the pinion 616b rotates to wind the cables 631b, 632b onto the pinion 616b. Similarly, the cables 633b, 634b are redundant because each cable 633b, 634b performs the same function of exerting a tension force on the output pulley assembly 622 in a direction JJ when the pinion 616b rotates to wind the cables 633b, 634b onto the pinion 616*b*. Although the cables 631*b*, 632*b*, 633*b*, 634*b* can be configured in a variety of ways to impart motion to the output pulley assembly 622, in this embodiment, each of the cables 631*b*, 632*b*, 633*b*, 634*b* has a proximal end connected to the intermediate pulley assembly 642 and a distal end connected to the output pulley assembly 622. The cables 631*a*, 632*a*, 631*b*, 632*b*, 633*b*, 634*b* may be any cables appropriate for use in a robotic system but are preferably tungsten cables.

As discussed above in connection with the fourth joint assembly 400, one potential disadvantage of using a cable transmission is the need to pre-tension the cables, which results in large cable tension forces being imparted to the drive train component bearings and their support structure. Accordingly, the cables of the first and second stage transmissions are preferably configured to minimize such loads by utilizing the "crossover" (or "tangent wrap") configuration described above in connection with the fourth joint assembly 400. For example, as shown in FIG. 28D, the cables of the first stage transmission are arranged so the cable 531*a* crosses the cable 532*a* after the cables lead off the drive motor 612 but before they contact the intermediate pulley assembly 642. As shown in FIG. 28B, the cables 531*b*, 532*b*, 533*b*, 534*b* of the second stage transmission are similarly arranged.

Motive force is provided to the sixth joint assembly 600 by the drive member 610*a*. As noted above, the drive member 610*a* includes the drive motor 612, which imparts rotational motion to the intermediate pulley assembly 642 via the flexible transmission 603*a*. The drive motor 612 may be any motor suitable for driving the intermediate pulley assembly 642. In one embodiment, the drive motor 612 is integral with the rigid frame 625 similar to the drive motor 412 of the fourth joint assembly 400. In another embodiment, the drive motor 612 is an independent assembly (shown in FIG. 29) that is bolted to the rigid frame 625. The drive motor 612 includes a stator 618 along with a rotor 619 that is bonded to a motor shaft 614. Preferably, the drive motor 612 includes a motor encoder configured to measure angular rotation of the motor shaft 614. The motor encoder may be similar to the encoder measurement systems discussed above in connection with the drive motors of the other joint assemblies. For example, the motor encoder includes an encoder scale 615*a* that rotates with the motor shaft 614 and an encoder read head 615*b* (mounted on a bracket) that reads the encoder scale 615*a*. Thus, the motor encoder enables measurement of the angular rotation of the motor shaft 614, which, as discussed above in connection with the joint assembly 100 can be compared with the angular rotation of the joint output (e.g., as measured by a joint encoder) to determine whether the integrity of the flexible transmission of the sixth joint assembly 600 has been compromised. The drive motor 612 may optionally include a motor brake as described above in connection with the first joint assembly 100.

The motor shaft 614 of the drive motor 612 is bonded to the rotor 619, and the first stage pinion 616*a* extends from the motor shaft 614. The first stage pinion 616*a* may be coupled to or integral with the motor shaft 614 and includes attachment elements 670 for securing the proximal ends of the cables 631*a*, 632*a*. An attachment element 670 may have any configuration suitable for securely anchoring a cable to the pinion 616*a*. For example, an attachment element 670 may be similar to any of the attachment elements described herein in connection with the other joint assemblies. In one embodiment, the proximal end of each cable 631*a*, 632*a* has a connector 4 (such as a stainless steel or brass ball as shown in FIG. 34) coupled thereto, and the attachment element 670 is configured to seat the connector 4 when the cable is under tension in the same manner described above in connection with the attachment elements of the fourth joint assembly 400.

Figure 29:
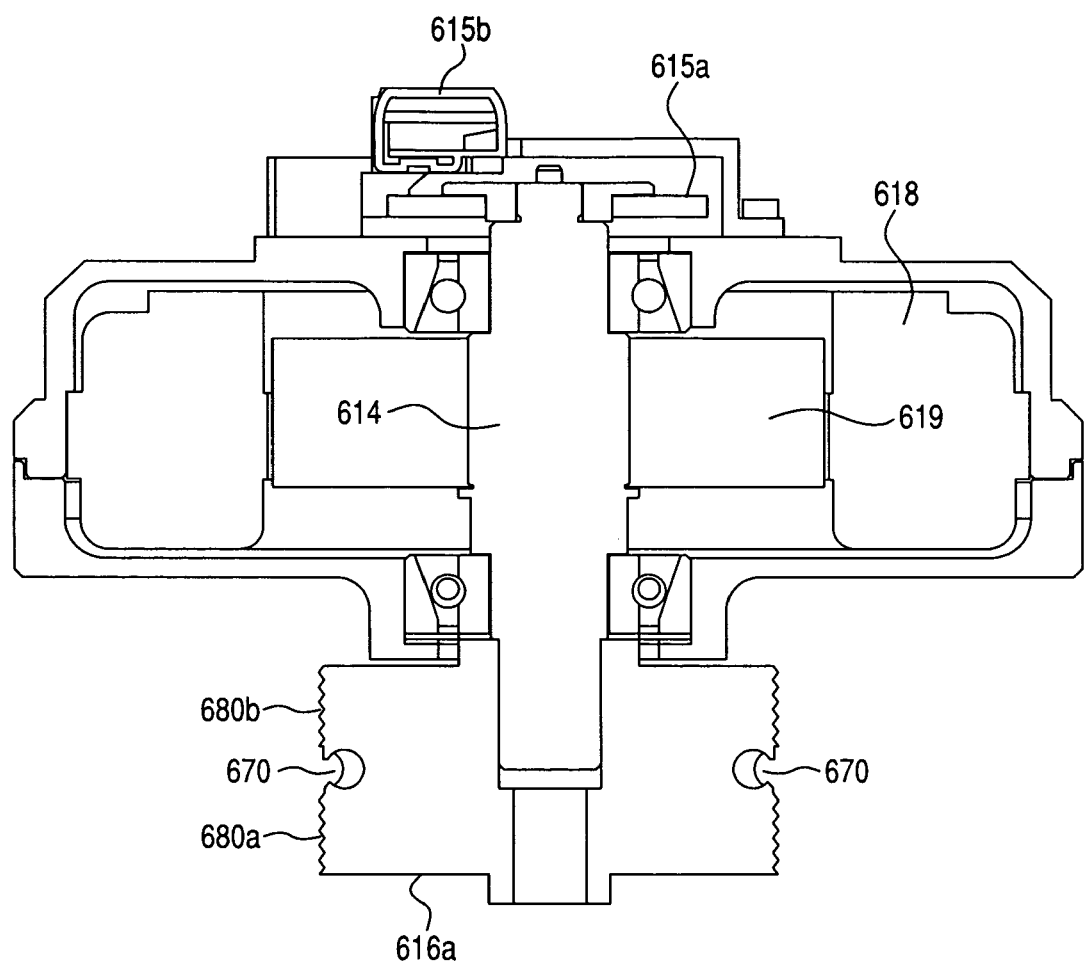
FIG. 29 is a cross-sectional view of an embodiment a drive member of the fourth module of FIG. 28A.

As shown in FIG. 29, the pinion 616*a* includes two attachments element 670 disposed at approximately a midpoint of the first stage pinion 616*a*. Each cable 631*a*, 632*a* has a proximal end connected to an attachment element 670 and is wound around the pinion 616*a*, as shown in FIG. 28D. For each cable 631*a*, 632*a*, the portion of the cable that exits the attachment element 670 engages a guide 680*a*, 680*b*, respectively. The guides 680*a*, 680*b* may be similar to the guide described above in connection with the pinion 416*a* of the fourth joint assembly 400 (i.e., a single spiral groove or "single helix" arrangement). In the embodiment of FIG. 29, the first guide 480*a* extends from the attachment element 670 along a length of the first stage pinion 616*a* toward a proximal end of the pinion 616*a* and receives one of the cables 631*a*, 632*a*. Similarly, the second guide 480*b* extends from a different attachment element 670 along a length of the first stage pinion 616*a* toward a distal end of the pinion 616*a* and received the other cable 631*a*, 632*a*. When received in the guides 480*a*, 480*b*, the cables 631*a*, 632*a* wind around the first stage pinion 616*a* in opposite directions and eventually lead off the first stage pinion 616*a* and wrap circumferentially around the intermediate pulley assembly 642 in opposite directions before terminating at a connection mechanism disposed on the intermediate pulley assembly 642.

The connection mechanism may be integral with or coupled to the intermediate pulley assembly 642 and may have any configuration suitable for securely anchoring the cables 631*a*, 632*a*. For example, the connection mechanism may be similar to one or more of the connection mechanisms described herein in connection with the other joint assemblies. In one embodiment, the connection mechanism includes an upper coupling component 652 to which the cable 631*a* is coupled and a lower coupling component (not shown) to which the cable 632*a* is coupled. The upper coupling component 652 is similar to the coupling component on the pulley assembly 442 of the fourth joint assembly 400, including incorporation of a threaded rod, tension nut, and lock nut that function as an adjustment member (or floating tensioner) for varying a tension force applied to the cable 631*a*. In contrast, the lower coupling component (not shown) includes a grooved portion that captures a connector 4 (such as a stainless steel or brass ball as shown in FIG. 34) on the distal end of the cable 632*a* in a manner similar to the attachment elements of the first stage pinion 616*a*. Although the lower coupling component does not have a mechanism for tensioning the cable 632*a*, because (a) the cables 631*a*, 632*a* are both coupled to the first stage pinion 616*a* and the intermediate pulley assembly 642 and (b) the intermediate pulley assembly 642 is able to rotate, adjustment of the tension force applied to the cable 631*a* automatically results in adjustment of the tension force applied to the cable 632*a* in accordance with principles of equilibrium. As a result, the two separate cables 631*a*, 632*a* of the sixth joint assembly 600 can both be tensioned by adjusting only one tensioning mechanism.

Rotation of the intermediate pulley assembly 642 occurs when the drive motor 612 actuates causing the first stage pinion 616*a* to rotate. When the first stage pinion 616*a* rotates, the cable 631*a* winds around (or unwinds from) the pinion 616*a* and the cable 632*a* conversely unwinds from (or winds around) the pinion 616*a* depending on the direction of rotation. Because the distal ends of the cables 631*a*, 632*a* are coupled to the intermediate pulley assembly 642, the winding and unwinding of the cables 631*a*, 632*a* exerts force and/or torque on the intermediate pulley assembly 642 that causes the intermediate pulley assembly 642 to rotate. As explained above, the intermediate pulley assembly 642 is a passive drive member that imparts rotational motion to the output pulley assembly 622 via the flexible transmission 603b. In particular, the intermediate pulley assembly 642 includes the second stage pinion 616b to which proximal ends of the cables 631b, 632b, 633b, 634b are coupled. When the intermediate pulley assembly 642 rotates, the cables 631b, 632b wind around (or unwind from) the second stage pinion 616b and the cables 633b, 634b conversely unwind from (or wind around) the second stage pinion 616b depending on the direction of rotation. Because the distal ends of the cables 631b, 632b, 633b, 634b are coupled to the output pulley assembly 622, the winding and unwinding of the cables 631b, 632b, 633b, 634b exerts force and/or torque on the output pulley assembly 622 that causes the output pulley assembly 622 to rotate thereby providing the sixth rotational degree of freedom J6 shown in FIG. 2.

The intermediate pulley assembly 642 preferably includes a pulley brake 611 configured to inhibit rotation of the second stage pinion 616b. The pulley brake 611 may be any suitable brake assembly but is preferably a permanent magnet type brake manufactured by Kendrion Electromagnetic Group of Germany. The brake 611 is internal to the intermediate pulley assembly 642 in the same manner as described above in connection with the pulley brake 411 of the fourth joint assembly 400 (shown in FIG. 20) and operates in the same manner. The pulley brake 611 is a failsafe mechanism that can be triggered, for example, in response to a fault signal. Additionally, as described above in connection with the first joint assembly 100, the incorporation of a brake on the second stage drive member along with redundant cables in the second stage flexible transmission 603b, enables the joint output to be unbraked.

The second stage pinion 616b includes attachment elements for securing the proximal ends of the cables 631b, 632b, 633b, 634b. An attachment element may have any configuration suitable for securely anchoring a cable to the pinion 616b. For example, the attachment element may be similar to any of the attachment elements described herein in connection with the other joint assemblies. In one embodiment, the attachment elements are similar to the attachment elements 670 of the first stage pinion 616a, and the proximal ends of the cables 631b, 632b, 633b, 634b include connectors 4 that seat in the attachment elements in the same manner described above in connection with the first stage pinion 616a. In contrast to the first stage pinion 616a (which includes two attachment elements 670 for two cables), the second stage pinion 616b includes four attachment elements 670a, 670b, 670c, 670d disposed along a length of the second stage pinion 616b to accommodate the four cables 631b, 632b, 633b, 634b. As shown in FIG. 30, the cables 631b, 632b couple to the attachment elements 670a, 670b, respectively, and the cables 633b, 634b couple to the attachment elements 670c, 670d, respectively. For each attachment element, the portion of the cable that exits the attachment element engages a guide. The guide may be similar to the guide described above in connection with the first stage pinion 616a except the guide is configured for use with redundant cables as opposed to single cables. For example, in this embodiment, the guide includes a first guide 680c that receives and guides the cable 631b, a second guide 680d that receives and guides the cable 632b, a third guide 680e that receives and guides the cable 633b, and a fourth guide 680f that receives and guides the cable 634b. Each of the guides 680c, 680d, 680e, 680f comprises a single spiral (e.g., helical) groove (or "single helix" arrangement) that extends along a portion of the length of the second stage pinion 616b. Alternatively, the second stage pinion 616b could incorporate a double helix arrangement as described above in connection with the pinion 116 of the first joint assembly 100. As shown in FIG. 28B, the cables 631b, 632b and the cables 633b, 634b wind around the second stage pinion 616b in opposite directions, lead off the second stage pinion 616b, and wrap circumferentially around a portion of each of the idler pulleys 624. The cables 631b, 632b, 633b, 634b lead off the last idler pulley 624 and onto the output pulley assembly 622 where the cables 631b, 632b, 633b, 634b terminate at a connection mechanism disposed on the output pulley assembly 622. The idler pulleys 424 are intermediate components disposed between the drive member 610b and the driven member 620b. In this manner, the first transmission element (e.g., the cables 631b, 632b) and the second transmission element (e.g., the cables 633b, 634b) contact each of a plurality of intermediate components (e.g., the idler pulleys 424) between the coupling of the first transmission element to the drive member 610b and the coupling of the first transmission element to the driven member 620b.

The idler pulleys 424 are non-driven pulleys included, for example, to reduce the amount of unsupported cable in the second stage transmission. Although this embodiment includes four idler pulleys 424, other embodiments may include more idler pulleys, fewer idler pulleys, or no idler pulleys. Whether to include an idler pulley(s) can be determined based, for example, on transmission configuration details, such as the distance between the drive member and the driven member. The idler pulley 424 may be any pulley known in the art for supporting a tension element in a tension element drive transmission. Advantageously, the combined use of idler pulleys and the crossover cable configuration enables transmission of power over a distance while minimizing drive friction and structural loading due to cable tension, which allows the design of a flexible transmission that is backdrivable with extremely low backlash.

Figure 31A:
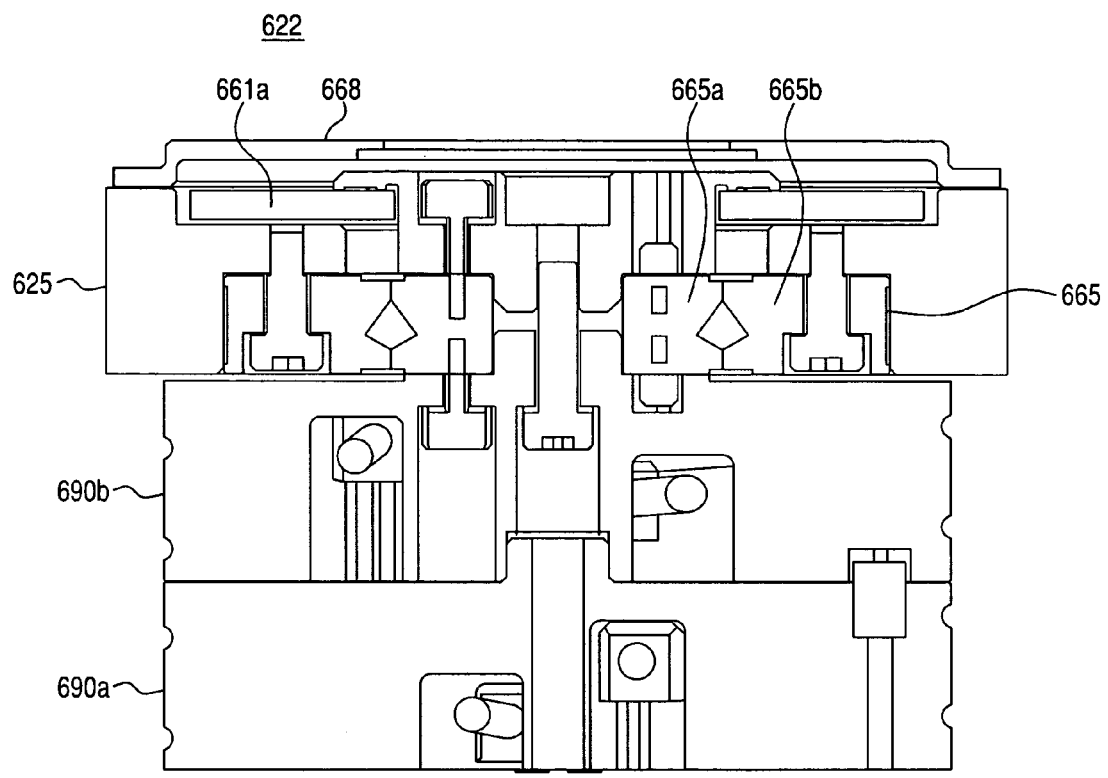
FIG. 31A is a cross-sectional view of an embodiment of a driven member of the fourth module of FIG. 28A.

The output pulley assembly 622 is the driven member 620b of the second stage transmission and is driven by the intermediate pulley assembly 642 via the flexible transmission 603b. The output pulley assembly 622 is the joint output for the sixth joint assembly 600. In one embodiment the driven member 620b includes a first component and a second component coupled to the first component. For example, as shown in FIG. 31A, the output pulley assembly 622 includes a first pulley 690a that is disposed on and coupled to a second pulley 690b. The pulleys 690a, 690b are coupled to the rigid frame 625 via a cross roller bearing 665. An outer race 665b of the cross roller bearing 665 is coupled to the rigid frame 625 with mechanical fasteners, and an inner race 665a of the cross roller bearing 665 is coupled to the output pulley assembly 622 with mechanical fasteners. As shown in FIG. 28B, the cables 631b, 632b wrap onto the pulley 690a, and the cables 633b, 634b wrap onto the pulley 690b.

As with the other joint assemblies, the joint output (in this case, the output pulley assembly 622) of the sixth joint assembly 600 preferably includes a joint encoder configured to measure angular rotation of the joint output. Any suitable encoder system can be used. In one embodiment, as shown in FIGS. 31A and 31D, the joint encoder includes an encoder scale 661a mounted to the inner race 665a of the cross roller bearing 665 through a spacer and an encoder read head 661b coupled to the rigid frame 625. A protective cover 668 for the encoder scale 661a may also be utilized. As the output pulley assembly 622 rotates, markings on the encoder scale 661a are read by the encoder read head 661b to determine angular position of the output pulley assembly 622. For relative encoder systems, an encoder index mark is also included as explained above in connection with the joint encoder of the first joint assembly 100. Based on data from the joint encoder, the rotational output can be compared to the rotational input from the drive motor 612 (measured by the motor encoder) to determine whether the integrity of the flexible transmission has been compromised.

Figure 31B:
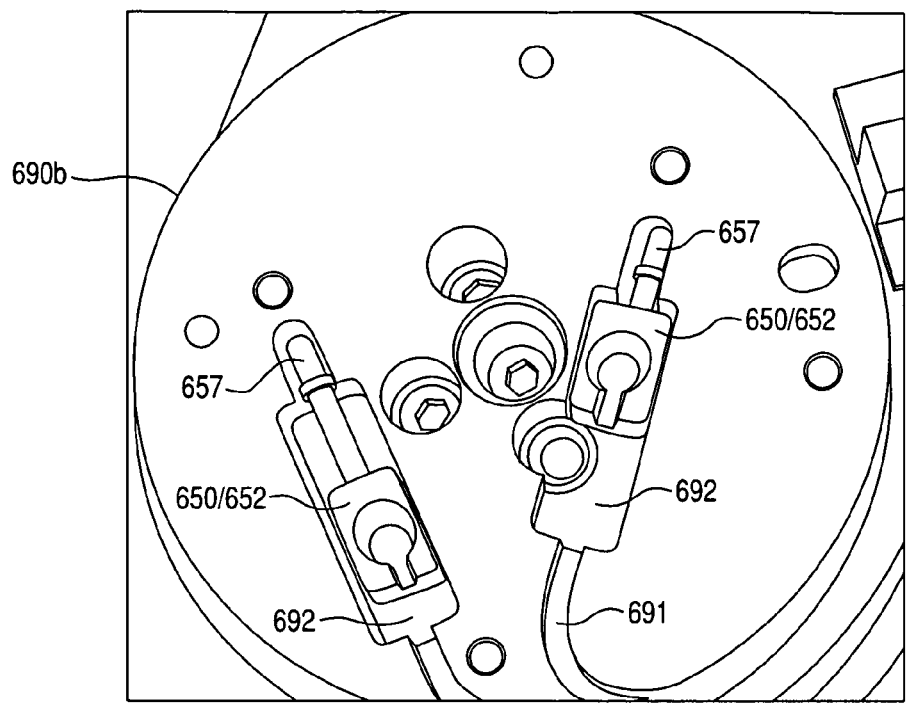
FIG. 31B is a top view of an embodiment of a pulley of the fourth module of FIG. 28A.
Figure 31C:
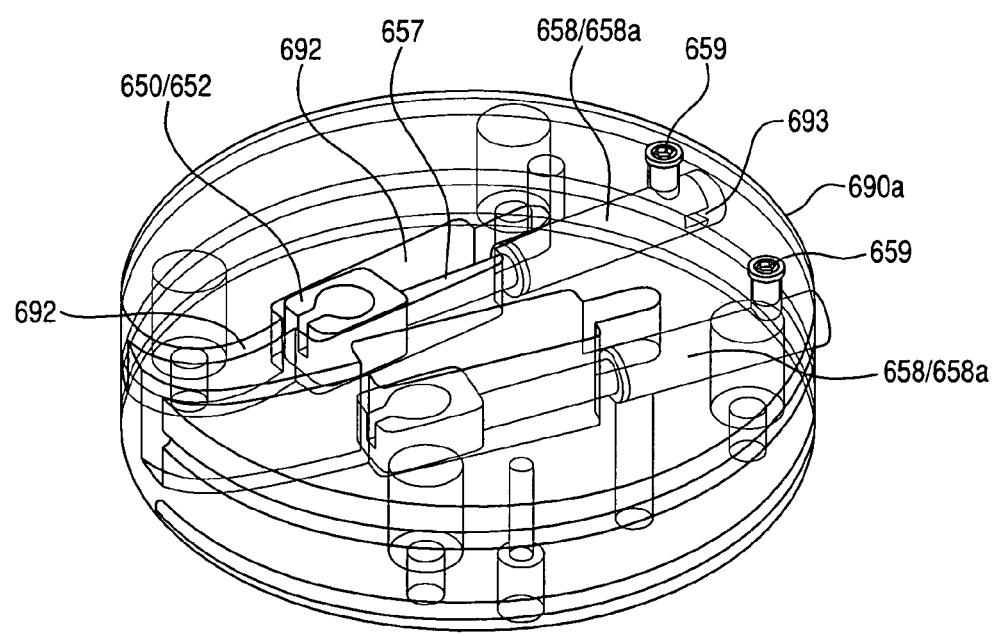
FIG. 31C is a perspective view of an embodiment of a pulley of the fourth module of FIG. 28A.
Figure 31D:
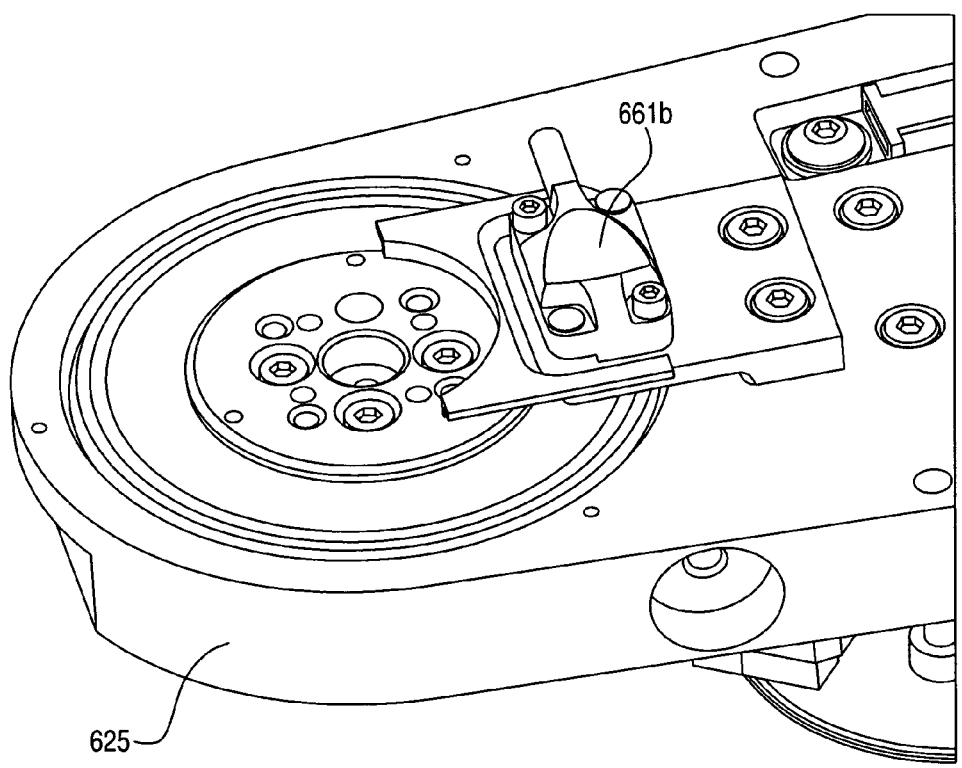
FIG. 31D is a perspective view of an embodiment of a joint encoder of the fourth module of FIG. 28A.

As shown in FIGS. 31B and 31C, the output pulley assembly 622 includes four connection mechanisms 650 for securing each of the cables 631b, 632b, 633b, 634b. The connection mechanisms 650 may be integral with or coupled to the output pulley assembly 622 and may have any configuration suitable for securely anchoring the cables. For example, the connection mechanisms 650 may be similar to one or more of the connection mechanisms described herein in connection with the other joint assemblies. According to an embodiment, two connection mechanisms 650 are disposed on the pulley 690a, and two connection mechanisms 650 are disposed on the pulley 690b. Each connection mechanism 650 is located inwardly of a circumferential perimeter of the associated pulley 690a, 690b on which it is disposed and is recessed below a face of the associated pulley 690a, 690b. As best shown in FIG. 31A, the first component (i.e., the pulley 690a) and the second component (i.e., the pulley 690b) enclose at least some of the connection mechanisms 650 (e.g., the connection mechanisms 650 disposed on the pulley 690b). To enable each recessed connection mechanism 650 to mate with its respective cable, the associated pulley 690a, 690b includes a recess 691 configured to receive a portion of the flexible transmission 603b (i.e., the cable that mates to the connection mechanism 650). The connection mechanisms 650 are preferably similar to the coupling components on the pulley assembly 442 of the fourth joint assembly 400 and function in the same manner. For example, each connection mechanism 650 includes a coupling member 652 and the associated pulley 690a, 690b includes a slot 692 (or recess) configured to receive the coupling member 652. The coupling member 652 and slot 692 are preferably similar to the coupling member and slot described above in connection with the connection mechanism 150 of the first joint assembly 100, including incorporating a threaded rod 657 and tension nut 658 that function as an adjustment member (or floating tensioner) for varying a tension force applied to the cable. Because each connection mechanism 650 is recessed into its associated pulley 690a, 690b, each tension nut 658 of the output pulley assembly 622 is elongated to enable a user to access the tension nut. For example, an elongated portion 658a of the tension nut 658 is received in a channel 693. The channel 693 is configured to enable a user to adjust the connection mechanism 650 to vary the tension force applied to the flexible transmission 603b. For example, as shown in FIG. 31C, the elongated portion 658a provides access for a user to tension the tension nuts. Set screws 659 prevent loosening of the tension nuts 658 (e.g., due to vibration). In this manner, the connection mechanism is configured to be adjustable without decoupling the pulley 690a and the pulley 690b.

As shown in FIGS. 2 and 3, the end effector 700 of the robotic arm 10 attaches to the joint output (i.e., the output pulley assembly 622) of the sixth joint assembly 600 via a mounting flange 705 that is rigidly attached to the output pulley assembly 622 through a cross roller bearing (not shown). In one embodiment, the mounting flange 705 and mating surface of the end effector 700 form a semi-kinematic coupling as described in U.S. patent application Ser. No. 12/644,964, entitled DEVICE THAT CAN BE ASSEMBLED BY COUPLING, filed Dec. 22, 2009, which is hereby incorporated by reference herein in its entirety. The end effector 700 may be any end effector appropriate for the application for which the robotic arm 10 will be used. In one embodiment, the end effector is an end effector as described in U.S. patent application Ser. No. 12/644,990, entitled END EFFECTOR WITH RELEASE ACTUATOR, filed Dec. 22, 2009, which is hereby incorporated by reference herein in its entirety. A surgical tool 710 (such as a cutting burr) is coupled to the end effector 700. In operation, the surgeon grasps and moves the end effector 700 to perform a surgical task on a patient, such as cutting bone during a joint replacement procedure with the surgical tool 710. During the surgical procedure, the robotic arm 10 provides haptic feedback (e.g., tactile or force feedback) to the surgeon to guide the surgeon in performing the surgical task, as described, for example in U.S. patent application Ser. No. 11/357,197, filed Feb. 21, 2006 (Pub. No. US 2006/0142657), which is hereby incorporated by reference herein in its entirety.

Triple Connector Cable

The flexible transmission embodiments described above in connection with the joint assemblies 100, 200, 300, 400, 500, 600 utilize cables where a cable comprises a length of cable LL with a first connector 4 (such as a swaged ball, threaded rod, or other connection mechanism) disposed on a proximal end LP of the cable LL and a second connector 4 disposed on a distal end LD of the cable LL, as shown in FIG. 34. For ease of reference, a cable with two connectors may be referred to as a "double connector" cable. The proximal end LP of a double connector cable is typically connected to a drive member and the distal end LD of the double connector cable is typically connected to a driven member. In a non-redundant configuration (e.g., the first stage of the sixth joint assembly 600), only two double connector cables are used, i.e., one to pull the driven member in one direction and another to pull the driven member in another direction. When redundancy is desired (e.g., the second stage of the sixth joint assembly 600), two cable sets are used where each cable set includes two double connector cables that are redundant. In other words, the first and second plurality of transmission sub-elements (i.e., the first and second cable sets) each include at least two cables, where each cable has a first end connected to the drive member and a second end connected to the second component (in this case, the main drive). One cable set pulls the driven member in one direction, and the other cable set pulls the driven member in another direction.

Figure 35:
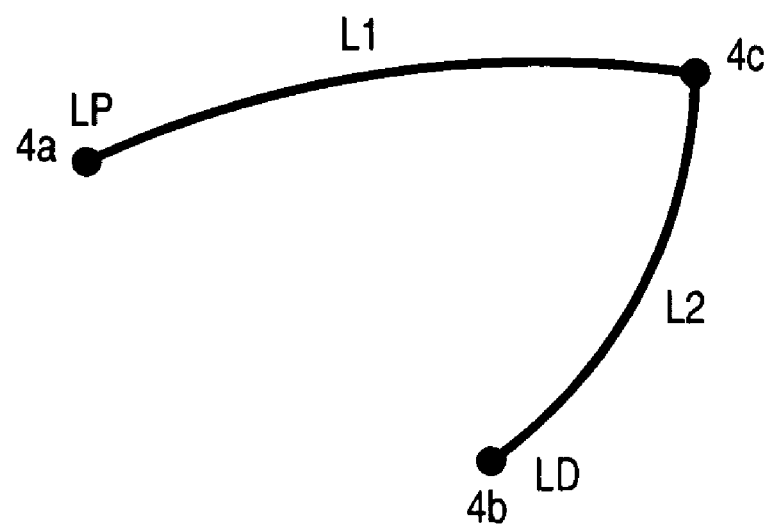
FIG. 35 is a schematic of a triple connector tension element according to an embodiment.

Other cable configurations can also be used. For example, in an alternative embodiment, a cable includes three connectors, as shown in FIG. 35. For ease of reference, a cable with three connectors may be referred to as a "triple connector" cable. In this embodiment, the triple connector cable includes a cable having a first connector 4a disposed on a proximal end LD of the cable, a second connector 4b disposed on a distal end LD of the cable, and a third connector 4c disposed between the first and second connectors 4a, 4b. This results in a triple connector cable having a first cable segment L1 disposed between the first and third connectors 4a, 4c and a second cable segment L2 disposed between the second and third connectors. The first and second cable segments L1, L2 may be part of a continuous length of cable or may be separate cables.

Figure 36A:
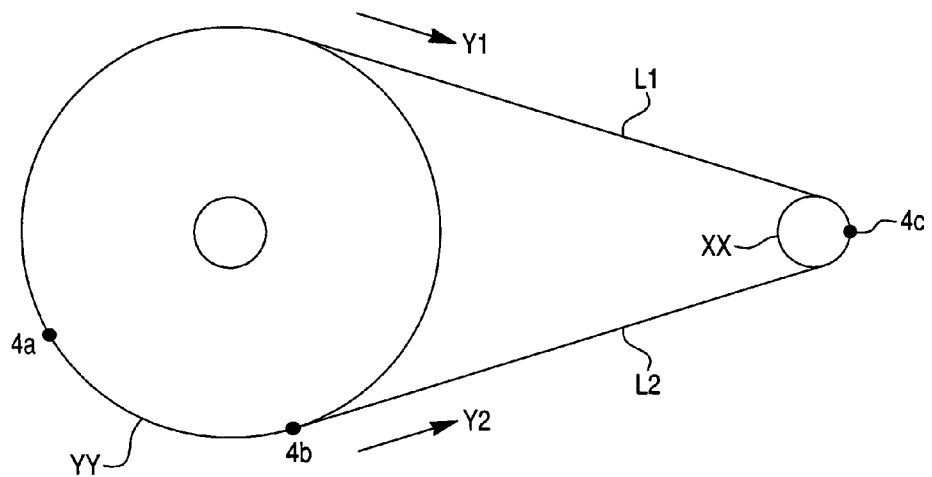
FIG. 36A is a schematic of the triple connector tension element of FIG. 35 coupled to a drive member and a driven member according to an embodiment.

One advantage of using a triple connector cable is that one triple connector cable can replace two double connector cables. Thus, instead of using two double connector cables to form a plurality of transmission sub-elements, one triple connector cable can be used. In one embodiment, the plurality of transmission sub-elements can be a triple connector cable that includes the first and second cable segments L1, L2 connected to a first component (i.e., a drive member) and to the third connector 4c, where the third connector 4c is coupled to a second component (e.g., a driven member). Conversely, a plurality of transmission sub-elements can be a triple connector cable that includes the first and second cable segments L1, L2 coupled to the second component (e.g., a driven member) and to the third connector 4c, where the third connector 4c is coupled to the first component (i.e., a drive member). For example, as illustrated in FIG. 36A, the third connector 4c of the triple connector cable can be engaged with a drive member XX (or a driven member), and the first and second cable connectors 4a, 4b can be engaged with a driven member YY (or a drive member). Engagement can be accomplished using any suitable means, such as any of the attachment elements or connection mechanisms described above in connection with the joint assemblies 100, 200, 300, 400, 500, 600. As shown in FIG. 36A, the first cable segment L1 pulls the driven member YY in a direction Y1 when the drive member XX rotates to wind the first cable segment L1 about the drive member XX, and the second cable segment L2 pulls the driven member YY in a direction Y2 when the drive member XX rotates to wind the second cable segment L2 about the drive member XX. In the embodiment of FIG. 36A, using one triple connector cable creates a non-redundant configuration. Redundancy can be achieved by adding a second triple cable connector.

Figure 36B:
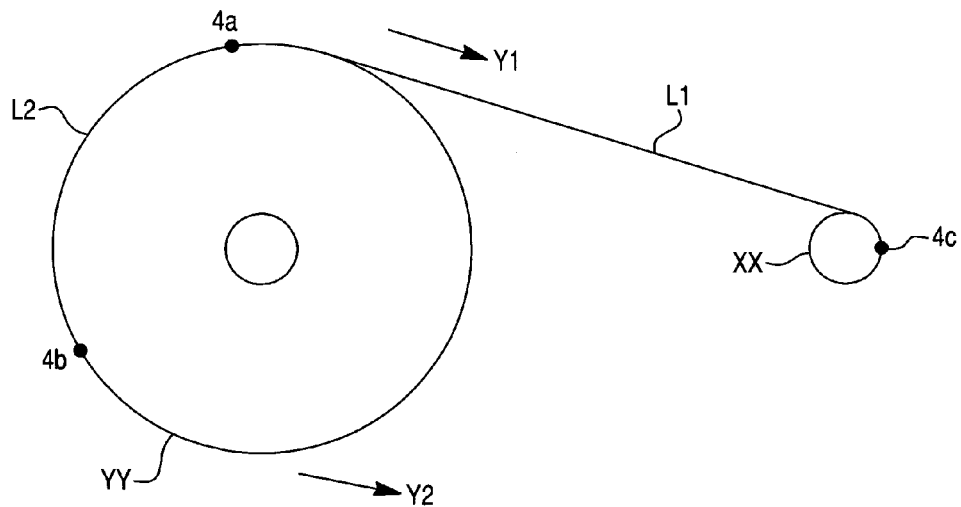
FIG. 36B is a schematic of the triple connector tension element of FIG. 35 coupled to a drive member and a driven member according to an embodiment.

FIG. 36B shows an alternative embodiment where the first and second cable segments L1, L2 of the triple connector cable are redundant in that both the first and second cable segments L1, L2 pull the driven member YY in the direction Y1 when the drive member XX rotates to wind the first and second cable segments L1, L2 about the drive member XX. To drive the driven member YY in the direction Y2, a second triple connector cable can be added. As noted parenthetically above, in the embodiments of FIGS. 36A and 36B, the first and second connectors 4a, 4b can be coupled to one member (e.g., the drive member or the driven member), and the third connector 4c can be coupled to another member (e.g., the driven member or the drive member, respectively).

Another advantage of a triple connector cable is that there is equal tension balance in both the first and second cable segments L1, L2, which may improve haptic stiffness and possibly reduce cable wear. Additionally, the entire triple connector cable can be tensioned using a single cable tension adjustment member. Thus, in accordance with principles of equilibrium, when a triple connector cable is used to form the plurality of transmission sub-elements and a tension force is applied to one of the transmission sub-elements (e.g., the first cable segment L1), an equivalent tension force is applied to another of the transmission sub-elements (e.g., the second cable segment L2). As a result, only one of the cable segments L1, L2 needs to be adjusted to tension the entire triple connector cable.

Stand Assembly

Figure 32:
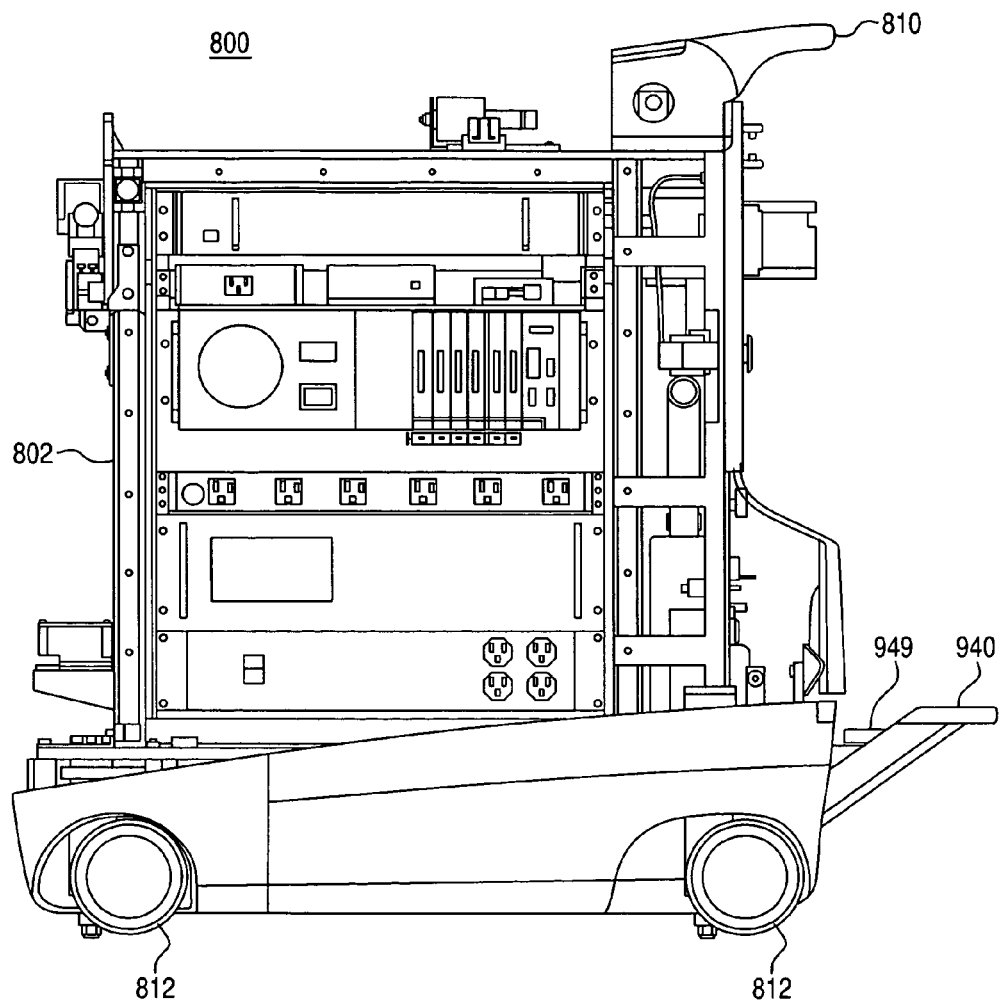
FIG. 32 is a side elevation view of a stand assembly according to an embodiment.

According to an embodiment, as shown in FIG. 1, the robotic arm 10 is disposed on a stand assembly 800. As shown in FIG. 32, the stand assembly 800 includes a structural frame 802 that mechanically supports the robotic arm 10 and provides a mounting area for electronics, computer hardware, and other components associated with the robotic arm 10 as well as power and communications electronics for the guidance module 2 and camera system 3. The structural frame 802 also provides attachment points for protective covers 805. The robotic arm 10 may be secured to the stand, for example, by affixing the baseplate 144 of the first joint assembly 100 to the stand assembly 800 using mechanical fasteners, such as bolts. The stand assembly 800 preferably includes a handle 810 and casters 812 to enhance the mobility of the robotic arm 10 so that the robotic arm 10 can be easily moved, for example, out of the operating room after completion of a surgical procedure.

In addition to ease of mobility, the stand assembly 800 is preferably also configured to maintain the robotic arm 10 in a stable configuration to minimize global movement during surgery. Any suitable stabilizing mechanism may be used. According to an embodiment, the stand incorporates a lift assembly 900 that includes a mobile configuration in which the stand assembly 800 is supported on the casters 812 and a stationary configuration in which the stand assembly 800 is supported on leg members. In the mobile configuration, the stand assembly 800 can easily be rolled from one location to another. In the stationary configuration, the stand assembly 800 is substantially immobile. Preferably, the stand assembly 800 is self-leveling in the stationary configuration. For example, the leg members may include three fixed length leg members 912a and one self-leveling leg member 912b. The three fixed length leg members 912a define a plane, and the self-leveling leg member 912b is compliant to accommodate a floor that is uneven. In one embodiment, the self-leveling leg member 912b is a spring loaded leg member (shown in FIG. 33D) that is compliant in the sense that it travels up and down based on the force of a spring 915 and thus can conform to a floor that is uneven. As a result, the stand assembly 800 advantageously stabilizes itself automatically and will not wobble even when resting on a floor that is not level. Because the stand assembly 800 automatically levels itself, manual leveling of the leg members 912a, 912b is not required. This is particularly advantageous because conventional manual leveling adjustment typically requires adjustment of leg members with a wrench, which means the person carrying out the adjustment has to lay on the floor of the operating room (which may not be clean) and manually raise and/or lower feet on the leg members. This is a time consuming, hazardous process that may have to be repeated each time the stand assembly 800 is moved to a new location. In contrast, the self-leveling feature enables quick set up of the robotic arm 10 and requires no additional tools for final adjustments.

Figure 33A:
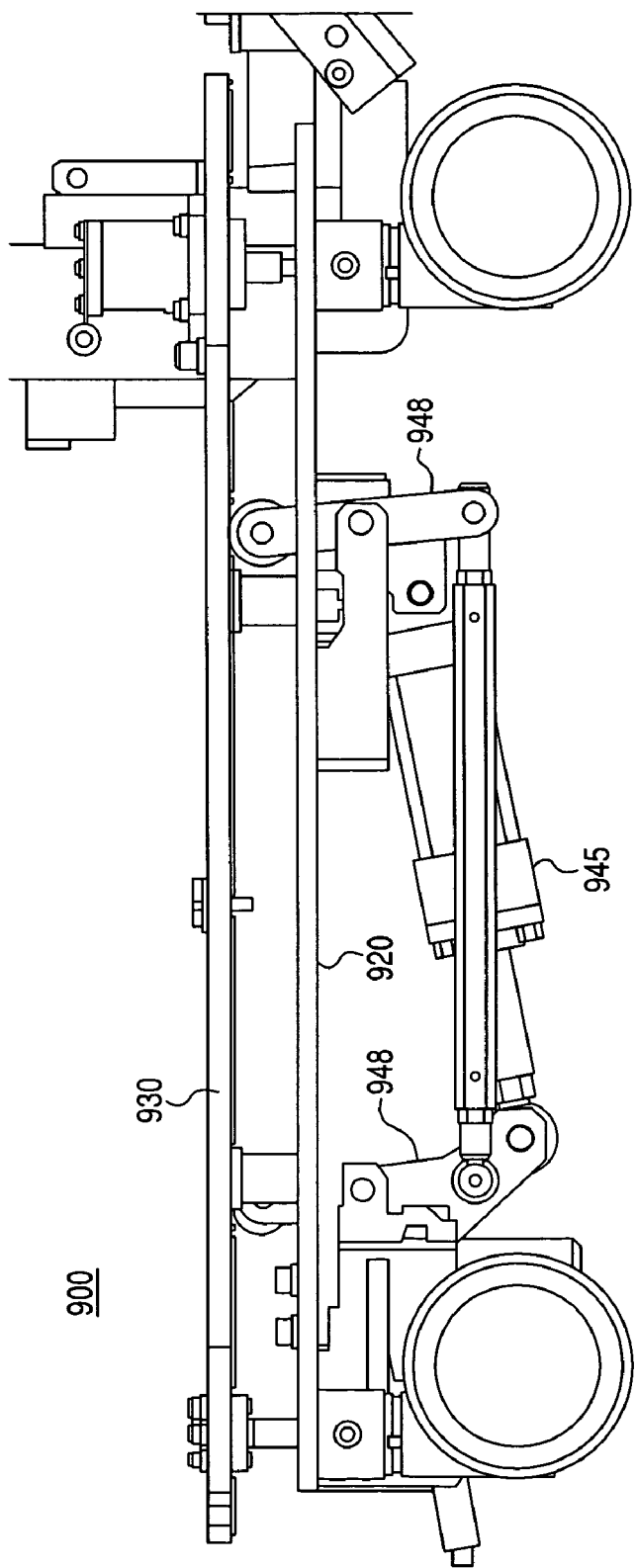
FIG. 33A is a side elevation view of a lift assembly in a mobile configuration according to an embodiment.
Figure 33B:
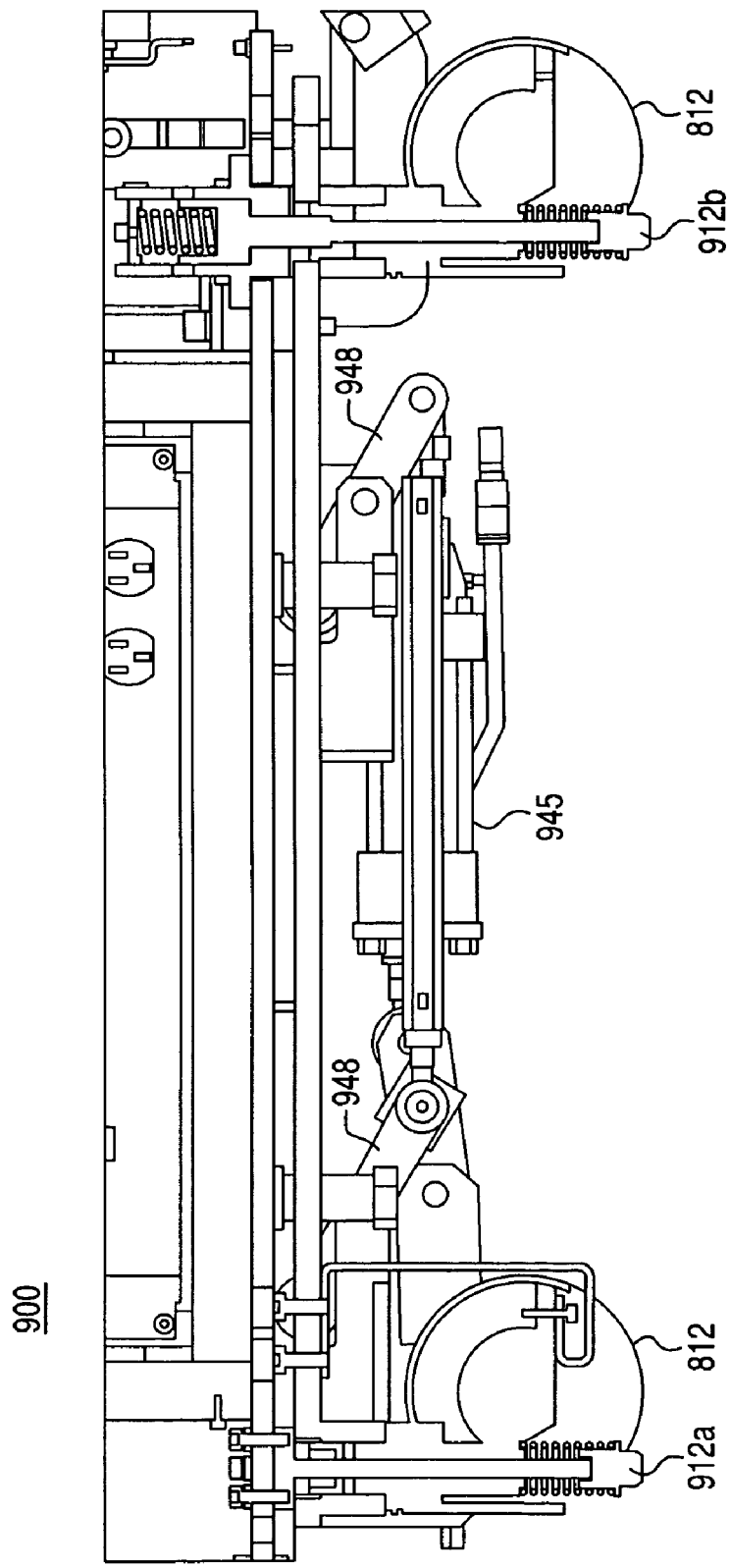
FIG. 33B is a side elevation view of the lift assembly of FIG. 33A in a stationary configuration.
Figure 33C:
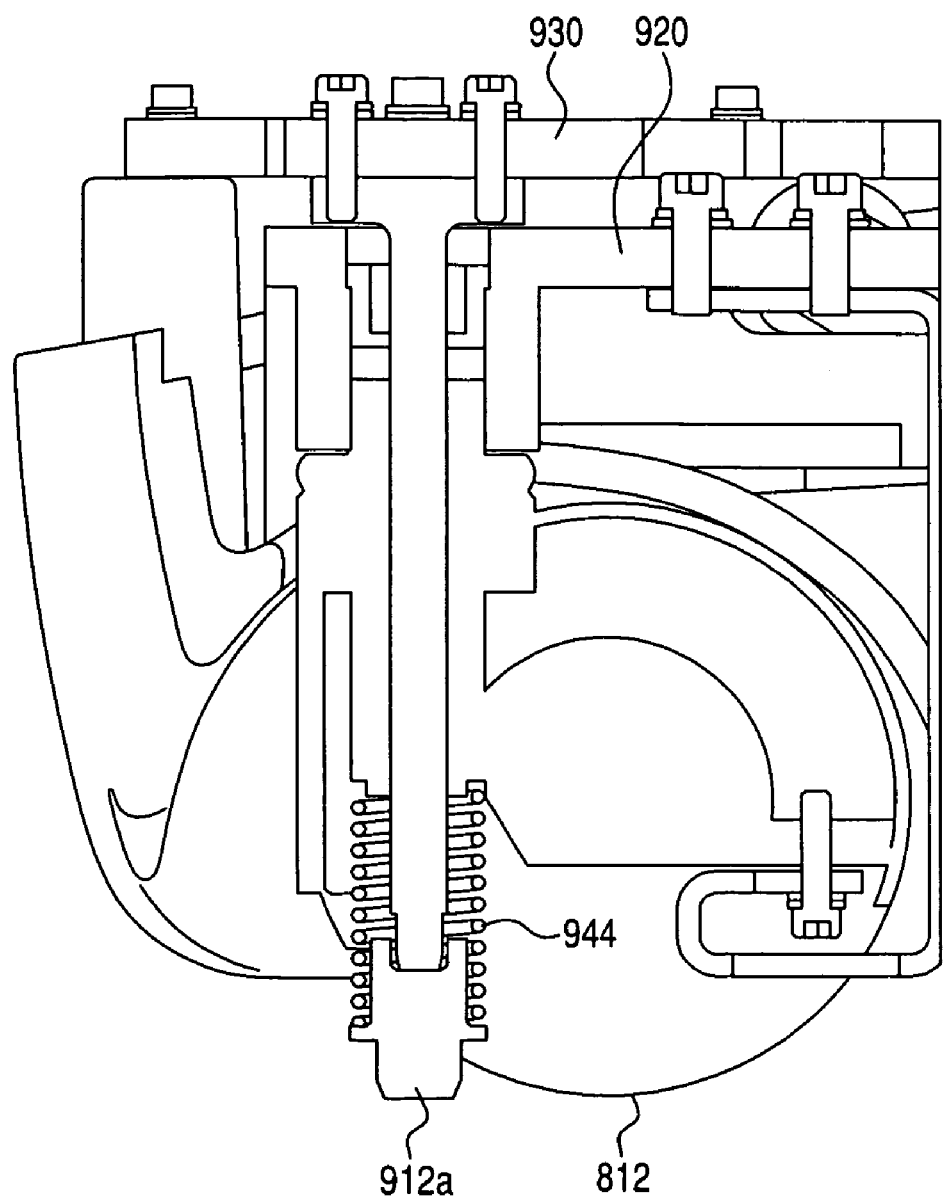
FIG. 33C is a cross-sectional view of a leg member of a lift assembly according to an embodiment.
Figure 33D:
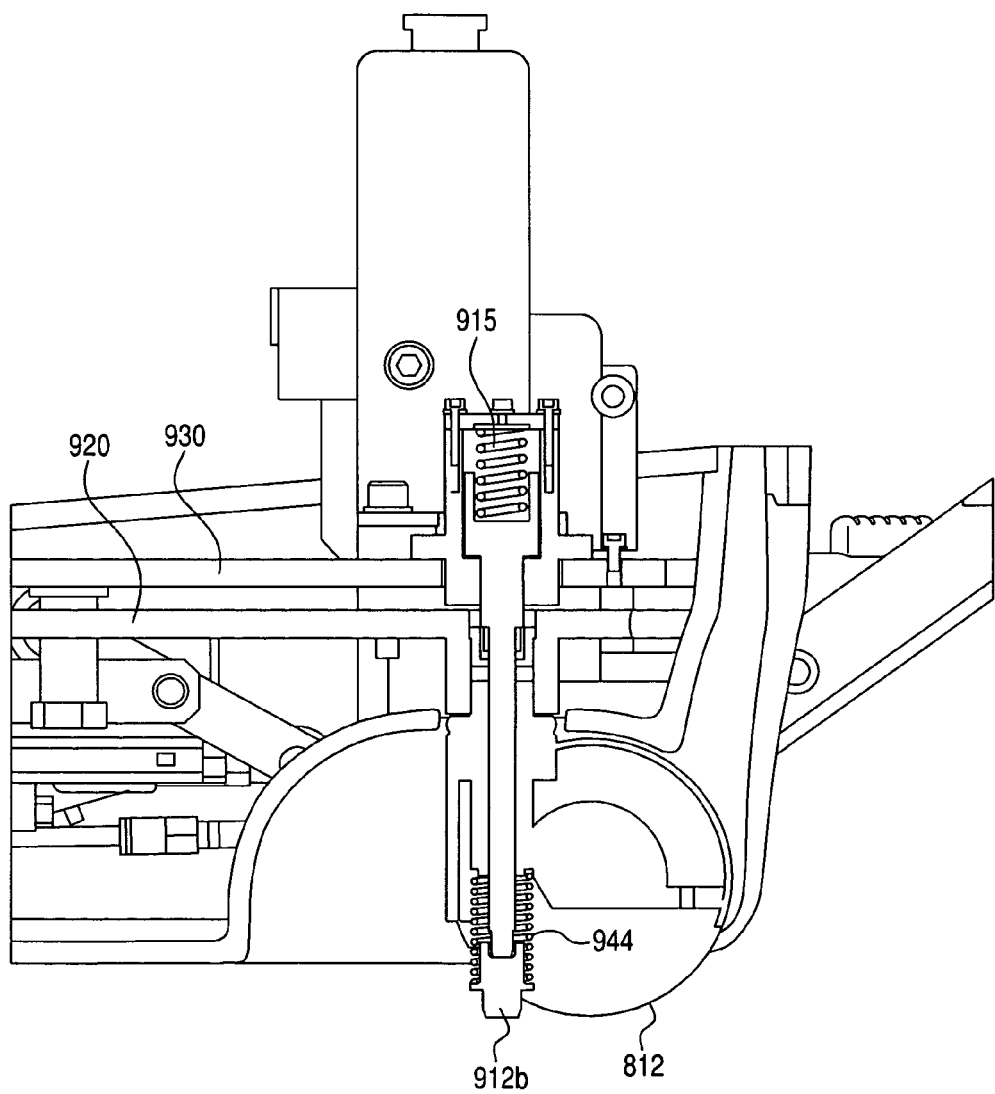
FIG. 33D is a cross-sectional view of a leg member of a lift assembly according to an embodiment.

As shown in FIG. 33A, the lift assembly includes a bottom plate 920 and a top plate 930 that is moveable relative to the bottom plate 920. The casters 812 are mounted on the bottom plate 920, and the fixed length leg members 912a, self-leveling leg member 912b, and structural frame 802 of the stand assembly 800 are mounted on the top plate 930. In operation, a foot pedal 940 operates a hydraulic pump that actuates a hydraulic cylinder 945. As hydraulic pressure increases, the hydraulic cylinder 945 expands (FIG. 33A), and levers 948 pivot to raise the top plate 930. As a result, the leg members 912a, 912b move upward such that the stand assembly 800 is supported by the casters 812 in the mobile configuration. To transition to the stationary configuration, a lift release pedal 949 is depressed, which releases pressure from the hydraulic pump causing the hydraulic cylinder 945 to retract (FIG. 33B), which pivots the levers 948 to lower the top plate 930. As a result, the leg members 912a, 912b move downward such that the stand assembly 800 is supported by the leg members 912a, 912b. A compression spring 944 disposed at the base of each leg member 912a, 912b assists in raising the associated caster 812 to ensure that the leg member 912a, 912b makes contact with the floor. As shown in FIG. 33B, in this embodiment, the leg members 912a, 912b are at least partially disposed within the casters 812 such that each leg member 912a, 912b extends through its corresponding caster 812. One advantage of this configuration is that the lift assembly is more compact. Another advantage is that, in the mobile configuration, the leg members 912a, 912b are retracted within the casters 812, which protects the leg members 912*a*, 912*b* from damage that might be incurred as the stand assembly 800 is rolled over thresholds or rough, uneven flooring or pavement.

Other embodiments of the present invention will be apparent to those skilled in the art from consideration of the specification and practice of the invention disclosed herein. It is intended that the specification and examples be considered as exemplary only.

What is claimed is:

1. A transmission apparatus, comprising:
   a drive member;
   a driven member;
   an at least partially flexible transmission coupled to the drive member and the driven member and configured to cause movement of the driven member in response to movement of the drive member, wherein the flexible transmission includes a first tension element having a first portion coupled to the drive member, a second portion coupled to the driven member, and an intermediate portion between the first portion and the second portion; and
   an adjustment member that engages the intermediate portion of the first tension element,
   wherein the adjustment member is configured to be adjusted to vary a tension force applied to the first tension element,
   wherein the flexible transmission includes a second tension element that is not engaged by the adjustment member,
   wherein the second tension element includes a portion coupled to the drive member and a portion coupled to the driven member, and
   wherein the drive member is disposed between the driven member and the adjustment member.

2. The transmission apparatus of claim 1, wherein the flexible transmission is configured such that a tension force applied to the second tension element is varied when the adjustment member is adjusted to vary the tension force applied to the first tension element.

3. The transmission apparatus of claim 1, wherein the adjustment member includes at least a portion configured to move in a first direction and a second direction, wherein the first and second directions are along at least one of a line and an arc.

4. The transmission apparatus of claim 3, wherein the adjustment member is configured to increase the tension force applied to the first tension element when the adjustment member moves in the first direction.

5. The transmission apparatus of claim 3, wherein the adjustment member is configured to decrease the tension force applied to the first tension element when the adjustment member moves in the second direction.

6. The transmission apparatus of claim 3, wherein the portion of the adjustment member comprises a pulley.

7. The transmission apparatus of claim 1, wherein the adjustment member is configured to move along a predetermined axis.

8. The transmission apparatus of claim 1, wherein the adjustment member is configured to rotate about a predetermined axis.

9. The transmission apparatus of claim 1, wherein the first tension element and the second tension element each comprise a cord.

10. A transmission apparatus, comprising:
    a drive member;
    a driven member;
    an at least partially flexible transmission coupled to the drive member and the driven member and configured to cause movement of the driven member in response to movement of the drive member, wherein the flexible transmission includes a first tension element having a first portion coupled to the drive member, a second portion coupled to the driven member, and an intermediate portion between the first portion and the second portion; and
    an adjustment member that engages the intermediate portion of the first tension element,
    wherein the adjustment member is configured to be adjusted to vary a tension force applied to the first tension element,
    wherein the flexible transmission includes a second tension element that is not engaged by the adjustment member,
    wherein the flexible transmission is configured such that a tension force applied to the second tension element is varied when the adjustment member is adjusted to vary a tension force applied to the first tension element, and
    wherein the drive member is disposed between the driven member and the adjustment member.

11. The transmission apparatus of claim 10, wherein the adjustment member includes at least a portion configured to move in a first direction and a second direction, wherein the first and second directions are along at least one of a line and an arc.

12. The transmission apparatus of claim 11, wherein the portion of the adjustment member comprises a pulley.

13. The transmission apparatus of claim 11, wherein the adjustment member is configured to increase the tension force applied to the first tension element when the adjustment member moves in the first direction.

14. The transmission apparatus of claim 11, wherein the adjustment member is configured to decrease the tension force applied to the first tension element when the adjustment member moves in the second direction.

15. The transmission apparatus of claim 10, wherein the adjustment member is configured to move along a predetermined axis.

16. The transmission apparatus of claim 10, wherein the adjustment member is configured to rotate about a predetermined axis.

17. The transmission apparatus of claim 10, wherein the first tension element and the second tension element each comprise a cord.

* * * * *